US006048704A

United States Patent [19]
Tilson

[11] Patent Number: 6,048,704
[45] Date of Patent: Apr. 11, 2000

[54] PURIFIED AND RECOMBINANT ANTIGENIC PROTEIN ASSOCIATED WITH ABDOMINAL AORTIC ANEURYSM (AAA) DISEASE, AND DIAGNOSTIC AND THERAPEUTIC USE THEREOF

[75] Inventor: Martin David Tilson, Scarsdale, N.Y.

[73] Assignee: The Trustees of Columbia University, New York, N.Y.

[21] Appl. No.: 08/812,586

[22] Filed: Mar. 7, 1997

Related U.S. Application Data

[60] Provisional application No. 60/012,976, Mar. 7, 1996.

[51] Int. Cl.[7] ........................ G01N 33/53; G01N 33/566; C07H 21/04
[52] U.S. Cl. .......................... 435/7.9; 435/7.1; 435/69.1; 435/69.3; 435/70.1; 436/501; 536/23.5
[58] Field of Search ............................ 435/7.1, 7.9, 69.1, 435/69.3, 70.1; 436/501; 536/23.5

[56] References Cited

U.S. PATENT DOCUMENTS 4,558,006  12/1985  Egrie .
5,196,319  3/1993  Coppel et al. .

OTHER PUBLICATIONS

Barinaga, M. (1993) *Science* 261:1669–1670 (Exhibit 3).
Bashir, M.M. et al. (1994) *Biochemistry* 33(2):593–600 (Exhibit 4).
Beckman, E.N. (1986) *Am. J. Clin. Path.* 85(1):21–24 (Exhibit 5).
Bengtsson, H. et al. (1989) *Br. J. Surg.* 76(6): 589–591 (Exhibit 6).
Brophy, C.M. et al. (1991) *Ann. Vasc. Surg.* 5(3):229–233 (Exhibit 7).
Burton, S.J. (1987) "Affinity Chromatography," in *Techniques In Molecular Biology*, Walker J.M. and Gaastra, W., eds., Macmillan Publishing Co., New York, vol. 2, pp. 51–81 (Exhibit 8).
Collin, J. and Walton, J. (1989) *Br. Med. J.* 299:493 (Exhibit 9).
Furjinami, R.S. and Oldstone, M.B.A. (1989) *Immunol. Res.* 8 (1):3–15 (Exhibit 10).
Fullmer, H.M. and Lillie, R.D. (1958) *J. Histochem. Cytochem.* 6:425–430 (Exhibit 11).
Gibson, M.A. et al. (1986) *J. Biol. Chem.* 261(24):11429–11436 (Exhibit 12).
Goding, J.W. (1986) "Affinity Chromatography Using Monoclonal Antibodies," in *Monoclonal Antibodies: Principles AndPractice* Academic Press, London, pp 219–240 (Exhibit 13).
Gregory, A.K. et al. (1996) *Arch. Surg.* 131(1):85–88 (Exhibit 14).
Hirose, H. et al. (1996) *Surgical Forum* XLVII:370–373 (Exhibit 15).
Johansen, K. and Koepsell, T. (1986) *JAMA* 256(14):1943–1936 (Exhibit 16).
Kobayashi, R. et al. (1989) *J. Biol. Chem.* 264(29):17437–17444 (Exhibit 17).
Kobayashi, R. et al. (1994) *Biochem. Biophys. Res. Comun.* 198(3):1262–1266 (Exhibit 18).

Koch, A.E. et al. (1990) *Am. J. Pathol.* 137(5):1199–1213 (Exhibit 19).
Kohler, G. and Milstein, C. (1975) *Nature* 256:495–497 (Exhibit 20).
Konrad, M.W. (1993) "The Immune System As A Barrier To Delivery Of Protein Therapeutics," in *Biological Barriers To Protein Delivery* Plenum Press, New York, pp. 409–437 (Exhibit 21).
Majumder, P.P. et al. (1991) *Am. J. Hum. Genet.* 48(1):164–170 (Exhibit 22).
Minion, D.J. et al. (1993) *Surgery* 114:252–257 (Exhibit 23).
Norrgard, O. et al. (1984) *Surgery* 95(6):650–656 (Exhibit 24).
Ozsvath, K.J. et al. (1996) *Biochem. Biophys. Res. Commun.* 225(2):500–504 (Exhibit 25).
Ozsvath, K.J. et al. (1996) *Annals of the NY Acad. Of Sci.* 800:288–293 (Exhibit 26).
Ozsvath, K.J. et al. (1997) *J. Surg. Res.* 69:277–282 (Exhibit 27).
Tanaka, S. et al. (1994) *J. Vasc. Surg.* 20(2):235–243 (Exhibit 28).
Tilson, M.D. and Seashore, M.R. (1984) *Surg. Gynecol. Obstet.* 158(2):129–132 (Exhibit 29).
Tilson M.D. (1995) *Biochem. Biophys. Res. Commun.* 213(1):40–43 (Exhibit 30).
Tilson, M.D. et al. (1996) *Annals of the NY Acad. of Sci.* 800:208–215 (Exhibit 31).
Tilson, M.D., and Seashore, M.R. (1984) *Am. J. Surg.* 147:551–553 (Exhibit 32).
Tilson, M.D. and Seashore M.R. (1984) *Circulation* Part II; 70(4):II–141 [abstract No. 561] (Exhibit 33).
Tilson, M.D. and Newman, K.M. (1994) "Proteolytic Mechanisms In The Pathogenesis Of Aortic Aneurysms," in *Aneurysms, New Findings And Threatments* Yoa, J.S.T. and Pearce, W.H., eds., Appleton and Lange, Connecticut, pp. 3–10. (Exhibit 34).
Verloes, A. et al. (1995) *J. Vasc. Surg.* 21(4):646–655 (Exhibit 35).
Xia, S. et al. (1996) *Biochem. Biophys. Res. Commun.* 219(1):36–39 (Exhibit 36).

*Primary Examiner*—James C. Housel
*Assistant Examiner*—Rodney P. Swartz
*Attorney, Agent, or Firm*—John P. White; Cooper & Dunham LLP

[57] ABSTRACT

This invention provides an isolated protein of approximately 40 kDa which is purified from human aortic tissue and immunoreactive with AAA-associated immunoglobulin. Also provided are a method of diagnosing AAA disease in a subject using said isolated protein and a pharmaceutical composition comprising said isolated protein. A method of alleviating AAA disease in a subject comprising administering said pharmaceutical composition comprising the isolated protein is also provided. The subject invention also provides a recombinantly produced human aortic protein which is immunoreactive with AAA-associated immunoglobulin. Also provided are a method of diagnosing AAA disease in a subject using said recombinantly produced protein and a pharmaceutical composition comprising said recombinantly produced protein. A method of alleviating AAA disease in a subject comprising administering said pharmaceutical composition comprising the recombinantly produced protein is also provided.

9 Claims, 24 Drawing Sheets

FIG. 5A
Anti Ig Kappa
AAA
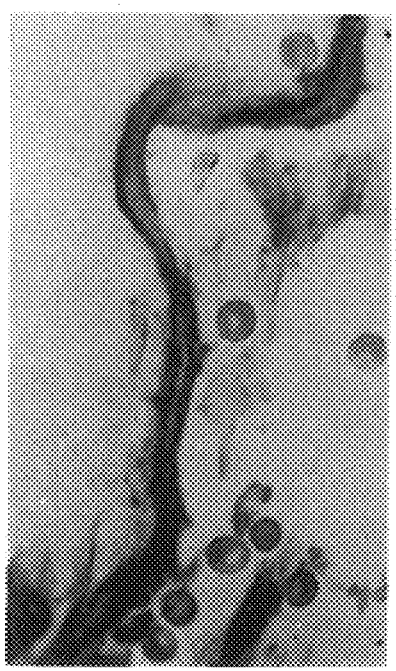
FIG. 5B
Anti Human H Chain
NL
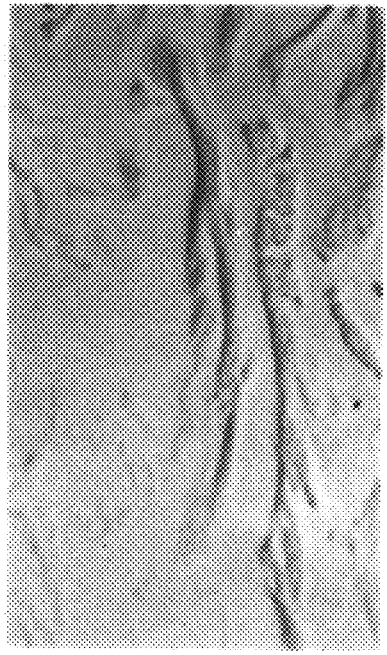
FIG. 5C
FIG. 5D FIG. 19
Anti
Ig Kappa
Anti
Human H Chain

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 105 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Asn Glu Asn Asn Val Val Asn Glu Tyr Ser Gln Glu Leu Glu Lys Xaa
 1               5                  10                  15

Phe Glu Asp Gly Val Leu Asp Pro Asp Tyr Pro Xaa Trp Thr Val Phe
                20                  25                  30

Gln Xaa Tyr Phe Pro Phe Val Asp Leu Met Val Met Ala Asn Gln Pro
        35                  40                  45
```

—continued

```
Met Gly Glu Lys Tyr Tyr Asp Phe Phe Gln Tyr Thr Xaa Gly Met Ala
            50                  55                  60

Lys Glu Tyr Asp Gly Phe Gln Tyr Thr Xaa Gly Met Ala Lys Xaa Ala
 65                  70                  75                  80

Gly Asn Ala Leu Met Asp Gly Ala Ser Gly Leu Met Xaa Trp Xaa Gln
                 85                  90                  95

Trp Arg Gly Phe Tyr Tyr Ser Leu Lys
            100                 105
```

(2) INFORMATION FOR SEQ ID NO:2:

(i) SEQUENCE CHARACTERISTICS:
        (A) LENGTH: 307 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asp Met Arg Val Pro Ala Gln Leu Leu Gly Leu Leu Leu Leu Trp
 1               5                  10                  15

Leu Pro Gly Ala Arg Cys Asp Ile Gln Leu Thr Gln Ser Pro Ser Leu
                20                  25                  30

Leu Ser Ala Ser Val Gly Asp Arg Val Met Ile Thr Cys Arg Ala Ser
             35                  40                  45

Gln Ala Ile Ser Ser Phe Leu Ala Trp Tyr Gln Gln Lys Pro Gly Lys
 50                  55                  60

Ala Pro Lys Leu Leu Ile His Ala Ala Ser Ser Leu Gln Thr Gly Val
 65                  70                  75                  80

Pro Ser Arg Phe Ser Gly Ser Gly Ser Gly Thr Xaa Phe Thr Leu Thr
                 85                  90                  95

Ile Ser Xaa Leu Gln Ser Glu Xaa Leu Gln Leu Tyr Tyr Cys Gln His
            100                 105                 110

Leu Lys Gly Tyr Pro Ile Thr Phe Arg Pro Arg Asp Thr Xaa Gly Xaa
            115                 120                 125

Xaa Xaa Asn Cys Xaa Cys Thr Ile Xaa Ser Ser Ser Arg His Leu
130                 135                 140

Xaa Asn Ile Glu Ile Trp Xaa Cys Leu Cys Cys Xaa Ala Cys Xaa Ile
145                 150                 155                 160

Thr Ser Xaa Pro Lys Lys Ala Lys Phe His Trp Lys Val Asp Asn Pro
                165                 170                 175

Ser Asn Arg Val Thr Pro Gln Lys Asn Phe Pro Xaa Gln Lys Val Phe
            180                 185                 190

Glu Asn Phe Gly Gln Gly Lys Xaa Xaa Pro Gly Gly Ala Lys Val Gln
            195                 200                 205

Gly Glu Gly Gly Lys Xaa Leu Pro Ile Gly Xaa Phe Pro Xaa Glu Cys
            210                 215                 220

Xaa Gln Ser Xaa Thr Ala Arg Thr Ala Leu Thr Ala Ser Ala Ala Pro
225                 230                 235                 240

Thr Arg Lys His Lys Val Tyr Ala Lys Glu Val Thr His Gln Gly Leu
                245                 250                 255

Xaa Ser Ser Ser Leu Thr Pro Ser His Pro Leu Ala Xaa Xaa Asp Pro
            260                 265                 270

Phe Ser Thr Gly Asp Leu Pro Leu Leu Arg Ser Ser Xaa Phe Phe
            275                 280                 285
```

```
Thr Ser Pro Pro Ser Ser Ser Leu Ala Leu Ile Met Leu Met Leu Glu
    290                 295                 300

Glu Asn Glu
305
```

(2) INFORMATION FOR SEQ ID NO:3:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Val Leu Gln Thr Gln Val Phe Ile Ser Leu Leu Trp Ile Ser
1                   5                   10                  15

Gly Ala Asn Gly Asp Ile Val Met Thr Gln Ser Pro Asp Ser Leu Gly
                20                  25                  30

Val Ser Leu Gly Glu Arg Ala Thr Ile Asn Cys Arg Ser Ser Gln Arg
            35                  40                  45

Leu Phe Phe Gly Ser Asn Ser Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Asp Ser Gly Val Leu Thr Asp Ser Leu Ala Ala Gly Leu Gly Xaa Ile
                85                  90                  95

Ser Leu Ser Pro Ser Xaa Xaa Cys Arg Leu Lys Asn Leu Ile Leu Xaa
            100                 105                 110

Leu Ser Ala Ile Ile Ile Ile Ser Xaa Xaa Thr Phe Arg Pro Trp Gly
        115                 120                 125

Thr Xaa Leu Xaa Ile Gln Xaa Lys Cys Trp Xaa Ala Xaa Ile Phe Xaa
    130                 135                 140

Ser Phe Phe Pro Xaa Glu Lys Gln Phe Lys Xaa Xaa Xaa Phe Phe
145                 150                 155                 160

Phe Phe Ser Pro Phe Leu Xaa Gly Trp Xaa Leu Gly Xaa Leu Phe Xaa
                165                 170                 175

Gly Pro Xaa Glu Lys Ile Phe Phe Pro Xaa Gly Pro Lys Lys Arg Gly
            180                 185                 190

Arg Gly Xaa Lys Xaa Pro Pro Asn Trp Gly Lys Ser Pro Ser Gly Xaa
        195                 200                 205

Xaa Xaa Gly Arg Gly Xaa Gln Gly Lys Gly Asn Leu Lys Ala Leu Trp
    210                 215                 220

Xaa Glu Pro Xaa Arg Leu Gly Lys Gly Gly Ile Arg Gly Xaa Asn Lys
225                 230                 235                 240

Xaa Xaa Ala Xaa Glu Val Thr His Ser Gly Leu Ser Phe Ala Xaa Ser
                245                 250                 255

Lys Lys Xaa Xaa Gln Gly Arg Xaa Leu Glu Gly Glu Val Pro Pro Pro
            260                 265                 270

Val Xaa Xaa Xaa Gln Pro Asp Pro Leu Pro Ser Phe Gly Leu Xaa Pro
        275                 280                 285

Phe Phe His Arg Gly
    290
```

(2) INFORMATION FOR SEQ ID NO:4:

(i) SEQUENCE CHARACTERISTICS:
    (A) LENGTH: 196 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:4:

```
Tyr Gly Leu Arg Ser Leu Ser Ala Leu Gln Xaa His Leu Glu Ala Cys
1               5                   10                  15

Leu Leu Thr Ser Gly Gly Xaa Arg Leu Gln Glu Gly Pro Ala Thr
            20                  25                  30

Cys His Leu Pro Cys Asp Gln Ala Lys Lys Trp Asn Xaa Lys Ser Gln
            35                  40                  45

Thr Phe Ile Cys Met Leu Leu Cys Pro Phe Cys Arg Xaa Asn Xaa Ile
        50                  55                  60

Leu Lys Xaa Phe Phe Xaa Leu Gln Phe Ala Leu Ser Phe Pro Thr
65                  70                  75                  80

Pro Thr Thr Asn Pro Leu Phe Glu Xaa Xaa Xaa Ser Pro Glu Pro Xaa
            85                  90                  95

Asp Phe Gln Trp Lys Glu Lys Asn His Xaa Gly Thr Phe Val Ser Asn
            100                 105                 110

Leu Xaa Phe Xaa Leu Asn Ile Ser Lys Phe Phe Cys Xaa Glu Phe Gly
        115                 120                 125

Leu Lys Ala Xaa Ile Arg Ser Pro Xaa Lys Ala Xaa Xaa Gly Met Ser
130                 135                 140

Asp Val Ile Val Lys Cys Pro Val Ile Xaa Phe Met Asn Ala Lys Trp
145                 150                 155                 160

Gly Cys Lys Tyr Phe Leu Asn Val Cys Ile Ser Asn Leu Phe Asp Xaa
                165                 170                 175

Xaa Trp Gly Phe Thr Leu His Pro Cys Ala Cys Phe Pro Asn Cys Glu
            180                 185                 190

Glu Glu Asn Asp
        195
```

(2) INFORMATION FOR SEQ ID NO:5:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Tyr Phe Pro Phe Val Asp Leu Met Val Met Ala Asn Gln Pro Met Gly
1               5                   10                  15

Glu Tyr Tyr Asp Phe Phe Gln Tyr Thr Xaa Gly Met Ala Lys Glu Tyr
            20                  25                  30

Asp Gly Phe Gln Tyr Thr Xaa Gly Met Ala Lys Ile Tyr Ala Gly Asn
            35                  40                  45

Ala Leu Met Asp Gly Ala Ser Gly Leu Met
        50                  55
```

(2) INFORMATION FOR SEQ ID NO:6:

(i) SEQUENCE CHARACTERISTICS:
        (A) LENGTH: 60 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:6:

```
Thr Leu Lys Gln Lys Tyr Glu Leu Arg Val Asp Leu Glu Asp Phe Glu
1               5                   10                  15

Asn Asn Thr Ala Tyr Ala Lys Tyr Ala Asp Phe Ser Ile Ser Pro Asn
            20                  25                  30

Ala Val Ser Ala Glu Glu Asp Gly Tyr Thr Leu Phe Val Ala Gly Phe
        35                  40                  45

Glu Asp Gly Gly Ala Gly Asp Ser Leu Ser Tyr His
50                  55                  60
```

(2) INFORMATION FOR SEQ ID NO:7:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Thr Leu Leu Lys Tyr Glu Leu Arg Val Asp Leu Glu Asp Phe Glu Xaa
1               5                   10                  15

Asn Thr Ala Phe Ala Lys Tyr Ala Asp Phe Ser Ile Ser Pro Asn Ala
            20                  25                  30

Val Ser Ala Glu Glu Asp Gly Tyr Thr Leu Tyr Val Ser Gly Phe Glu
        35                  40                  45

Asp Gly Gly Ala Gly Asp Ser Leu Thr Tyr His
50                  55
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Leu Arg Val Glu Leu Glu Asp Ala Asn Ala Tyr Ile Val Lys Thr Ala
1               5                   10                  15

Gly Asn Ala Leu
            20
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Gln Glu Leu Glu Lys
1               5
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Phe Glu Asp Gly Val Leu Asp Pro Asp Tyr Pro
1               5                   10

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Arg Phe Glu Asp Gly Val Leu Asp Pro Asp Tyr Pro
1               5                   10

(2) INFORMATION FOR SEQ ID NO:12:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Phe Cys Leu Gln Gln Pro Leu Asp Cys Asp Asp Ile Tyr Ala Gln Gly
1               5                   10                  15
Tyr Gln Ser Asp Gly Val Tyr Leu Ile Tyr Pro Ser
                20                  25

(2) INFORMATION FOR SEQ ID NO:13:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Ser Glu Leu Gln Leu Pro Leu Asp Glu Asp Asp Ile Tyr Ala Gln Gly
1               5                   10                  15
Tyr Gln Ala Asp Gly Val Tyr Leu Ile
                20                  25

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Ser Glu Leu Glu Lys His Gln Leu
1               5

(2) INFORMATION FOR SEQ ID NO:15:

(i) SEQUENCE CHARACTERISTICS:
            (A) LENGTH: 374 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:15:

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Leu
                20                  25                  30

Leu Ser Ala Ser Val Gly Asp Arg Val Met Ile Thr Cys Arg Ala Ser
            35                  40                  45

Gln Ala Ile Ser Ser Phe Leu Ala Trp Tyr Gln Gln Lys Pro Gly Lys
        50                  55                  60

Ala Pro Lys Leu Leu Ile His Ala Ala Ser Ser Leu Gln Thr Gly Val
65                  70                  75                  80

Pro Ser Arg Phe Ser Gly Ser Gly Ser Gly Thr Xaa Phe Thr Leu Thr
                85                  90                  95

Ile Ser Xaa Leu Gln Ser Glu Xaa Leu Gln Leu Tyr Tyr Cys Gln His
            100                 105                 110

Leu Lys Gly Tyr Pro Ile Thr Phe Arg Pro Arg Asp Thr Xaa Gly Xaa
        115                 120                 125

Xaa Xaa Asn Cys Xaa Cys Thr Ile Xaa Ser Ser Ser Arg His Leu
130                 135                 140

Xaa Asn Ile Glu Ile Trp Xaa Cys Leu Cys Cys Xaa Ala Cys Tyr Xaa
145                 150                 155                 160

Ile Thr Ser Xaa Pro Lys Lys Ala Lys Phe His Trp Lys Val Asp Asn
                165                 170                 175

Pro Ser Asn Arg Val Thr Pro Gln Lys Asn Phe Pro Xaa Gln Lys Val
            180                 185                 190

Phe Glu Asn Phe Gly Gln Gly Lys Xaa Gly Xaa Lys Gly Xaa Gly Xaa
        195                 200                 205

Xaa Xaa Xaa Phe Phe Phe Xaa Pro Phe Gly Xaa Xaa Xaa Xaa Phe Gly
    210                 215                 220

Xaa Xaa Cys Xaa Cys Trp Xaa Pro Gly Xaa Xaa Lys Ile Phe Xaa Xaa
225                 230                 235                 240

Pro Gly Gly Ala Lys Val Gln Gly Glu Gly Gly Lys Xaa Leu Pro Ile
                245                 250                 255

Gly Xaa Phe Pro Xaa Glu Cys Xaa Gln Ser Xaa Thr Ala Arg Thr Ala
            260                 265                 270

Leu Thr Ala Ser Ala Ala Pro Thr Arg Lys His Lys Val Tyr Ala Lys
        275                 280                 285

Glu Val Thr His Gln Gly Leu Pro Val Thr Lys Ser Xaa Asn Arg Gly
    290                 295                 300

Glu Cys Xaa Xaa Arg Glu Lys Cys Pro His Leu Xaa Xaa Ser Ser Ser

```
                305                 310                 315                 320
Leu Thr Pro Ser His Pro Leu Ala Xaa Xaa Asp Pro Phe Ser Thr Gly
                325                 330                 335

Asp Leu Pro Leu Leu Arg Ser Ser Xaa Phe Phe Thr Ser Pro Pro
                340                 345                 350

Ser Ser Ser Leu Ala Xaa Ile Phe Ala Leu Ile Met Leu Met Leu Glu
                355                 360                 365

Glu Asn Glu Xaa Ile Lys
    370
```

(2) INFORMATION FOR SEQ ID NO:16:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Asp Met Arg Val Pro Ala Gln Leu Leu Gly Leu Leu Leu Leu Trp
1               5                   10                  15

Leu Pro Gly Ala Arg Cys Ala Ile Arg Ile Ala Gln Ser Pro Ser Ser
                20                  25                  30

Leu Ser Ala Ser Thr Gly Asp Arg Val Thr Ile Thr Cys Arg Ala Ser
                35                  40                  45

Gln Gly Ile Ser Asn Tyr Leu Ala Trp Tyr Gln Gln Lys Pro Gly Gln
            50                  55                  60

Ala Pro Arg Leu Leu Ile Tyr Asp Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Gly Gln Gln
                100                 105                 110

Tyr Gly Ser Ser Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Gly Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Gly Glu Val Thr His Gln Gly Leu Ser
            210                 215                 220

Ser Pro Val Thr Lys Ser Phe Asn Arg Gly Glu
225                 230                 235
```

NFORMATION FOR SEQ ID NO:17:

(i) SEQUENCE CHARACTERISTICS:
    (A) LENGTH: 28 amino acids
    (B) TYPE: amino acid
    (C) STRANDEDNESS: single (D) TOPOLOGY: linear ii) MOLECULE TYPE: protein (xi) SEQUENCE DESCRIPTION: SEQ ID NO:17:

Leu Leu Leu Trp Ile Gly Ala Asp Ile Thr Gln Ser Pro Leu Val Ser
1               5                   10                  15
Gly Glu Arg Ala Thr Ile Asn Cys Arg Ser Ser Gln
            20                  25

(2) INFORMATION FOR SEQ ID NO:18:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:18:

Leu Leu Ala Leu
1

(2) INFORMATION FOR SEQ ID NO:19:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:19:

Arg Ile Phe Glu Asn Tyr
1               5

(2) INFORMATION FOR SEQ ID NO:20:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:20:

Lys Gly Arg Lys Gly
1               5

(2) INFORMATION FOR SEQ ID NO:21:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:21:

Lys Leu Tyr Glu
1

(2) INFORMATION FOR SEQ ID NO:22:

```
      (i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:22:

Ser Ser Ser Leu
1

(2) INFORMATION FOR SEQ ID NO:23:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:23:

Ser Thr Gly Asp Ile Pro Met Leu
1               5

(2) INFORMATION FOR SEQ ID NO:24:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:24:

Thr Ser Thr Ala Asp
1               5

(2) INFORMATION FOR SEQ ID NO:25:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:25:

Phe Phe Phe Ser Pro
1               5

(2) INFORMATION FOR SEQ ID NO:26:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:26:

Phe Phe Phe Ser
1

(2) INFORMATION FOR SEQ ID NO:27:
```

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:27:

Phe Phe Tyr Ser
1

(2) INFORMATION FOR SEQ ID NO:28:

(i) SEQUENCE CHARACTERISTICS:
    (A) LENGTH: 328 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:28:

```
Met Val Leu Gln Thr Gln Val Phe Ile Ser Leu Leu Trp Ile Ser
1               5                   10                  15

Gly Ala Asn Gly Asp Ile Val Met Thr Gln Ser Pro Asp Ser Leu Gly
                20                  25                  30

Val Ser Leu Gly Glu Arg Ala Thr Ile Asn Cys Arg Ser Ser Gln Arg
            35                  40                  45

Leu Phe Phe Gly Ser Asn Ser Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Asp Ser Gly Val Leu Thr Asp Ser Leu Ala Ala Gly Leu Gly Xaa Ile
                85                  90                  95

Ser Leu Ser Pro Ser Xaa Xaa Cys Arg Leu Lys Asn Leu Ala Ile Leu
            100                 105                 110

Xaa Leu Ser Ala Ile Ile Ile Ser Xaa Xaa Thr Phe Arg Pro Trp
    115                 120                 125

Gly Thr Xaa Leu Xaa Ile Gln Xaa Lys Cys Trp Xaa Ala Xaa Ile Phe
    130                 135                 140

Xaa Ser Phe Phe Pro Pro Xaa Glu Lys Gln Phe Lys Phe Phe Phe
145                 150                 155                 160

Ser Pro Phe Leu Xaa Gly Trp Xaa Leu Gly Xaa Leu Phe Xaa Gly Pro
                165                 170                 175

Xaa Glu Lys Ile Phe Phe Pro Xaa Gly Pro Lys Lys Arg Gly Arg Gly
            180                 185                 190

Xaa Lys Xaa Pro Pro Asn Trp Gly Lys Ser Pro Ser Gly Xaa Xaa Xaa
    195                 200                 205

Gly Arg Gly Xaa Gln Gly Lys Gly Asn Leu Lys Ala Leu Trp Xaa Glu
210                 215                 220

Pro Xaa Arg Leu Gly Lys Gly Gly Ile Arg Gly Xaa Asn Lys Xaa Xaa
225                 230                 235                 240

Ala Xaa Glu Val Thr His Ser Gly Leu Ser Phe Ala Xaa Ser Lys Lys
    245                 250                 255

Xaa Xaa Gln Gly Arg Xaa Leu Glu Gly Glu Val Pro Pro Val Xaa
            260                 265                 270

Xaa Xaa Gln Pro Asp Pro Leu Pro Ser Phe Gly Leu Xaa Pro Phe Phe
```

```
                275                 280                 285
His Arg Gly Xaa Thr Pro Ile Xaa Val Xaa Gln Xaa Ile Phe Tyr Xaa
290                 295                 300

Thr Pro Leu Xaa Xaa Leu Gly Phe Asn Tyr Xaa Asn Val Xaa Xaa Xaa
305                 310                 315                 320

Xaa Ile Asn Lys Val Xaa Phe Leu
                325
```

(2) INFORMATION FOR SEQ ID NO:29:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Met Val Leu Gln Thr Gln Val Phe Ile Ser Leu Leu Trp Ile Ser
1               5                   10                  15

Gly Ala Gly Asp Ile Val Met Thr Gln Ser Pro Asp Ser Leu Ala Val
                20                  25                  30

Ser Leu Gly Glu Arg Ala Thr Ile Asn Cys Lys Ser Ser Gln Ser Val
            35                  40                  45

Leu Tyr Ser Ser Asn Asn Lys Asn Tyr Leu Ala Trp Tyr Gln Gln Lys
50                  55                  60

Pro Gly Gln Ala Pro Arg Leu Leu Ile Tyr Asp Ala Ser Ser Arg Ala
65                  70                  75                  80

Thr Gly Ile Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Gly Gln Gln Tyr Gly Ser Ser Pro Leu Thr Phe Gly Gly Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Glu Ile Thr Ala Ser Val Val Gly Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Gly Glu Val Thr His Gln
210                 215                 220

Gly Leu Ser Ser Pro Val Thr Lys Ser Phe Asn Arg Gly Glu Gly
225                 230                 235
```

(2) INFORMATION FOR SEQ ID NO:30:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Phe Phe Phe Pro Phe Ala Ala Ala Lys Lys Val Tyr Ala Glu Val Thr
1               5                   10                  15

His Gly Leu Ser Glu
            20

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Ser Ile Ser Pro
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Ser Ile Ser Pro
1

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Leu Leu Leu Leu Ser
1               5

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Cys Arg Ile Lys Asn
1               5

(2) INFORMATION FOR SEQ ID NO:35:

(i) SEQUENCE CHARACTERISTICS:
        (A) LENGTH: 5 amino acids
        (B) TYPE: amino acid

```
        (C) STRANDEDNESS: single
        (D) TOPOLOGY: linear (ii) MOLECULE TYPE: protein (xi) SEQUENCE DESCRIPTION: SEQ ID NO:35:

Phe Phe Phe Ser Pro
1               5

(2) INFORMATION FOR SEQ ID NO:36:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Phe Tyr Tyr Ser
1

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Phe Tyr Tyr Ser
1

(2) INFORMATION FOR SEQ ID NO:38:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

Phe Phe Phe Ser
1

(2) INFORMATION FOR SEQ ID NO:39:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

Trp Tyr Gln Gln Lys Pro Gly Lys Ala Pro Lys Leu Leu Ile His Ala
1               5                   10                  15

Ala Ser Ser Leu Gln Thr Gly Val Pro Ser Arg Phe Ser Gly Ser Gly
                20                  25                  30

Ser Gly Thr Xaa Phe Thr Leu Thr
            35                  40
```

(2) INFORMATION FOR SEQ ID NO:40:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

```
Trp Tyr Gln Gln Lys Pro Gly Lys Ala Pro Lys Leu Leu Ile Tyr Ala
1               5                  10                  15

Ala Ser Thr Leu Gln Ser Gly Val Pro Ser Arg Phe Ser Gly Ser Gly
            20                  25                  30

Ser Gly Thr Asp Phe Thr Leu Thr
        35                  40
```

(2) INFORMATION FOR SEQ ID NO:41:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Ser Gly Pro Arg Phe Cys Gly Ser Val Ser Phe Phe Arg Gly Trp Asn
1               5                  10                  15

Asp Tyr Lys Leu Gly Phe Gly Arg Ala Asp Gly Glu Tyr Trp Leu Gly
            20                  25                  30

Leu Gln Asn Met His Leu Leu Thr
        35                  40
```

(2) INFORMATION FOR SEQ ID NO:42:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

```
Phe Gln Lys Arg Phe Asn Gly Ser Val Ser Phe Phe Arg Gly Trp Asn
1               5                  10                  15

Asp Tyr Lys Leu Gly Phe Gly Arg Ala Asp Gly Glu Tyr Trp Leu Gly
            20                  25                  30

Leu Gln Asn Met His Leu Leu Thr
        35                  40
```

(2) INFORMATION FOR SEQ ID NO:43:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Phe Gln Arg Arg Ile Asp Gly Thr Ile Asn Phe Tyr Arg Ser Trp Ser
 1               5                  10                  15

Tyr Tyr Gln Thr Gly Phe Gly Asn Leu Asn Thr Glu Phe Trp Leu Gly
                20                  25                  30

Asn Asp Asn Ile His Tyr Leu Thr Phe Gln Arg Gly Phe Arg Trp Tyr
                35                  40                  45

Gly Phe Gly Glu Trp Leu Gly Asn His Leu Thr
                50                  55
```

(2) INFORMATION FOR SEQ ID NO:44:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Phe Gln Lys Arg Phe Asn Gly Ser Val Ser Phe Phe Arg Gly Trp Asn
 1               5                  10                  15

Asp Tyr Lys Leu Gly Phe Gly Arg Ala Asp Gly Glu Tyr Trp Leu Gly
                20                  25                  30

Leu Gln Asn Met His Leu Leu Thr
                35                  40
```

(2) INFORMATION FOR SEQ ID NO:45:

(i) SEQUENCE CHARACTERISTICS:
        (A) LENGTH: 233 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Met Lys Lys Thr Ala Ile Ala Ile Ala Val Ala Leu Ala Gly Phe Ala
 1               5                  10                  15

Thr Val Ala Gln Ala Ala Glu Leu Thr Gln Ser Pro Ser Ser Val Ser
                20                  25                  30

Ala Ser Val Gly Asp Arg Val Thr Ile Thr Cys Arg Ala Ser Gln Gly
                35                  40                  45

Ile Ser Ser Trp Leu Ala Trp Tyr Gln Gln Lys Pro Gly Lys Ala Pro
         50                  55                  60

Lys Leu Leu Ile Tyr Ser Ala Ser Ser Leu Gln Ser Gly Val Pro Ser
65                  70                  75                  80

Arg Phe Ser Gly Ser Gly Ser Gly Thr Asp Phe Ser Leu Thr Ile Ser
                85                  90                  95

Ser Leu Gln Pro Glu Asp Ser Ala Thr Tyr Tyr Cys Gln Gln Ala Asn
                100                 105                 110

Ser Phe Pro Tyr Thr Phe Gly Gln Gly Thr Lys Val Glu Ile Lys Arg
                115                 120                 125

Thr Val Ala Ala Pro Ser Val Phe Ile Phe Pro Pro Ser Asp Glu Gln
                130                 135                 140

Leu Lys Ser Gly Thr Ala Ser Val Val Cys Leu Leu Asn Asn Phe Tyr
145                 150                 155                 160

Arg Glu Ala Lys Val Gln Trp Lys Val Asp Asn Ala Leu Gln Ser Gly
```

-continued

```
                     165                 170                 175
Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
            195                 200                 205

Lys Leu Tyr Ala Cys Glu Val Thr His Gln Gly Leu Ser Ser Pro Val
        210                 215                 220

Thr Lys Ser Phe Asn Arg Gly Glu Cys
225                 230
```

(2) INFORMATION FOR SEQ ID NO:46:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Leu Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Met Phe Gly Gln Gly Thr
        115                 120                 125

Lys Val Glu Ile Lys Arg Thr
    130                 135
```

(2) INFORMATION FOR SEQ ID NO:47:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Ser Glu Leu Gln Leu Pro Leu Asp Glu Asp Asp Ile Tyr Ala Gln Gly
1               5                   10                  15

Tyr Gln Ala Asp Gly Val Tyr Leu Ile Pro Ser Gly Pro Arg Phe Cys
            20                  25                  30

Gly Ser Val Ser Phe Phe Arg Gly Trp Asn Asp Tyr Lys Leu Gly Phe
        35                  40                  45

Gly Arg Ala Asp Gly Glu Tyr Trp Leu Gly Leu Gln Asn Met His Leu
    50                  55                  60
```

```
Leu Thr Leu Lys Tyr Glu Leu Arg Val Asp Leu Glu Asp Phe Glu Xaa
 65                  70                  75                  80

Asn Thr Ala Phe Ala Lys Tyr Ala Asp Phe Ser Ile Ser Pro Asn Ala
                 85                  90                  95

Val Ser Ala Glu Glu Asp Gly Tyr Thr Leu Tyr Val Ser Gly Phe Glu
                100                 105                 110

Asp Gly Gly Ala Gly Asp Ser Leu Thr Tyr His Ser Gly Gln Lys
            115                 120                 125
```

(2) INFORMATION FOR SEQ ID NO:48:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

```
Met Lys Ala Leu Leu Ala Leu Pro Leu Leu Leu Leu Leu Ser Thr Pro
  1               5                  10                  15

Pro Cys Ala Pro Gln Val Ser Gly Ile Arg Gly Asp Ala Leu Glu Arg
                 20                  25                  30

Phe Cys Leu Gln Gln Pro Leu Asp Cys Asp Asp Ile Tyr Ala Gln Gly
             35                  40                  45

Tyr Gln Ser Asp Gly Val Tyr Leu Ile Tyr Pro Ser Gly Pro Ser Val
         50                  55                  60

Pro Val Pro Val Phe Cys Asp Met Thr Thr Glu Gly Gly Lys Trp Thr
 65                  70                  75                  80

Val Phe Gln Lys Arg Phe Asn Gly Ser Val Ser Phe Phe Arg Gly Trp
                 85                  90                  95

Asn Asp Tyr Lys Leu Gly Phe Gly Arg Ala Asp Gly Glu Tyr Trp Leu
                100                 105                 110

Gly Leu Gln Asn Met His Leu Leu Thr Leu Lys Gln Lys Tyr Glu Leu
            115                 120                 125

Arg Val Asp Leu Glu Asp Phe Glu Asn Asn Thr Ala Tyr Ala Lys Tyr
130                 135                 140

Ala Asp Phe Ser Ile Ser Pro Asn Ala Val Ser Ala Glu Glu Asp Gly
145                 150                 155                 160

Xaa Thr Leu Phe Val Ala Gly Phe Glu Asp Gly Ala Gly Asp Ser
                165                 170                 175

Leu Ser Tyr His Ser Gly Gln Lys Phe Ser Thr Phe Asp Arg Asp Gln
            180                 185                 190

Asp Leu Phe Val Gln Asn Cys Ala Ala Leu Ser Ser Gly Ala Arg Trp
            195                 200                 205

Phe Arg Ser Cys His Phe Ala Asn Leu Asn Gly Phe Tyr Leu Gly Gly
210                 215                 220

Ser Leu Ser Tyr Ala Asn Gly Ile Asn Trp Trp Lys Gly Phe Tyr Tyr
225                 230                 235                 240

Ser Leu Lys Arg Thr Glu Met Lys Ile Arg Arg Ala
                245                 250
```

(2) INFORMATION FOR SEQ ID NO:49:

(i) SEQUENCE CHARACTERISTICS:
        (A) LENGTH: 282 amino acids
        (B) TYPE: amino acid (C) STRANDEDNESS: single
            (D) TOPOLOGY: linear (ii) MOLECULE TYPE: protein (xi) SEQUENCE DESCRIPTION: SEQ ID NO:49:

Met Phe Ser Phe Ile Met Lys Ala Ala Ile Leu Leu Ile Leu Val Gly
1               5                   10                  15

Cys Ile Ser Phe Cys Ile Ser Ser Glu Pro Leu Asn Glu Ser Glu Ile
            20                  25                  30

Thr Phe Glu Arg Glu Glu Arg Ser Leu Ala Asp Pro Ala Gly Arg Gln
        35                  40                  45

Lys Arg Gln Ser Gly Leu Ser Cys Pro Lys Arg Ile Ser His Ser Pro
50                  55                  60

Glu Tyr Pro Arg Asp Cys Tyr Asp Ile Leu Gln Ser Cys Ser Gly Gln
65                  70                  75                  80

Ser Pro Pro Ser Gly Gln Tyr Tyr Ile Gln Pro Asp Gly Gly Asn Leu
            85                  90                  95

Ile Lys Val Tyr Cys Asp Met Glu Thr Asp Glu Gly Gly Trp Thr Val
            100                 105                 110

Phe Gln Arg Arg Ile Asp Gly Thr Ile Asn Phe Tyr Arg Ser Trp Ser
        115                 120                 125

Tyr Tyr Gln Thr Gly Phe Gly Asn Leu Asn Thr Glu Phe Trp Leu Gly
130                 135                 140

Asn Asp Asn Ile His Tyr Leu Thr Ser Gln Gly Asp Tyr Glu Leu Arg
145                 150                 155                 160

Val Glu Leu Asn Asn Thr Leu Gly Asn His Tyr Tyr Ala Lys Tyr Asn
            165                 170                 175

Lys Phe Arg Ile Gly Asp Ser Phe Ser Glu Tyr Leu Leu Val Leu Gly
        180                 185                 190

Ala Tyr Ser Gly Thr Ala Gly Asp Ser Leu Ala Tyr His Asn Thr Met
        195                 200                 205

Arg Phe Ser Thr Tyr Asp Asn Asp Asn Asp Val Tyr Ser Ile Asn Cys
210                 215                 220

Ala Ser His Ser Ser Tyr Gly Arg Gly Ala Trp Trp Tyr Lys Ser Cys
225                 230                 235                 240

Leu Leu Ser Asn Leu Asn Gly Gln Tyr Tyr Asp Tyr Ser Gly Ala Pro
            245                 250                 255

Ser Ile Tyr Trp Ser Tyr Leu Pro Gly Asp Asn Asp Gln Ile Pro Phe
            260                 265                 270

Ala Glu Met Lys Leu Arg Asn Arg Ser Ile
        275                 280

(2) INFORMATION FOR SEQ ID NO:50:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

Phe Glu Asp Gly Val Leu Asp Pro Asp Tyr Pro
1               5                   10

(2) INFORMATION FOR SEQ ID NO:51:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:51:

Arg Phe Glu Asp Gly Val Leu Asp Pro Asp Tyr Pro
1               5                   10

(2) INFORMATION FOR SEQ ID NO:52:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:52:

Asp Gly Val Tyr Leu Pro
1               5

(2) INFORMATION FOR SEQ ID NO:53:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:53:

Asp Gly Val Tyr Leu Pro
1               5

(2) INFORMATION FOR SEQ ID NO:54:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:54:

Tyr Glu Leu Arg Ser Leu Ser
1               5

(2) INFORMATION FOR SEQ ID NO:55:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:55:

Tyr Glu Leu Lys
1

(2) INFORMATION FOR SEQ ID NO:56:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

Ser Leu Ser Ala
1

(2) INFORMATION FOR SEQ ID NO:57:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:57:

Arg Gly Phe Tyr Tyr
1            5

(2) INFORMATION FOR SEQ ID NO:58:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:58:

Arg Val Tyr Phe Phe
1            5

(2) INFORMATION FOR SEQ ID NO:59:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Glu Glu Lys Asn
1

(2) INFORMATION FOR SEQ ID NO:60:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Tyr Gly Leu Arg
1

(2) INFORMATION FOR SEQ ID NO:61:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

Trp Gly Phe Thr

PURIFIED AND RECOMBINANT ANTIGENIC PROTEIN ASSOCIATED WITH ABDOMINAL AORTIC ANEURYSM (AAA) DISEASE, AND DIAGNOSTIC AND THERAPEUTIC USE THEREOF

This application claims benefit of copending U.S. Provisional Application Ser. No. 60/012,976 filed Mar. 7, 1996.

Throughout this application, various references are referred to in parentheses. Disclosures of these publication in their entireties are hereby incorporated by reference into this application to more fully describe the state of the art to which this invention pertains. Full bibliographic citation for these references may be found at the end of this application, preceding the claims.

BACKGROUND OF THE INVENTION

Microfibrils, 10–14 nm in diameter, are extracellular matrix proteins which play important roles in the assembly and maintenance of elastic fibers.[1,2] A bovine microfibril-associated glycoprotein (MAGP) with MW 31 kDa was discovered in 1986,[3,4] and then cloned in 1994.[5] Kobayashi et al. Reported a bovine MAGP-36 with calcium-binding and fibrinogen-like domains, with a tissue distribution uniquely limited to aorta.[6] A human MAGP, implicated to Smith Magenis syndrome, was sequenced in 1995.[7]

Immunoglobulin (IgG) purified from the aortic wall of patients with abdominal aortic aneurysms (AAAs) is immunoreactive with a human aortic protein that is homologous to MAGP-36.[8] As described herein, the protein has been purified and partially sequenced. It has vitronectin and fibrinogen-like domains, along with a putative calcium-binding domain.[9] It is designated Aortic Aneurysm-Autoantigenic Protein-40 kDa or Aortic-Aneurysm-Associated Protein-40 (AAAP-40).[9]

Another matrix protein detected in human embryonic tissue (sulfated protein 30 kDa=SP-30) has been reported to be immunoreactive with monoclonal antibodies against human vitronectin, and it co-distributes in tissue with the protein that is immunoreactive with antibody against MAGP-31. A sequence in AAAP-40 matches residues #230–240 in human vitronectin. It was demonstrated that AAAP-40 was immunoreactive with rabbit anti-human vitronectin antibody. In addition, the experiments described in this application were carried out to clone the cDNA encoding AAAP-40, express it as a recombinant, and assign it conclusively as a human MAGP.

Nomenclature of the microfibrillar proteins associated with the elastin fiber is confusing. A principal component of the microfibril is fibrillin (fib-15), discovered by Sakai, et al.,[1] and Marfan's syndrome has been traced to mutations in the gene for fibrillin on chromosome 15.[2,3,4] A bovine microfibrillar protein (Mr apx. 31 kDa) was discovered in 1986 by Gibson, et al.,[5,6] who coined the term "microfibril-associated glycoprotein" (MAGP). Bashir, et al. have also cloned the gene for this protein.[7] Kobayashi, et al. reported a 36 kDa calcium-binding protein, also in cow, with tissue distribution uniquely limited to the aorta (MAGP-36).[8] The second human MAGP (deduced MW 21 kDa) was recently reported to have an open reading frame of 255 amino acids and to be linked to Smith Magenis syndrome.[9] The authors of the paper describing the Smith Magenis protein prefer the abbreviation "MFAP", to avoid confusion with abbreviations for microfilamentous proteins.

It has been reported that IgG from the aortic wall of patients with abdominal aortic aneurysms (AAA) is immunoreactive with a human aortic protein (MW apx. 80 kDa) that has features of the bovine aortic protein of Kobayshi, et al. (MAGP-36).[10] MAGP-36 occurs in nature as a disulfide-bonded dimer, so further tissue extractions under reducing conditions as described by Prosser, et al. were carried out as described herein.[11] This approach has led to the partial characterization of a protein of apx. 40 kDa that is immunoreactive with AAA IgG. This protein is called Aortic Aneurysm-Autoantigenic Protein-40 kDa or Aortic-Aneurysm-Associated Protein-40 (AAAP-40). The present application describes its partial sequence and suggests that, since it is the third human microfibrillar protein to be described, it be called MAGP-3.

SUMMARY OF THE INVENTION

This invention provides an isolated protein of approximately 40 kDa which is purified from human aortic tissue and immunoreactive with AAA-associated immunoglobulin. This invention provides an isolated protein has the amino acid sequence set forth in SEQ ID NO:1.

This invention provides a recombinantly produced human aortic protein which is immunoreactive with both AAA-associated immunoglobulin and human kappa immunoglobulin and having a molecular weight of approximately 24 kDa–28 kDa.

This invention further provides an isolated nucleic acid molecule encoding a human aortic protein. In an embodiment, the isolated nucleic acid, cDNA, designated AAAP-CL1, encodes a human aortic protein which is immunoreactive with both AAA-associated immunoglobulin and human kappa immunoglobulin and has a molecular weight of approximately 24 kDa–28 kDa. In another embodiment, the isolated cDNA, designated AAAP-CL5, encodes a human aortic protein which is immunoreactive with both AAA-associated immunoglobulin and human kappa immunoglobulin and has a molecular weight of approximately 24 kDa–28 kDa. In yet another embodiment, the isolated cDNA, designated AAAP-CL4, encodes a human aortic protein which is immunoreactive with both AAA-associated immunoglobulin and human kappa immunoglobulin and has a molecular weight of approximately 24 kDa–28 kDa.

This invention provides a recombinantly produced human aortic protein which is immunoreactive with AAA-associated immunoglobulin. In an embodiment, the protein is of a molecular weight of approximately 40 kDa.

This invention provides a purified recombinant human aortic protein of approximately 24 kDa–28 kDa having the amino acid sequence set forth in SEQ ID NO:2 which is immunoreactive with both AAA-associated immunoglobulin and human kappa immunoglobulin.

This invention provides a purified recombinant human aortic protein of approximately 28 kDa having the amino acid sequence set forth in SEQ ID NO:3 which is immunoreactive with both AAA-associated immunoglobulin and human kappa immunoglobulin.

This invention provides a purified recombinant human aortic protein of approximately 24 kDa–28 kDa having the amino acid sequence set forth in SEQ ID NO:4 which is immunoreactive with both AAA-associated immunoglobulin and human kappa immunoglobulin.

This invention provides an antibody directed to a purified human protein. This invention further provides an antibody capable of specifically recognizing human aortic protein.

This invention provides a method of diagnosing AAA disease in a subject which comprises: (a) obtaining a suitable sample from the subject; (b) contacting the sample with the protein of either the isolated protein of approximately 40 kDa which is purified from human aortic tissue and immunoreactive with AAA-associated immunoglobulin or the isolated protein having the amino acid sequence set forth in SEQ ID NO:1 under conditions permitting the protein to bind to AAA-associated immunoglobulin if present in the sample; and (c)determining the presence of bound protein, the presence of bound protein being indicative of AAA disease, thereby diagnosing AAA disease in the subject.

This invention provides a pharmaceutical composition for alleviating AAA disease in a subject which comprises the protein of approximately 40 kDa which is purified from human aortic tissue and immunoreactive with AAA-associated immunoglobulin and a pharmaceutically acceptable carrier.

This invention provides a method of alleviating AAA disease in a subject which comprises administering to the subject an amount of the aforementioned composition effective to induce tolerance to antigenic AAA protein in the subject.

This invention provides a method of diagnosing AAA disease in a subject which comprises: (a) obtaining a suitable sample from the subject; (b) contacting the sample with the protein selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin under conditions permitting the protein to bind to AAA-associated immunoglobulin if present in the sample; and (c) determining the presence of bound protein, the presence of bound protein being indicative of AAA disease, thereby diagnosing AAA disease in the subject. In an embodiment, the subject may be a mammal, for example a human subject.

This invention provides a pharmaceutical composition for alleviating AAA disease in a subject which comprises the protein is selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin and a pharmaceutically acceptable carrier.

This invention provides a kit for detecting the presence of AAA-associated immunoglobulin in a sample, which comprises: (a) a solid support having a plurality of covalently linked probes which may be the same or different, each probe of which comprises a human aortic protein which is capable of binding AAA-associated immunoglobulin; and (b) a means for determining the presence of AAA-associated immunoglobulin bound to the human aortic protein. In an embodiment of the kit, the human aortic protein is selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin.

This invention provides a kit for detecting the presence of an elevated or abnormal level of human aortic protein in a sample, which comprises:(a) a plurality of covalently linked probes which may be the same or different, each probe of which comprises any one of a AAA-associated immunoglobulin and a human kappa immunoglobulin which is capable of binding human aortic protein; and (b) a means for determining the elevated or abnormal level of human aortic protein bound to AAA-associated immunoglobulin or human kappa immunoglobulin by comparison to a normal level of human aortic protein.

Figure 1:
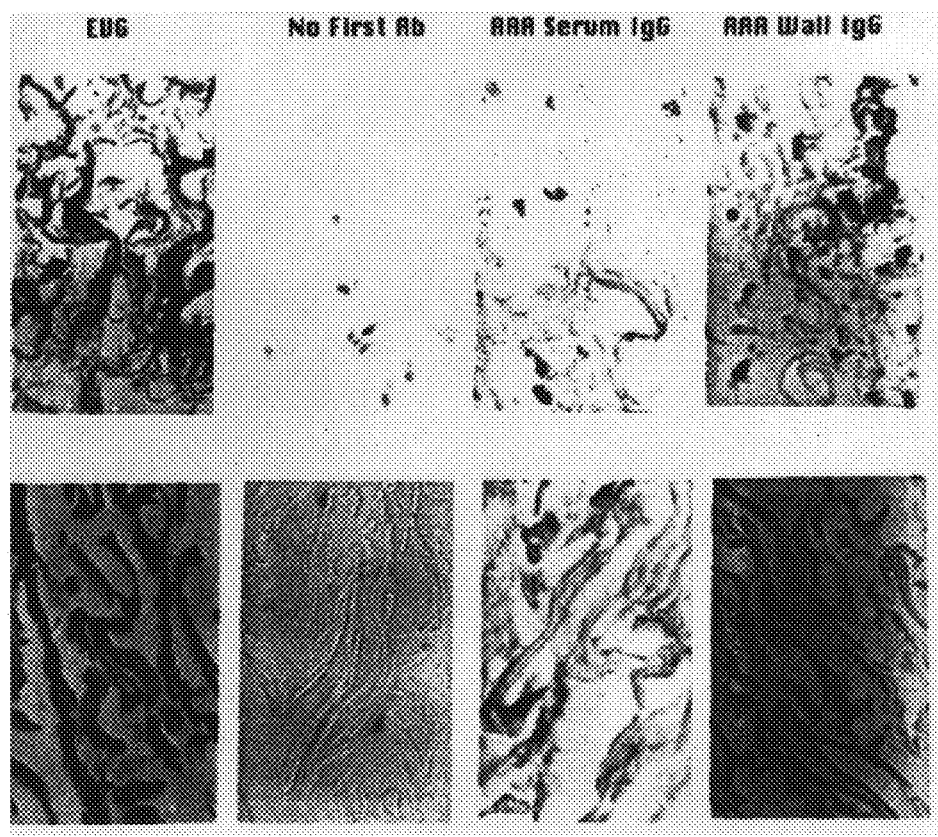
FIG. 1.

Immunoreactive proteins are located surrounding the aortic adventitial elastic fibers in both AAA tissue and normal aortic tissue sections when incubated with IgG from AAA wall or serum. Tissue sections incubated with second antibody alone showed no immunoreactivity.

AAA: abdominal aortic aneurysm tissue section. NL: normal abdominal aortic tissue section. EVG: elastin Von-Gleson stain.

FIG. 2.

Soluble AAA extracts were separated by SDS/PAGE, and then probed first with either IgG from AAA wall or serum, and then with APC rabbit anti-human IgG. Unique immunoreactive binding was observed at 40 kDa (arrow), suggesting the presence of AAAP-40. Second antibody alone was used as control, demonstrating IgGs in the soluble extracts of the aorta.

FIG. 3.

Computer-enhanced Western immunoblot. Soluble AAA extracts were separated by SDS/PAGE, and then probed first with rabbit anti-human vitronectin antibody, and then with APC goat anti-rabbit IgG. Unique immunoreactive material was observed at MW 40 (arrow). Peripheral lymphocytes were harvested, separated by SDS/PAGE, and probed in the same manner. Immunoreactive proteins at MW 75 and 65 kDa, consistent with lymphocyte-bound vitronectin and its degraded form, ware also observed in the aortic extracts.

STD: Standard molecular marker. AAA:AAA PBS tissue extracts. LNC: Lymphocytes.

FIG. 4.

Computer-enhanced glycoprotein detection blot. Soluble AAA extracts and control glycoproteins were separated by SDS/PAGE. Assays for galanthus nivalis agglutinin (GNA), sambucus nigra agglutinin (SNA), maackia amurensis agglutinin (MAA), datura stramonium agglutinin (DSA), and peanut agglutinin (PNA) were undertaken. Control glycoprotein carboxypeptidase Y (CBPXY) reacted with GNA, indicating terminally linked mannose. Control glycoprotein transferrin (TRNSF) reacted with SNA, indicating sialic acid terminally linked alpha (2–6) to galactose or N-acetylgalactosamine. Control glycoprotein fetuin (FETN) reacted with SNA, MAA (indicating sialic acid terminally linked alpha (2–3) to galactose), and DSA (indicating galactose beta (1–4) galactose-beta (1–4)-N-acetylglucosamine). Control glycoprotein asialofetuin (ASFTN) reacted with DSA, and PNA, indicating galactose-beta (1–3)-N-acetylgalactosamine. Several reactive bands were observed in the lanes of AAA extracts, demonstrating the presence of soluble glycoproteins. AAA tissue extracts tested with MAA, DSA and PNA demonstrated positive immunoreactivity at MW 40 kDa. These results indicate that AAAP-40 has carbohydrate moieties including; sialic acid terminally linked alpha (2–3) to galactose, galactose beta (1–3)-N-acetylgalactosamine, and galactose beta (1–4)-N-acetylgalactosamine.

FIG. 5.

Photomicrographs of immunmohistochemical preparations of aneurysmal (AAA) and normal (NL) aortic adventitia, illustrating binding of rabbit anti-human Ig kappa to the elastin-associated microfibril. Control experiments with rabbit anti-human Ig heavy chain as first antibody revealed minimal, if any, immunoreactivity of the microfibril.

FIG. 6.

Transformed cells and control cells (XL) were incubated with IPTG to induce protein expression. After the cells were lysed, the soluble proteins were separated by SDS/PAGE (12.5%) and probed with purified IgGs from AAA patients. AAA serum IgG was uniquely immunoreactive with rAAAP-CL1 and rAAAP-CL5 at approximately 28 kDa, not present in a preparation of the normal bacterial cells.

FIG. 7.

Transformed cells and control cells (XL) were incubated with IPTG to induce protein expression. After the cells were lysed, the soluble proteins were separated by SDS/PAGE (12.5%) and probed with purified serum IgGs from normal patients. No unique immunoreactive material was detected.

FIG. 8.

Transformed cells and control cells (XL) were incubated with IPTG to induce protein expression. After the cells were lysed, the soluble proteins were separated by SDS/PAGE (12.5%) and probed with rabbit anti-human Ig kappa antibody. Unique immunoreactive binding was detected with rAAAP-CL1 and rAAAP-CL5 at approximately 24 kDa, not present in a preparation of the normal bacterial cells.

FIG. 9.

Transformed cells and control cells (XL) were incubated with IPTG to induce protein expression. After the cells were lysed, the soluble proteins were separated by SDS/PAGE (12.5%) and probed with APC goat anti-human heavy chain antibody. No unique immunoreactive binding was detected.

FIGS. 10A–F.

(A) rAAAP-CL1 as modeled by SwissModel, labeled in the standard convention for Ig-folds [19] and displayed by RasMol in "cartoon" mode with yellow coding for beta strands and red coding for alpha coils. There is a short helix between strands e and f.

(B) The molecule, rAAAP-CL1, displayed by RasMol in "group" mode, wherein N-terminal progresses to C-terminal in colors from blue>dark green>light green>yellow>red.

(C) rAAAP-CL1 rotated horizontally 180 degrees to display the back of the bottom beta sheet, in "group" mode.

(D) The first Ig-like domain of VCAM-1 mouse. The c, f, and g strands of the bottom sheet are not present, but the structure has substantial similarity to the front sheet of rAAAP-CL1, including the alpha helix at the end of strand e. This degree of three dimensional structural similarity is interesting, considering that less than 30% of the amino acid residues have been converted (as shown in E)

(E) A Pairwise Comparison of rAAAP-CL1 and VCAM-1 mouse displayed by LALNView.

(F) A Pairwise comparison of rAAAP-CL1 with protein from cytomegalovirus

FIG. 11.

A hypothetical evolutionary tree based on PAM distances calculated by AllAll.

FIG. 12.

Transformed cells (rAAA) and control cells (XL) were incubated with ITPG to induce protein expression. After the cells were lysed, the soluble proteins were separated by SDS/PAGE (12.5%) and probed with purified IgGs from either AAA patients or volunteers. AAA IgG was immunoreactive with a protein at 28 kDa, which was not present in a preparation of the normal bacterial cells.

FIG. 13.

Pair-wise alignment of the amino acid sequence of rAAAP-CL4 (clone 4) with human fibrinogen-beta, microfibril associated protein-4 (MFAP-4) ((26) in 4th series), and microfibril-associated glycoprotein-36 (MAGP-36) ((4) in 4th series).

FIG. 14.

Pair-wise alignment of rAAAP-CL4 (clone 4) with two immunoglobulin kappa sequences that we have reported to resemble clones 1 and 5.((7) in 4th series)

FIG. 15.

Pair-wise alignment of rAAAP-CL4 (clone 4) with a protein from cytomegalovirus ((28) in 4th series) and a protein from influenza ((30) in 4th series).

FIG. 16.

Swiss-Model of the three-dimensional structure of MAT-CAM 2 revealing it to have an immunoglobulin-like sandwich, formed by two antiparallel beta sheets, connected by a helix in the region of the putative binding site.

FIG. 17.

Pair-wise comparison of MAT-CAMs 1 (Clone 1) and 2 (Clone 2), as displayed by LalnView, with color coding for the regions of greatest similarity in amino acid sequence. The three dimensional structures have been conserved despite substantial divergence in sequence.

FIG. 18.

An evolutionary tree, roughly scaled in PAM units (point accepted mutations/100 amino acid residues), as computed by AllAll. For proteins of the fibrinogen family, a PAM unit has been estimated to be about 1.1 million years.[14]

FIG. 19.

Histological section of aneurysmal aorta probed with antibodies against immunoglobulin kappa and against immunoglobulin heavy chain. Anti-Ig kappa localizes to the adventitial elastin-associated fibril.

FIG. 20.

In-situ hybridization of clone 1 against a histological section of normal human aorta. The predominant cell type positive for hybridization in this section is mesenchymal, although further studies would be required to differentiate whether the positive cells are fibroblasts or smooth muscle cells.

FIG. 21.

Tissue samples of AAA and control aortas were sectioned at 6 μm for histochemistry (iron hematoxylin, abbreviated EVG) and immunohistochemistry with rabbit anti-*T pallidum* (*T pall*) and rabbit anti-herpes simplex virus (HSV). The EVG stain shows fibers of elastin in the aortic adventitia. No immunoreactivity is seen with second antibody alone, although the elastin fibers can be faintly recognized by their optical property of birefringence. The anti-*T pall* and anti-herpes antibodies are immunoreactive with the periphery of the elastic fibers, consistent with the elastin-associated microfibril. (Light microscopy, 400×.).

FIG. 22.

Treponema pallidum (Tpall) proteins were separated by SDS/PAGE, transferred to membrane, and then reacted with the following first antibodies: rabbit anti-*T pall*, rabbit anti-herpes simplex (HSV), IgG from a healthy control, and IgG from the wall of an AAA. Second antibody alone (anti-rabbit) was used in a control experiment, and it did not bind to the *T pall* proteins. Rabbit anti-*T pall* antibody demonstrated many immunoreactive proteins as expected, ranging in molecular weight from 19 kDa to 101 kDa. Anti-herpes simplex antibody was also immunoreactive with several *T pall* proteins, ranging from 38 to 80 kDa. Second antibody alone for the human IgG experiments was not immunoreactive. Several faint bands were detectable with control serum, but this weak immunoreactivity may be nonspecific or due to other epitopes that *T pall* may share with other pathogens. AAA wall IgG was conspicuously immunoreactive with several *T pall* proteins, particularly the one at approximately 40 kDa.

DETAILED DESCRIPTION OF THE INVENTION

This invention provides an isolated protein of approximately 40 kDa which is purified from human aortic tissue and immunoreactive with AAA-associated immunoglobulin. In one embodiment, the isolated protein is capable of forming a disulfide-bonded dimer of approximately 80 kDa. In another embodiment, purification of the protein from human aortic tissue comprises extraction of the protein under reducing conditions. In still another embodiment, the isolated protein has the amino acid sequence set forth in SEQ ID NO:1.

As used herein, AAA means "Abdominal Aortic Aneurysm".

This invention provides a recombinantly produced human aortic protein which is immunoreactive with both AAA-associated immunoglobulin and human kappa immunoglobulin and having a molecular weight of approximately 24 kDa–28 kDa.

This invention provides an isolated nucleic acid molecule encoding a human aortic protein. In one embodiment, the isolated nucleic acid molecule is a DNA molecule. In another embodiment, the isolated DNA molecule is a cDNA molecule. In an embodiment, the isolated cDNA, designated AAAP-CL1, encodes a human aortic protein which is immunoreactive with both AAA-associated immunoglobulin and human kappa immunoglobulin and has a molecular weight of approximately 24 kDa–28 kDa. In another embodiment, the isolated cDNA, designated AAAP-CL5, encodes a human aortic protein which is immunoreactive with both AAA-associated immunoglobulin and human kappa immunoglobulin and has a molecular weight of approximately 24 kDa–28 kDa. In yet another embodiment, the isolated cDNA, designated AAAP-CL4, encodes a human aortic protein which is immunoreactive with both AAA-associated immunoglobulin and human kappa immunoglobulin and has a molecular weight of approximately 24 kDa–28 kDa. In an embodiment, the isolated DNA molecule is genomic DNA molecule. In one embodiment, the isolated nucleic acid molecule is an RNA molecule. In an embodiment, the isolated nucleic acid molecule encodes a human aortic protein.

This invention provides a recombinantly produced human aortic protein which is immunoreactive with AAA-associated immunoglobulin. In an embodiment, the protein is of a molecular weight of approximately 40 kDa.

This invention provides a purified recombinant human aortic protein of approximately 24 kDa–28 kDa having the amino acid sequence set forth in SEQ ID NO:2 which is immunoreactive with both AAA-associated immunoglobulin and human kappa immunoglobulin.

This invention provides a purified recombinant human aortic protein of approximately 28 kDa having the amino acid sequence set forth in SEQ ID NO:3 which is immunoreactive with both AAA-associated immunoglobulin and human kappa immunoglobulin.

This invention provides a purified recombinant human aortic protein of approximately 24 kDa–28 kDa having the amino acid sequence set forth in SEQ ID NO:4 which is immunoreactive with both AAA-associated immunoglobulin and human kappa immunoglobulin.

This invention provides an antibody directed to a purified human protein, said protein selected from the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin, other than the AAA-associated immunoglobulin. The aforementioned antibodies may be monoclonal antibodies.

This invention provides an antibody capable of specifically recognizing human aortic protein, said protein selected from the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin, other than the AAA-associated immunoglobulin. The aforementioned antibodies may be monoclonal antibodies. Methods of making antibodies, including monoclonal antibodies, are well known to one of ordinary skill in the art.

This invention further provides a method of diagnosing AAA disease in a subject which comprises: (a) obtaining a suitable sample from the subject; (b) contacting the sample with the isolated protein of the invention under conditions permitting the protein to bind to AAA-associated immunoglobulin if present in the sample; and (c) determining the presence of bound protein, the presence of bound protein being indicative of AAA disease, thereby diagnosing AAA disease in the subject.

This invention provides a method of diagnosing AAA disease in a subject which comprises:(a) obtaining a suitable sample from the subject; (b) contacting the sample with the protein of either the isolated protein of approximately 40 kDa which is purified from human aortic tissue and immunoreactive with AAA-associated immunoglobulin or the isolated protein having the amino acid sequence set forth in SEQ ID NO:1 under conditions permitting the protein to bind to AAA-associated immunoglobulin if present in the sample; and (c)determining the presence of bound protein, the presence of bound protein being indicative of AAA disease, thereby diagnosing AAA disease in the subject.

This invention provides a method of diagnosing AAA disease in a subject which comprises: (a) obtaining a suitable sample from the subject; (b) contacting the sample with the protein selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin under conditions permitting the protein to bind to AAA-associated immunoglobulin if present in the sample; and (c) determining the presence of bound protein, the presence of bound protein being indicative of AAA disease, thereby diagnosing AAA disease in the subject.

Bound protein, i.e. protein bound to AAA-associated immunoglobulin may be detected using methods well known to those of ordinary skill in the art. Examples of method for detection of bound protein are Enzyme Linked Immunosorbant Assays (Elisa) and Radioimmunoassays. Assays for detecting bound protein may also be found in texts well known in the art, such as Harlow, E., and Lane, D., 1988.

As used herein, AAA-associated immunoglobulin is immunoglobulin which is present in a subject afflicted with abdominal aortic aneurysms (AAA), and which is not present in healthy subjects, i.e. subjects which do not currently have AAA.

In the aforementioned methods of the subject invention, the subject may be a mammal, for example, a human.

The subject invention further provides a pharmaceutical composition for alleviating AAA disease in a subject which comprises the aforementioned purified protein of the invention and a pharmaceutically acceptable carrier.

This invention provides a pharmaceutical composition for alleviating AAA disease in a subject which comprises the protein of approximately 40 kDa which is purified from human aortic tissue and immunoreactive with AAA-associated immunoglobulin and a pharmaceutically acceptable carrier.

This invention provides a pharmaceutical composition for alleviating AAA disease in a subject which comprises the protein is selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin and a pharmaceutically acceptable carrier.

As used herein, the term "pharmaceutically acceptable carrier" encompasses any of the standard pharmaceutical carriers. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions. In an embodiment, the pharmaceutical composition is suitable for administering orally to a subject.

This invention further provides a method of alleviating AAA disease in a subject which comprises administering to the subject an amount of any of the aforementioned compositions comprising the invented purified proteins, said amount effective to induce tolerance to antigenic AAA protein in the subject. In the aforementioned methods of alleviating AAA disease in a subject the subject invention, the subject may be a mammal, for example, a human.

As used herein, the term "antigenic AAA protein" means any native protein of human aorta which causes AAA disease.

Tolerance has been induced in humans to specific autoimmune antigen proteins by administering the antigen orally to the human subject. David Trentham, et al. report they have significantly reduced Rheumatoid Arthritis (RA) patients' symptoms by feeding them type II collagen, a protein common in joint cartilage and a possible target of the autoimmune attack in RA (Trentham, D, et al., 1994). Their approach, called oral tolerization, takes advantage of a trick used by the body through the digestive system suppress immune responses to those proteins instead of triggering them. Oral tolerization attempts to reduce autoimmune attacks by feeding the patients proteins—collagen, in this case—that are found at the site of autoimmune disease and that may have triggered the autoimmunity in the first place (Barinaga, M., 1994).

In the aforementioned methods of the subject invention for alleviating AAA disease in a subject, the subject may be a mammal, such as a human.

The subject invention also provides a recombinantly produced human aortic protein which is immunoreactive with AAA-associated immunoglobulin. In one embodiment of the subject invention, the recombinantly produced protein is approximately 40 kDa.

This invention further provides a method of diagnosing AAA disease in a subject which comprises: (a) obtaining a suitable sample from the subject; (b) contacting the sample with the recombinantly produced protein of the subject invention under conditions permitting the protein to bind to AAA-associated immunoglobulin if present in the sample; and (c) determining the presence of bound protein, the presence of bound protein being indicative of AAA disease, thereby diagnosing AAA disease in the subject. Methods of determining the presence of bound protein are well known in the art as discussed above.

In the aforementioned method of the subject invention for diagnosing AAA disease using the recombinantly produced proteins, the subject may be a mammal, for example, a human.

This invention further provides a pharmaceutical composition for alleviating AAA disease in a subject which comprises the recombinantly produced protein of the invention and a pharmaceutically acceptable carrier. The pharmaceutical composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention provides a method of alleviating AAA disease in a subject which comprises administering to the subject an amount of the aforementioned composition comprising the invented recombinantly produced protein, said amount being effective to induce tolerance to antigenic AAA protein in the subject. Said method of alleviating AAA disease in a subject comprises in one embodiment orally administering an oral composition according to the subject invention to the subject. Such administration imparts oral tolerization to the antigenic AAA protein as discussed above to the subject.

In the aforementioned method of the subject invention for alleviating AAA disease in a subject, the subject may be a mammal, such as a human.

Finally, this invention provides a kit for detecting the presence of AAA-associated immunoglobulin in a sample, which comprises: (a) a solid support having a plurality of covalently linked probes which may be the same or different, each probe of which comprises a human aortic protein which is capable of binding AAA-associated immunoglobulin; and (b) a means for determining the presence of AAA-associated immunoglobulin bound to the human aortic protein. In an embodiment of the kit, the human aortic protein is selected from any of the following proteins: the isolated protein of approximately 40 kDa which is purified from human aortic tissue and immunoreactive with AAA-associated immunoglobulin; the isolated protein of approximately 40 kDa which is purified from human aortic tissue and immunoreactive with AAA-associated immunoglobulin having the amino acid sequence set forth in SEQ ID NO:1; a recombinantly produced human aortic protein which is immunoreactive with AAA-associated immunoglobulin; a recombinantly produced human aortic protein which is immunoreactive with AAA-associated immunoglobulin and is of a molecular weight of approximately 40 kDa; a purified recombinant human aortic protein of approximately 24 kDa–28 kDa having the amino acid sequence set forth in SEQ ID NO:2 which is immunoreactive with both AAA-associated immunoglobulin and human kappa immunoglobulin; a purified recombinant human aortic protein of approximately 28 kDa having the amino acid sequence set forth in SEQ ID NO:3 which is immunoreactive with both AAA-associated immunoglobulin and human kappa immunoglobulin; a purified recombinant human aortic protein of approximately 24 kDa–28 kDa having the amino acid sequence set forth in SEQ ID NO:4 which is immunoreactive with both AAA-associated immunoglobulin and human kappa immunoglobulin.

In an embodiment of the kit the means for determining the presence of AAA-associated immunoglobulin bound to the human aortic protein is a suitable detectable label. In another embodiment of the kit, the suitable detectable label is radioactive isotope, enzyme, dye, biotin, a fluorescent label or a chemiluminescent label.

This invention provides a kit for detecting the presence of an elevated or abnormal level of human aortic protein in a sample, which comprises: (a) a plurality of covalently linked probes which may be the same or different, each probe of which comprises any one of a AAA-associated immunoglobulin and a human kappa immunoglobulin which is capable of binding human aortic protein; and (b) a means for determining the elevated or abnormal level of human aortic protein bound to AAA-associated immunoglobulin or human kappa immunoglobulin by comparison to a normal level of human aortic protein. Methods of measuring the levels of proteins in samples from a subject are well known to one of ordinary skill in the art.

This invention will be better understood from the "Experimental Details" section which follows. However, one skilled in the art will readily appreciate that the specific methods and results discussed therein are not intended to limit, and rather merely illustrate, the invention as described more fully in the claims which follow thereafter.

FIRST SERIES OF EXPERIMENTS

EXPERIMENTAL DETAILS

EXAMPLE 1

Human aortic tissue was extracted for microfibrillar proteins according to the method of Prosser, et al.[11] In brief, the tissue was first extracted in a phosphate buffer containing potassium chloride 0.6M. The insoluble pellet was treated with bacterial collagenase in Tris buffer. The final tissue extraction utilized guanidinium chloride 6M in buffer containing dithiothreitol 50 mM and EDTA 2 mM. Gel slices containing the protein of interest were digested with trypsin or Lys-C and amino acid sequences were determined in the Protein Chemistry Core Facility, Howard Hughes Medical Institute, Columbia University (New York, N.Y.).

Results

A 59 residue sequence of AAAP-40 as experimentally determined is shown in Table I. Alignment on MFAP-4 and MAGP-36 (bovine) is shown, along with homologous sequences from the alpha and beta chains of human fibrinogen. Five and 11 residue sequences of AAA-40 are shown in Table II, in alignment with sequences from vitronectin, MFAP-4, MAGP-36, fibrinogen-beta (from its calcium binding domain), and two other calcium binding proteins (myeloid calcium binding protein and bovine aggrecan).

Discussion

Fibrinogen-like domains are well-known in the MAGP's.[8] The sequence of AAA-40 shown in Table I has regions of substantial homology with sequences in the alpha and beta chains of fibrinogen. Another sequence that we have determined (data not shown) matches residues 283–292 in the gamma chain. Since the three fibrinogen chains are believed to have a single ancestral gene, it would appear likely that AAAP-40 is related to the common ancestor since it has motifs that are used in all three fibrinogen subunits.

Kobayashi, et al. noted that MAGP-36 has the property of calcium-binding, although a candidate site for the calcium-binding domain has not been proposed. Kielty and Shuttleworth have observed that incubation of intact microfibrils with EDTA rapidly results in gross disruption of microfibrillar organization, which can be reversed by replacing calcium.[12] Since fibrillin has 43-EGF-like motifs with calcium binding consensus sequences, and calcium has been proposed to orchestrate the assembly of tropoelastin to the microfibril and hold it in register for crosslinking,[13] it is hypothesized herein that the calcium-binding domain of AAAP-40 may play a role in calcium-dependent microfibril assembly in the aorta. When GenBank was searched for homologies of AAAP-40 and MAGP-36, sequences were found in calcium-binding myeloid-related protein (>pir/A44111:# 144–154), the calcium-binding domain of human fibrinogen-beta, and bovine aggrecan (>pir/A39808:# 59–66) that have similarities to MFAP-4, MAGP-36, and AAAP-40. Bold type is used in Table II to highlight residues that appear to be conserved, with possible significance for the calcium-binding function.

Another matrix protein detected in human embryonic tissue (sulfated protein 30 kDa=SP-30) has been reported to be immunoreactive with monoclonal antibodies against human vitronectin,[14] A sequence of AAAP-40 that matches residues #230–240 in human vitronectin is also shown in Table II. Tomasini-Johansson, et al. proposed that SP30 is the human homolog of MAGP-31, but since MAGP-31 does not have a vitronectin-like domain, SP-30 is more likely to be closely related to AAAP-40.

Finally, a brief comment on the nomenclature problem. Perhaps the simplest approach for the present would be to assign the human MAGP's a number in the order of their discovery. Thus, the first would be the principal component of the microfibril, fibrillin.

The second would be the protein of Smith Magenis syndrome, and the third would be the protein described in the present application. MAGP-3 is probably the human homolog of the bovine aortic protein of Kobayashi (MAGP-36), and the human homolog of Gibson's MAGP-31 has yet to be identified. Notwithstanding the proposal of Zhao, et al. to call this family of glycoproteins "MFAP",[9] retention of the abbreviation MAGP is favored, since the first bovine member of this family was so-named by Gibson, et al. ten years ago and the term has been widely used ever since.

TABLE I

This table shows sequence of AAAP-40, as determined experimentally. The sequence of AAAP-40 is aligned along a continuous sequence of MFAP-4, beginning at residue 140. Homologous regions of MAGP-36 (bovine) and fibrinogen alpha (residues 120–132) and beta residues 338–353 (human) are also shown. "( )" is used to designate an ambiguous residue; "." denotes a non-conserved residue; and "I" denotes a tryptic cleavage site.

```
              I    (Y)F P(F)V  D L M V M   A N Q P M    AAAP-40
122 T L K Q K      Y E L R V   D L E D F   E N N T A    MFAP-4
    T L   L K      Y E L R V   D L E D F   E X N T A    MAGP-36
                     L R V     E L E D .   A . N . A    Hum
                                                        Fib-a
    G E I Y Y      D F F       T X G M A   K E Y D G F Q  AAAP-40
142 Y A K Y A      D F S I S   P N A V S   A E E D G    MFAP-4
    F A K Y A      D F S I S   P N A V S   A E E D G    MAGP-36
    Y T X G M      A K(I Y)A   G N A L M   D G A S G L M  AAAP-40
162 Y T L F V      A G F E D   G G A G D   S L S Y H    MFAP-4
    Y T L Y V      S G F E D   G G A G D   S L T Y H    MAGP-36
    Y . I . V      . K   T A   G N A L                  Hum
                                                        Fib-b
```

TABLE II

Alignment of experimentally determined sequences of AAAP-40 on sequences from human vitrronectin (VN, residues 230–240) and MFAP-4 (beginning at residue #34). Alignments with other calcium-binding proteins are shown, with the most highly conserved residues highlighted in bold type: Calcium-binding myeloid-related protein[15] = CBP-M; Aggrecan (bovine)[16] = Aggr; human fibrinogen beta (residues 144–157 from calcium-binding domain) = Fib-b.

```
Q E L E K                        I F E D G V L P D Y P   AAAP-40
                                 R F E D G V L P D Y P   VN
F C L Q Q P L D C D C D D I Y    A Q G Y Q S D G VYL I Y P S   MFAP-4
S E L Q L P L D E D D I Y        A Q G Y Q A D G VYL I   P S   MAGP-36
T E L . . . L . E . D V Y        . . . Y . . D                CaBP-M
            P . D E . D V Y                                    Aggr
S E L E K H Q L . . D . T                                      Fib-b
```

EXAMPLE 2

Methods

Human subjects: Specimens of AAA tissue and peripheral blood were taken from patients at the time of infrarenal AAA repair. Normal abdominal aorta was harvested from organ donors. The protocols for human investigation have been approved by the Institutional Review Board. Specimens were frozen at −110° C. immediately until use in biochemical studies. Serum was extracted from blood, and stored at −20° C. until further studies.

Purification of IgG: Human IgG was purified from aortic tissue and from serum as described previously.[11] Briefly, the tissue was homogenized in salt buffer (2 M NaCl, 50 Mm TrisHCl, pH 7.5, 0.02% Na Azide). The homogenate was then centrifuged at 10,000 g for 1 hour at 4° C. IgG was extracted from the supernatants using protein A-sepharose (Sigma, St. Louis, Mo.) column chromatography, and was eluted with 0.1M citric acid at the following pH; 3.0, 4.5 and 6.5. Each fraction was dialyzed against phosphate-buffered saline (PBS) at pH 7.5. Protein concentration was determined for each sample using dye-binding assays from Bio-Rad Laboratories (Richmond, Calif.).

PBS tissue extraction: Each tissue sample was minced and washed several times in PBS buffer containing 2 mM phenylmethylsulfonyl fluoride (PMSF) and 2 mM Na azide. Then the samples were homogenized in PBS buffer (described above) with 0.5 M ethylenediaminetetraacetic acid (EDTA). The homogenate was centrifuged at 650 g for 20 minutes at 4° C., and then ultrafuged at 20,000 g for 1 hour at 4° C. The protein concentration for each sample was determined by dye-binding methods. The samples were frozen at −20° C. until further experiments.

Microfibril-associated glycoprotein (MAGP) tissue extraction: MAGP from AAA tissue was extracted as described by Prosser et al.[2] Samples were homogenized with buffer containing 0.1 M epilson-amino caproic acid, 2 mMN-ethylmaleimide, 1 mM PMSF, and 0.1% Na azide. First, the samples were extracted in PBS with 0.6 M KCl. Next, the insoluble pellet was treated with bacterial collagenase in Tris buffered saline (TBS). The preparation was then extracted with 6 M guanidine hydrochloride buffer containing 50 mM dithiothretol and 2 mM EDTA.

Lymphocyte harvesting: Human peripheral blood lymphocytes were harvested using Ficoll-Hypaque gradient (Histopaque™, Sigma, St. Louis, Mo.) as per standard protocol.

Immunohistochemistry: Tissue samples were fixed in formalin, embedded in paraffin, and sectioned at 6 um. The sections were deparaffinized in xylene and rehydrated using an ethanol step gradient. Iron-hematoxylin-von Gieson staining was performed using standard protocols. The sections were blocked with 1% bovine serum albumin (Sigma, St. Louis, Mo.). Purified IgG(1:50), as described above, was used as the first antibody. Alkaline phosphate-conjugated (APC) rabbit anti-human IgG (Sigma, St. Louis, Mo.) 1:50 was used as the second antibody. The sections were washed, and then developed with Vectastain BCIP/NBT kit (Vector laboratories, Burlingame, Calif.). After counter staining with Fast Red (Sigma, St. Louis, Mo.), sections were dehydrated and mounted in Permont (Fisher, Pittsburgh, Pa.). Slides were examined by light microscopy.

Modified Gomori Aldehyde Fuchsin-Peracetic Acid Reaction: The basic method for staining microfibrils was described by Fullmer et al.[12] Briefly, the 6 um paraffin-embedded tissue sections ere oxidized in peracetic acid for 15 minutes after deparaffinization. The sections were stained in Gomori's aldehyde fuchsin followed by hematoxylin (Sigma, St. Louis, Mo.). After counter stained with modified Halmis's solution, the sections were dehydrated and mounted.

Western Immunoblotting: Soluble protein in aliquots of PBS tissue extracts and MAGP tissue extracts, and harvested lymphocytes were separated by SDS/PAGE (12.5%), and then electroblotted onto nitrocellulose membranes. The membranes were blocked with 5% dry milk in PES prior to incubating with the first antibody. Either purified AAA wall IgG (1:100), AAA serum IgG (1:100) or rabbit anti-human vitronectin (1:10,000) was used as the first antibody and allowed to incubate overnight at 4° C. After washing the membranes, either PC rabbit anti-human IgG (1:1000) or PC goat anti-rabbit IgG (1:5000) was used as the second antibody. Immunoreactivity was detected by the Vectastain BCIP/NBT color developing system.

Glycoprotein Detection: PBS tissue extracts and standard glycoproteins were separated by SDS/PAGE (12.5%), followed by nitrocellulose membrane transfer as described above. Glycoprotein detection was carried out using DIG™ glycan differentiation kit (Boehringer Mannheim Biochemica, Indianapolis, Ind.). Images of the membranes were digitized, enhanced and printed by computer.

Construction of cDNA Libraries: mRNA from aortic adventitia was reverse transcribed for insertion into the phagemid, Uni Zap XR™)lambda vector system, in collaboration with Stratagene (La Jolla, Calif.). This system accommodates DNA inserts up to 10 kb in length.

Expression of cDNA: The phagemid from Uni-Zap XR vector was transfected into a strain of *E. Coli* (XL1-Blue MRF', Stratagene™). The transfected cells were plated on top agar, and then allow to grow at 45° C. until small plaques were visible (approximately 4 hours). Nitrocellulose membranes, impregnated with 10 mM isopropyl thio-beta-D-galactopyranoside (IPTG), were placed onto the agar, and were allowed to incubate for 4 hours at 37° C. The membranes were removed and blocked with 5% milk in TBS fro 45 minutes. Incubation was continued with rabbit anti-human vitronectin antibody (1:10,000) for 3 hours at room temperature. The membranes were washed in TBS, and incubated with APC goat anti-rabbit IgG (1:5000) for 2 hours at room temperature. Following a series of washes in TBS, the membranes were developed by Vectastain NBT/BICP color reagent system. The positive plaques were rescreened to obtain pure clones.

RNA was purified from a specimen of human aortic adventitia and reverse transcribed for insertion into the phagmid UniZap XR (Strategene™). A strain of *E. Coli*, engineered for expression (XL1-Blue MRF—Stratagene™, was transfected. Human AAA wall and serum IgG's were used to localize the autoantigen immuno-histochemically, and the Gomori aldehyde fuchasin-peracetic acid reaction was used to evaluate co-distribution with the elastin-associated microfibril. A glycan differentiation kit was used to determine whether AAAP-40 is a glycoprotein.

Results

Tissue sections incubated with AAA wall and serum IgGs showed immunoreactive material co-localizing with elastin-associated microfibrils, surrounding the birefrengent elastic fibers in the aortic adventitia (FIG. 1). Localization of elastin-associated microfibrils was confirmed by the modified Gomori reaction (Data not shown).

Figure 2:
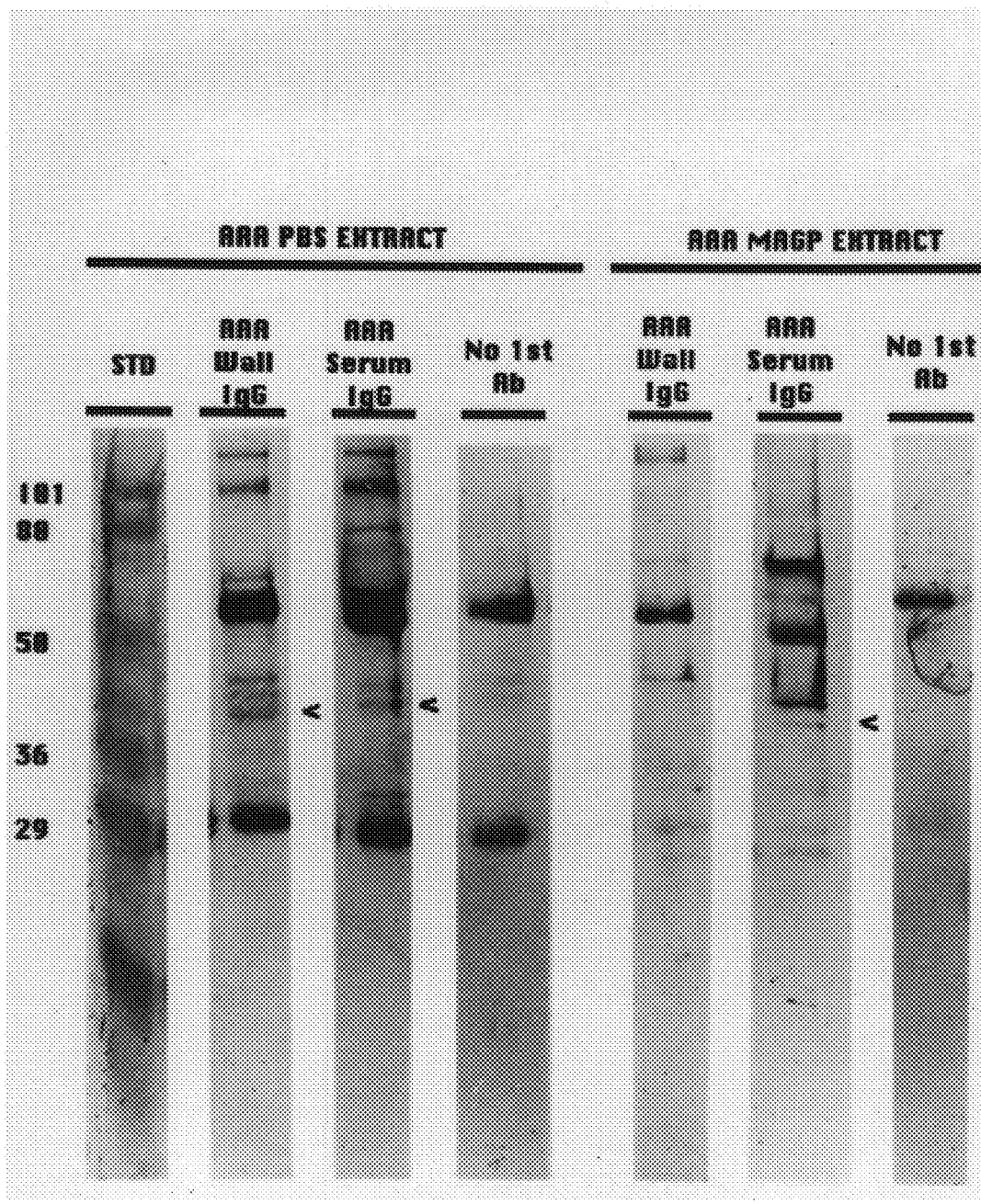
Figure 3:
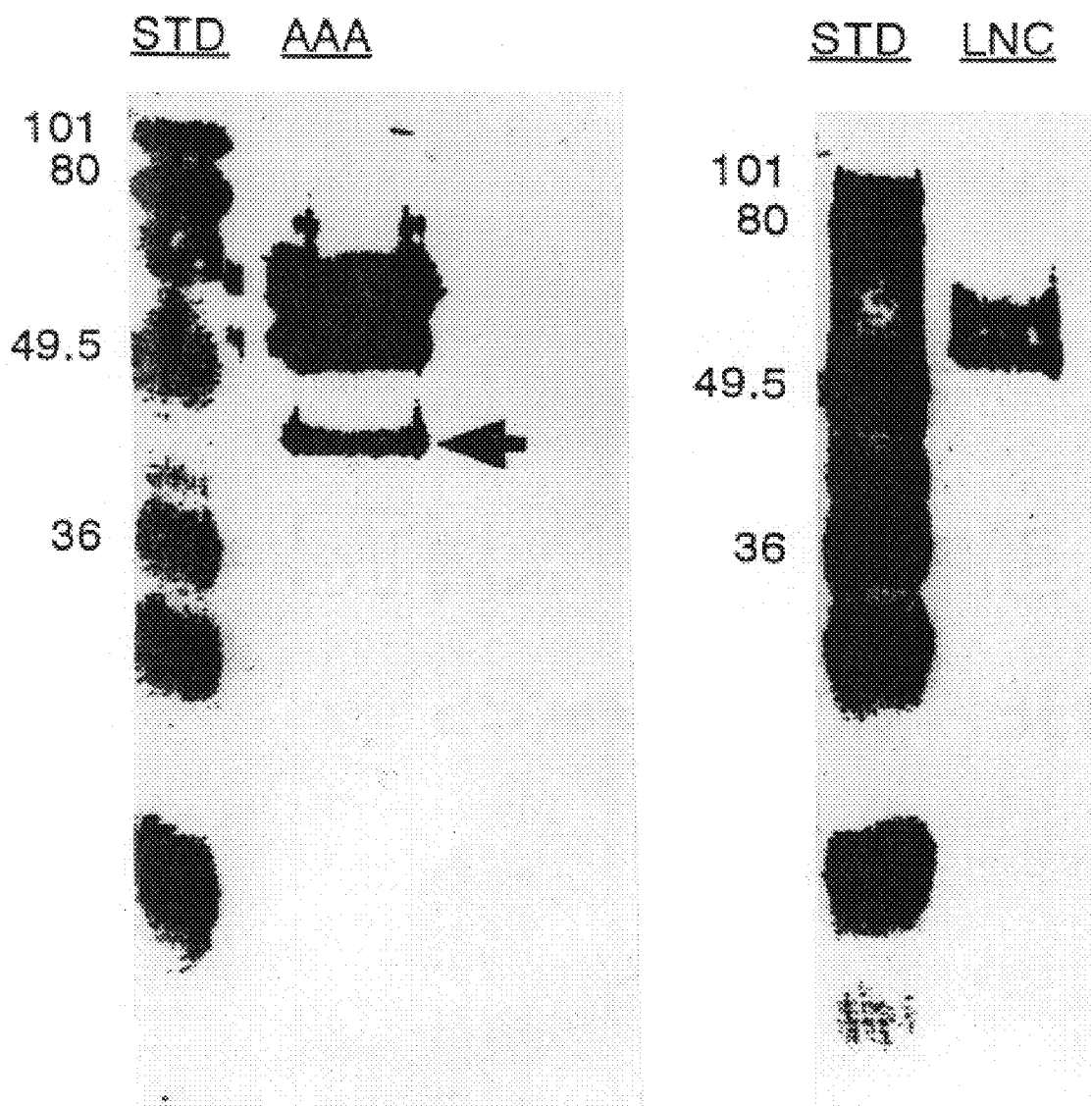

Western immunoblotting showed immunoreactivity of IgGs from AAA wall and serum with soluble aortic matrix proteins (FIG. 2). Unique immunoreactive bands were detected in both AAA PBS and MAGP tissue extracts at MW 40 kDa. Rabbit anti-vetronectin antibody showed unique immunoreactivity at MW 40 when incubated with AAA PBS tissue extracts (FIG. 3).

Figure 4:
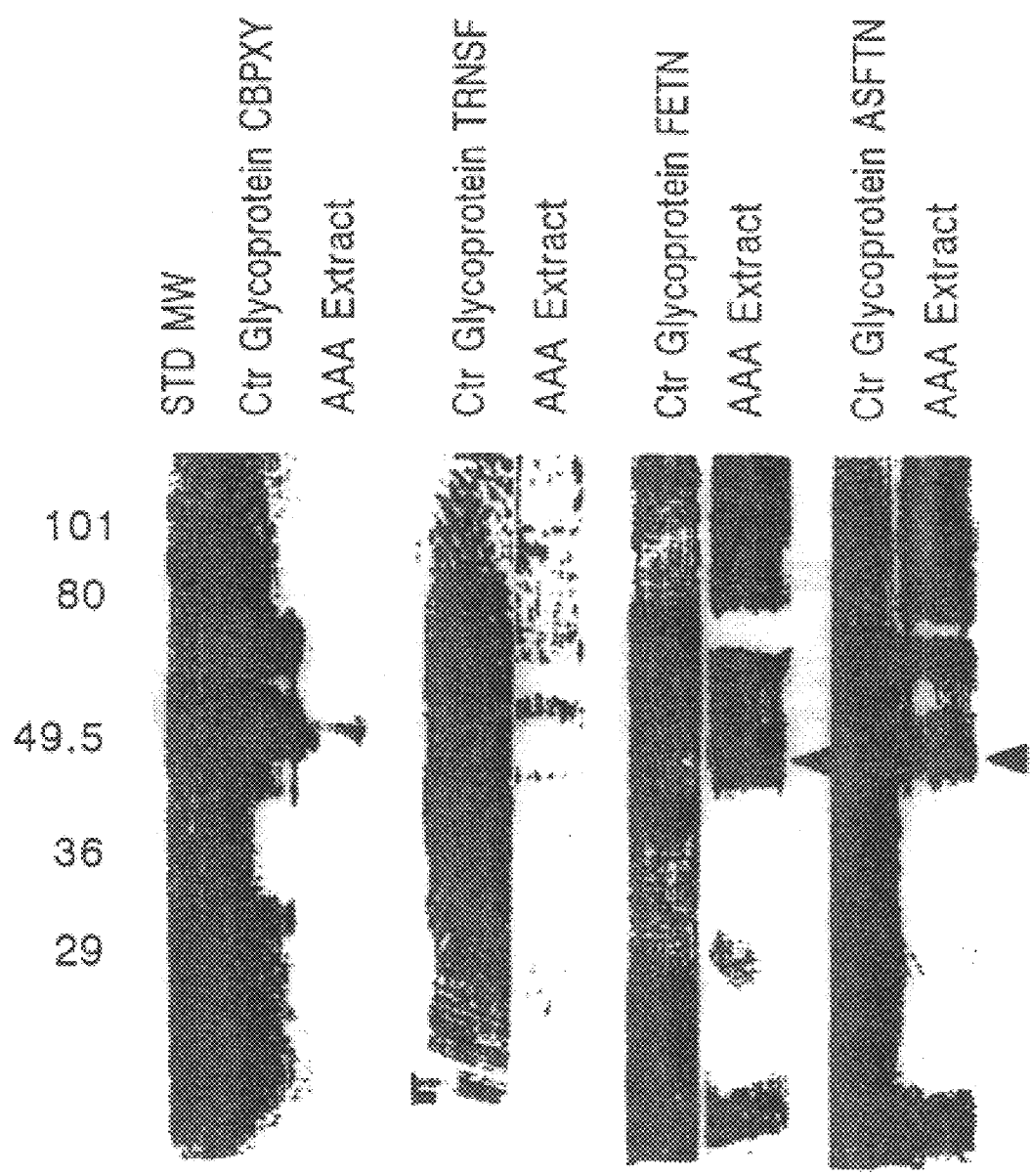

The glycan detection kit confirmed the presence of glycoprotein in AAA PBS tissue extracts at multiple molecular weights, including 40 kDa (FIG. 4). The 40 kDA band (AAA-40) had negative reactions to galanthus nivalis agglutinin (GNA) and sambucus nigra agglutinin (SNA), and positive reactions to maackia amurensis agglutinin (MAA), peanut agglutinin (PNA), and datura stramonium agglutinin (DSA).

Positive expression of AAAP-40 was detected by antibody screening. Estimated frequency of the positive clones was 1:10,000 on primary screening and 1:1000 on secondary screening.

Discussion

Chronic inflammatory cell invasion has been noted in AAA wall.[13,14,15,16] Tumor necrosis factor-alpha, interleukin (IL)-1 beta, IL-6, and IL-8 have been shown to be elevated in AAA tissue extracts when compared to control aortic tissue extracts.[17,18,19] Elevated amounts of matrix-degrading enzymes have also been found in AAA wall associated with mononuclear cell infiltration.[20,21,22] These observations suggest that an autoimmune disease process plays a role in the pathogenesis of AAA.[13,14,17,23,24,25]

It has been reported that IgG from the aortic wall of patients with abdominal aortic aneurysms (AAA) is immunoreactive with a human aortic protein (MW-80 kDa) that has features of the bovine aortic protein of Kobayashi et al. (MAGP-36).[8] Since MAGP-36 occurs in nature as a disulfide dimer, the putative 80 kDa protein in aortic matrix may exist as the dimeric form of AAAP-40.

The present studies demonstrate co-localization of AAAP-40. Glycan differentiation analysis based on the findings shown in FIG. 4, suggests AAAP-40 is a glycoprotein containing the following carbohydrates moieties; sialic acid terminally linked alpha (2–3) to galactose, galactose beta (1–3)-N-acetylgalactosamine, and galactose beta (1–4)-N-acetyl galactosamine.

It is well known that human vitronectin is produced by the liver, and chat circulating vitronectin has MW 75 kDa.[26] The cleavage products are MW 65 and 10 kDa. AAA tissue extracts have unique immunoreactivity with rabbit anti-human vitronectin antibody at MW 40 kDa. Thus, clones positive for reactivity with anti-human vitronectin antibody (in the cDNA expression library) are expressing AAAP-40 protein. The cDNA sequence of AAAP-40 will be further investigated using the positive recombinants.

These present findings have diagnostic and therapeutic implications. Screening tests could be developed to identify circulating autobodies in the peripheral blood from AAA patients. AAA disease progression could be followed by peripheral blood antibody titers. Tolerance to the autoantigen may be induced in the AAA patient, and the further progression of AAA disease may be prevented.

FIRST SERIES OF EXPERIMENTS

REFERENCES

1. Greenlee T K, Jr., Ross R., Hartman J L. The fine structure of elastic fibers. J. Cell Biol 1966; 30; 59–71.

2. Prosser I W, Gibson M A, Cleary E G. Microfibrillar protein from elastic tissue: a critical evaluation. Aust. J. Exp. Bio. Sci. 1984; 62: 485–505.
3. Gibson M A, Huges J L, Fanning J C, Cleary E G (1986). The major antigen of elastin-associated microfibrils is a 31 kDa glycoprotein. J Biol Chem 261: 11429–11436.
4. Gibson M A, Sandberg L B, Grosso L E, Cleary E G (1991) Complementary DNA cloning establishes microfibril-associated glycoprotein (MAGP) to be discrete component of the elastin-associated microfibrils. J Biol Chem 266: 7596–601.
5. Bashir M M, Abrams W R, Rosenbloom J, Kucich U, Bacarra M, Han M-D, Brown-Augsberger P, Mecham R, Rosenbloom J (1994) Microfibril-associated glycoprotein: characterization of the bovine gene and of the recombinantly expressed protein. Biochemistry 33: 593–600.
6. Kobayashi R, Mizutani A, Hidaka H (1994) Isolation and characterization of a 36-kDa microfibril-associated glycoprotein by the newly synthesized isoquinolinesulfonamide affinity chromatography. Biochem Biophys Res Communic 198: 1262–6.
7. Zhao A, Lee C-C, Jiralerspong S, Juyal R C, Lu F, Baldini A, Greenberg F, Caskey C T, Patel P I (1995) The gene for a human microfibril-associated glycoprotein is commonly deleted in Smith-Magenis syndrome patients. Human Mol Genetics 4: 589–597.
8. Tilson M D (1995). Similarities of an autoantigen in aneurysmal disease of the human abdominal aorta to a 36-kDa microfibril-associated bovine aortic glycoprotein. Biochem Biophys Res Communications 213: 40–43.
9. Xia S., Ozsvath K., Hirose H. Tilson M D. Partial Amino Acid Sequence Of A Notice 40 kDa Human Aortic Protein, with Vitronectin-like, Fibrinogen-like, and Calcium binding Domains: Aortic Aneurysm Associated-Protein-40 (AAAP-40) Human MAGP-3), Proposed. Biochem Biophys Res Commun in press.
10. Tomasini-Johansson B R, Ruoslahti E, Pierschbacher M D 91993). A 30 kDa sulfated extracellular matrix protein immunologically crossreactive with vitronectin. Matrix 13: 203–214.
11. Gregory A K, Yin N X, Capella J., Xia S., Newman K M, Tilson M D. Feature of autoimmunity in the abdominal aortic aneurysm. Arch Surg. 1996: 23–25.
12. Fullmer H M, Lillie R D. The oxytalan fiber. A previously undescribed connective tissue fiber. J. Hisochem Cytochem 1958; 6: 425
13. Brophy C M, Reilly J M, Smith G J W, Tilson M D. The role of inflammation in nonspecific abdominal aortic aneurysm disease. Ann Vasc Surg 1991; 5:229.
14. Koch A E, Haines G K, Rizzo R J, et al. Human abdominal aortic aneurysms: Immunophenotypic analysis suggesting an immune mediated response. Am J Pathol 1990; 137: 1199–1219.
15. Beckman E N. Plasma cell infiltrates in athrosclerotic abdominal aortic aneurysm. Am J Clin Path 1986; 85:21–24
16. Rizzo R J, McCarthy W J, Dixit S N, et al. Typing of collagen and content of matrix protein in human abdominal aortic aneurysms. J Vasc Surg 1989; 10: 365–373.
17. Newman K M, Jean-Claude J, Li H, Ramey W G, Tilson M D. Cytokines that activate proteolysis are increased in abdominal aortic aneurysms. Circulation 1994; 90: II-224–II-227.
18. Szekanecz Z, Shar M R, Pearce W H, Koch A E. Human atherosclerotic abdominal aortic aneurysms produce interleukin (IL)-6 and interferon-gamma but not IL-2 and IL-4; the possible role IL-6 interferon-gamma in vascular inflammation. Agents & Actions 1994; 42:159–162
19. Koch A E, Kunkei S L, Pearch W H, et al. Enhanced production of the chemotactic cytokines interleukin-8 and monocyte chemoattractant protein-l in human abdominal aortic aneurysms. Am J Path 1993; 142: 1423–1431.
20. Newman K M, Malon A M, Shin R D, et al. Matrix metalloproteinases in abdominal aortic aneurysm: Characterization, purification and their possible sources. Connective Tissue Res 1994; 30: 265–276
21. Newman K M, Jean-Clause J, Li H, Scholes J V, Ogata Y. Nagase H, Tilson, M D. Cellular localization of matrix metalloproteinases in the abdominal aortic aneurysm wall. J. Vasc. Surg 1994; 20: 814–820
22. Thompson R W, Holmes D R, Mertens R A, et al. Production and localization of 92 kilodalton gelatinase abdominal aortic aneurysms. An elastolytic metalloproteinase expressed by aneurysm-infiltrating macrophages. J Clin Invest 1995; 96: 318–326
23. Pearce E H, Sweis I, Yao JUST, McCarthy W J. Interleukin-lbeta and tumor necrosis factor-alpha release in normal and diseased human infrarenal aortas. J Vasc Surg 1992; 16: 784–789.
24. Jean Claude J, Newman K M, Li H, Gregory A K, Tilson, M D. Possible key role for plasmin in the pathogenesis of a abdominal aortic aneurysms. Surg 1994; 116: 472–475.
25. Reilly J M, Sicard G A, Lucore C L. Abnormal expression of plasminogen activators in aortic aneurysmal and occlusive disease. J. Vasc Surg 1994; 19: 865–872
26. Preissner K T, Jenne D. Structure of vitronectin and its biological role in haemostasis. Thrombosis and Haemostasis 1991; 66: 123–132

SECOND SERIES OF EXPERIMENTS

EXPERIMENTAL DETAILS

The partial amino acid sequence of a human microfibrillar glycoprotein ~40 kDa, which is called Aortic Aneurysm-associated Antigenic Protein-40 kDa (AAAP-40) has been reported. (1) It has sequence homologies with vitronectin (VN) and fibrinogen (FB). A cDNA library was prepared from mRNA purified from human aortic adventitia. Since VN and FB are not synthesized in aorta, the library was screened with polyclonal antibodies to VN and FB. The hypothetical proteins of clones 1 and 5 share a novel domain structure and are the subject of this communication.

Methods mRNA from aortic adventitia was reverse transcribed and inserted into the phagemid, Uni Zap XR™ lambda, by arrangement with Stratagene (La Jolla, Calif.). The phagemid was transfected into *E Coli* (XL1-Blue MRF|, Stratagene™). The cells were plated on top agar and grown at 42° C. until small plaques were visible. Nitrocellulose membranes impregnanted with 10 mM isopropyl thio-beta-D-galactopyranoside were placed on the agar and incubated for 6 hours at 37° C. The membranes were removed and blocked with 5% milk in TBS for 45 minutes. Incubation was continued with either rabbit anti-human vitronectin (Sigma™, St. Louis, Mo.) (1:10,000) or fibrinogen antibody (Sigma™ 1:2,500) for 2 hours at room temperature. The membranes were washed in TBS and incubated with alkaline-phosphatase-conjugated goat anti-rabbit IgG (1:5000) (Sigma™) for 2 hours at room temperature. Following a series of washes in TBS, the membranes were developed by the Vectastain NBT/BICP color reagent system. The positive plaques were rescreened to obtain pure clones.

Excision from positive clones was carried out using the Ex Assist/SOLR System (strategene™).The phages were extracted and re-transfected to SOLR cells with amplified Ex Assist Helper Phage (Strategene™). These cells were grown overnight at 37° C., on ampicillin-supplemented medium, which inhibits the growth of non-transfected cells. The cells were then harvested and lysed by alkali buffer, and the DNA was purified by phenol-chloroform extraction. DNA sequencing was carried out by the core laboratories at Columbia College of Physicians and Surgeons, Columbia University, NY, N.Y.

Immunohistochemistry was performed with rabbit anti-human Ig kappa, 1:50, (Sigma™) and APC goat anti-rabbit IgG, 1:50, whole molecule, (Sigma™). APC goat anti-human Ig heavy chain (FC specific, Sigma™), 1:150, was used for control experiments. The slides were developed with BCIP-NBT kit (Biomeda, Foster city, Calif.) and counterstained with Fast Red (Sigma™).

Results

The proteins encoded by clones 1 and 5 have similar features and domain structures, which can be aligned in eight regions beginning with the N-terminus (Tables III and IV). Region 1 is a lengthy sequence highly homologous to Ig kappa V (88–120 residues). Region 2 is a 44–63 residue sequence, which in the case of clone 5 has a six residue sequence that also occurs in cytomegalovirus. Region 3 is a 9–12 residue sequence that is conserved from Ig-kappa. Region 4 is a possible calcium-binding motif in clone 1, while clone 5 has a gly/pro rich sequence. Region 5 is an aromatic-rich sequence. Region 6 is a gly/pro rich sequence in both clones. Region 7 returns to a conserved sequence from Ig kappa, which in clone 1 contains an RGE motif. Region 8 is a C-terminal sequence of 68–70 residues containing a second aromatic motif.

Immunohistochemistry revealed binding of rabbit anti-human Ig kappa antibody to the aortic adventital microfibril, in specimens of both normal and aneurysmal human abdominal aorta.

Discussion

Two of five clones, selected from an expression library of aortic adventitia, encode unique proteins sharing sequences of Ig kappa, gly/pro rich (collagenous) motifs, and aromatic motifs that occur in several proteins of the extracellular matrix. Both proteins have a similar domain structure with at least 8 regions: 1) Ig kappa (84–120 residues in length); 2) ser/thr-rich motif (44–63); 3) a second Ig kappa motif (9–12); 4) either a possible calcium-binding motif or a gly/pro rich sequence (35–43); 5) an aromatic rich sequence (6–7); 6) another gly/pro rich sequence (62–72); 7) a third Ig kappa sequence (26–28); and 8) a C-terminal 68–70 residue sequence with another aromatic motif.

These are novel proteins. The use of an immunoglobulin domain as a specificity determinant has been described in the fibroblast growth factor receptor, (2) but the use of Ig kappa sequences in matrix proteins has not been described. The gly/pro rich sequences are typical of the collagens. The aromatic motifs resemble similar motifs in vitronectin (VN: FFFS), microfibril-associated protein 4 (3) (MFAP-4: FYYS), and AAAP-40 (FFYS and YY.FFQYT).(1)

GenBank searches have led to the conclusion that aromatic motifs, followed by SP, TS, or L, are rare in structural mammalian proteins, except for the above-mentioned. FFFSP occurs in cytomegalovirus (CMV)(4), as does the sequence CRIKN.AV in clone 5, consistent with the hypothesis that the clinical association of aneurysm disease and infection with CMV (5) may be on the basis of molecular mimicry.(6) FFFL is limited to a human T-cell receptor, a secretory product in mouse, and herpes virus 2 @ residue 62. The herpes virus is interesting, because it is another potential molecular mimic.(6, 7) FFTS is reported only in one other protein, lens fiber major protein.(8) Another interesting feature of clone 1 is the possible calcium-binding sequence. The importance of calcium in the self-assembly of the microfibril has been documented, (9) and we have previously reported a possible calcium-binding motif in AAAP-40.(1) MAGP-36 is also a calcium-binding microfibrillar protein, with tissue distribution limited to the aorta in pig.(10)

Because of these unique features, we suggest the name "kappafibs" for these hypothetical proteins, to reflect their use of Ig kappa motifs and their possible role as structural elements of the microfibril.

TABLE III

Clone 1. Amino acid sequence of the hypothetical protein encoded by clone 1. "*" = cystein residue used in disulfide bond of Ig kappa, present (along with the following R.SQ) in both clones. "X" = indeterminant residue.

```
                                   *
MDMRVPAQLLGLLLLWLPGARCDIQLTQSPSLLSASVGDRVMITCRASQA          50-clone 1
MDMRVPAQLLGLLLLWLPGARCAIRIAQSPSSLSASTGDRVTITCRASQG          Ig-k (11)
<<--First Igk homology region begins at #1---------
..........LLLWI.GA..DI..TQSP.L..VS.GERATINCRSSQ             clone 5
         LLAL.LL.L                                          MFAP - 4
ISSFLAWYQQKPGKAPKLLIHAASSLQTGVPSGSGSGTXFTLTISxl             100-clone
1
ISNYLAWYQQKPGQAPRLLIYDASSRATGIPDRFSGSGSGTDFTLTISRL          Ig-k (12)
------First Igk homology region continues---------
QSEXLQLYYCQHLKGYPITFRPRDTXGXXXNCXCTIXSSSSRHLXNIEIW          150-clone 1
EPEDFAVYYGQQYGSSPLTFGGGTKVEIKRTVAAPSVFIFPPSDEQLK--          Ig kappa
-First Igk ends---->    (aspargine/ser/thr rich)
                                  --->13<---
XCLCCXACYXITSXPKKAKFHWKVDNPSNRVTPQKNFPXQKVFENFGQGKXG        202-clone1
SGTASVVGLLNNFYPREAKVQWKVDNALQSGNSQESVT-------------         Ig kappa
         <2nd conserved Igk         RIFENY.KGRKG            CaBnd(14)
          motif in clone 1>         K.YD..G.GQ              CaBnd(15)
                                    KV.E.F..G               CaBnd(16)
                                    KLYE.FED                CaBnd(17)
    XKGXGXXXXFFFXPFGXXXXFGXXCXCWXPGXXKEFXXPGGAKVQGEG        250-clone 1
```

TABLE III-continued

Clone 1. Amino acid sequence of the
hypothetical protein encoded by clone 1. "*" = cystein
residue used in disulfide bond of Ig kappa, present
(along with the following R.SQ) in both clones. "X" =
indeterminant residue.

```
--Ig K continues directly from VT above to EQ below--
     First Aromatic              Gly/Pro rich
         Motif                      Motif
GKXLPIGXFPXECXQSXTARTALTASAAPTRKHKVYAKEVTHQGL--PVTKSXNRGE        307-c1
--------EQDSKDSTYSLSSTLTLSKADYEKHKVYAGEVTHQGLSSPVTKSFNRGE        IgKappa
                        <3rd conserved Igk motif>
                            S.ADY...K                            AAAP80
                                                                 RGD VN
CXXREKCPHLXXSSSLTPSHPLAXXDPFSTGDLPLLRSSSXFFTSPPSSS               357-clone 1
                        <2nd Aromatic motif
                         also ser/thr rich>
         SSSL           FST.D                                    MFAP-4
                        TST.D                                    AAAP-80
                        STGDIPML...S                             FGF-R(18)
                          FST   VPL.RT                           Heparinβ(19)
                        TSTAD                                    Fib-β (20)
                                    FFFSP                        Ctyomeg
                                    FFFS                         VN
                                    FFYS                         AAAP-40
LAXIFALIMLMLEENEXIK     372# <end of clone 1>
```

TABLE IV

Clone 5. Amino acid sequence of hypothetical
protein of clone 5.

```
                               *
MVLQTQVFISLLLWISGANGDIVMTQSPDSLGVSLGERATINCRSSQRL               49 Clone 5
MVLQTQVFISLLLWISGA+GDIVMTQSPDSLAVSLGERATINCKSSQSV               IgK V-IV (21)
<<--First Igk homology region begins at #1-------
         LL.L.V          DSL V.L                                MFAP-4
FFGSNSKNYLAWYQQKPGQSPKLLIYWASTRDSGVLTDSLAAGLGXI                 96 Clone 5
LYSSNNKNYLAWYQQKPGQAPRLLIYDASSRATGIPDRFSGSGSGTD                 Ig kappa
----------First Igk motif ends---->
SLSPSXXCRLKNLAILXLSAIIIISXXTFRPWGTXLXIQXKCWXAXIFXSF             147 -∩Clone 5
FTLTISRLEPEDFAVYYGQQYGSSPLTFGGGTKVEIKRTVAA----PSVFI             Ig kappa
SISP                                                            MAGP-36
SISP                    LLLLS                                   MFAP-4
     CRIKN.AV                                                   Cytomeg
FPPXEKQFK-<----Fisrt gly/pro rich motif(22)------>              218 Clone 5
FPPSDEQLK---------(joins EI below)----------------              Ig kappa
<2nd Igk
 Motif>
FFFFSPFLXGWXLGXLFXGPXEKIFFPXGPKKRGRGXKXPPNWGKSPSG               268 Clone5
-----------------EITASVVGLLNNFYPREAKVQWKVDNALQSG                Ig kappa
 <1st
aromatic  <-----Second gly/pro rich region begins->
motif>
 FFFSP                                                          Cytomegaly V
 FYYS                                                           AAAP-40
 FYYS                                                           MFAP-4
 FFFS                                                           Vitronectin
 FFF.PF                                                         Clone 1
XXXGRGXQGNLKALWXEPXRLGKGGIRGXNKXXAXEVTHSGLSFAXSKKXXQGRX         Clone 5
NSQESVTEQDSKDSTYSLSSTLTLSKADYEKHKVYAGEVTHQGLSSPVTKSFNRGEG       Ig k
   -G/P motif               <3rd Igk Homology region>
ENDS ------>            A.AA...K.KVYA.EVTH.GL....S....E         Clone 1
LEGEVPPPVXXXQPDPLPSFGLXPFFHRCXTPIXVXQXIFYXTPLXXLGFNYXNVXXXXINKVXFL
                <? 2nd  aromatic motif>        <end of clone 5>
                                                       #393
```

SECOND SERIES OF EXPERIMENTS

REFERENCES

1. Xia S, Ozvath K, Hirose H, Tilson M D. Partial amino acid sequence of a novel 40 kDa human aortic protein, with vitronectin-like, fibrinogen-like, and calcium binding domains: aortic aneurysm-associated protein-40 (AAAP-40) [Human MAGP-3, proposed]. Biochem Biophys Research Communications, 1996; 219: 26–39.
2. Zimmer Y, Givol D, Yayuon A. Multiple structural elements determine ligand binding of fibroblast growth factgor receptors: evidence that both Ig domain 2 and 3 define receptor specificity. J Biol Chem 1993; 268: 7899–7903.
3. Zhao Z, Lee C-C, Jiralerspong S, Juyal R C, Lu F, Baldini A, Greenberg F, Caskey C T, Patel P I. The gene for a human microfibril-associated glycoprotein is commonly deleted in Smith-Magenis syndrome patients. Human Mol Genetics 1995; 4: 589–597.
4. Cytomegalovirus >sp¦P09727¦US11__HCMVA.
5. Tanaka S, Komori K, Okadome K, Sugimachi K, Mori R. Detection of active cytomegalovirus infection in inflammatory aortic aneurysms with RNA polymerase chain reaction. J Vasc Surg 1994; 20: 235–43.
6. Ozsvath K J, Hirose H, Xia S, Tilson M D. Molecular mimicry in human aortic aneurysm diseases. New York Academy of Science Conference Abstract Book: The Abdominal Aortic Aneurysm—Genetics, Pathophysiology, and Molecular Biology 1996 (March 7–9): p28.
7. DePalma R G, Sidaway A N, Giordana J M. Associated aetiological and atherosclerotic risk factors in abdominal aneurysms. in: *The Cause and Management of Aneurysms*, ed. R M Greenhalgh, J A Mannick, J T Powell. WB Saunders Company, London 1990; 97–104.
8. Human lens major protein, >pir¦A22444
9. Kielty C M, Shuttleworth C A (1993). The role of calcium in the organization of the fibrillin microfibrils. FEBS 336: 323–326.
10. Kobayashi R, Tashima Y, Masuda H. Shozawa T. Numata Y, Miyauchi K, Hayakawa T. Isolation and characterization of a new 36-kDa microfibril-associated glycoprotein from porcine aorta. J Biol Chem 1989; 264: 17437–44.
11. Ig kappa, X72444, is the best match with the hypothetical protein encoded by the first 50 exons.
12. Ig kappa, pir>A23746=Ig kappa chain V-III.
13. Intervening sequence uncertain, since forward and reverse sequences of the clone do not overlap.
14. Calcium-binding motif from 25 K calcium-binding protein—Tetrahymena thermophila >gi¦161744.
15. Calcium binding protein—10 kDa—CB25__TETTH >sp¦P09226
16. 55 kDa Calcium binding protein (spinach), residues 1–3 and 6–11, sp¦P31806
17. Calmodulin domain, >gnl¦PID¦e237260.
18. Fibroblast growth factor receptor 2b, rat, >gi¦551272
19. Heparin-binding protein, 46 K—bovine: >pir¦¦S09032.
20. Fibrinopeptide B FIBB__VULVU >sp¦P14482
21. A01902 <pir>=Ig kappa chain V-IV region, best match with first 50 residues of clone 5.
22. The following 62 residues in clone 5 had many ambiguities, but of the 41 that were determined, 15 (36%) were either pro or gly. Thus, this region is similar to the gly/pro rich motif in clone 1.

THIRD SERIES OF EXPERIMENTS

Immunoglobulins (IgGs) isolated from serum and aortic wall of patients with abdominal aortic aneurysms (AAAs) are immunoreactive with a 40 kDA aortic protein, which have been purified and partially sequenced: Aortic Aneurysm-associated Antigenic Protein-40 (AAAP-40) [1,2,3,4]. It has sequence similarities to a protein with tissue distribution limited to the aorta in pig: Microfibril-Associated Glycoprotein 36 kDa (MAGP-36). [2,5,6,7] Fibrinogen, vitronectin, and Ig kappa share sequence similarities with AAAP-40 [8,9]. Pathogens associated with aneurysmal disease, including herpes simplex virus and cytomegalovirus [10], also have sequence similarities with AAAP-40. These viruses have been implicated in the pathogenesis of AAA disease by molecular mimicry [11,12,13].

A cDNA library of mRNA from the aortic wall of a AAA patient was screened with rabbit anti-human vitronectin, yielding five positive clones. Two clones (Clone 1 and Clone 5) have been found to encode unique by hypothetical microfibrillar proteins (rAAAP-CL1 and rAAAP-CL5), with similar domain structure, including three motifs from Ig kappa (hence, "Kappafibs"). [6,14]. It has been shown in immunohistochemical studies that both rabbit anti-human IgG kappa and AAA IgG are immunoreactive with proteins that co-distribute with aortic adventitial fibrils [1,6]. It is here reported that an expression vector transfected with Clone 1 and Clone 5 synthesizes the recombinant proteins, rAAAP-CL1 and rAAAP-CL5, (detectable with AAA IgGs and rabbit anti-human Ig kappa antibody), and these gene products are further characterized (including their tertiary structure and evolutionary origins), and it is proposed that the kappafibs may represent a novel family of matrix cell adhesion proteins (MAT-CAMS).

Methods

Human subjects: At the time infrarenal AAA repair, tissue samples and blood samples were obtained from patients. Normal abdominal aortic tissue was harvested from organ donors. The protocols for human investigation have been approved by the Institutional Review Board.

Purification of IgG: Human IgG was purified from aortic tissue and peripheral blood samples as previously described.[1]

Construction of cDNA libraries: mRNA from AAA adventitia was reverse transcribed for insertion into the phagemid, Uni Zap XR™ lambda vector system, by Stratagene™ (La Jolla, Calif.). DNA inserts up to 10 kb in length are accommodated by this system.

Screening of cDNA: The phagemid from Uni Zap XRm was transfected into an *E. coli* strain (XL1-Blue MRF', Stratagene™. After plating the transfected cells on top agar, the cells were incubated for approximately four hours at 45° C., until small plaques were visible. Isopropyl thio-beta-D-galactopyranoside (IPTG, 10 mM) impregnated nitrocellulose membranes were placed onto the agar and allowed to incubate for four hours at 37° C. The membranes were removed and blocked for 45 minutes with 5% milk in Tris buffered saline (TBS). Incubation was continued for two hours with either rabbit anti-human vitronectin (Becton Dickerson Labware, Bedford, Mass.) 1:10,000, or fibrogen antibody (Dako, Denmark) 1:2,500 at room temperature. After a series of washes in TBS, the membranes were incubated with alkaline phosphatase conjugated (APC) goat anti-rabbit IgG (1:5,000) (Sigma) for two hours at room temperature. Following a series of washes in TBS, the membranes were developed with Vectastain NBT/BICP color reagent system (Vector, Burlingame, Calif.). The positive plaques were rescreened to obtain pure clones.

Purification and sequence of DNX: Excision from positive clones was carried out using the Ex-Assis/SOLR System (Stratagene). The phages were extracted and tranfected to the SOLR with Ex-Assist Helper Phage (Stratagene). These cells were grown overnight at 37° C., on ampicillin-supplemented medium. The cells were harvested and lysed by alkali buffer, and the DNA was extracted by phenol-chloroform extraction methods. DNA sequencing was performed by the Columbia University DNA sequencing laboratory, Columbia College of Physicians and Surgeons, New York, N.Y.

Expression of the recombinant DNA: The screened and purified plasmid was mixed with XL1-Blue MRF' cells (Stratagene) pretreated with $CaCl_2$. The mixture was heat shocked to allow transformation. The transformed cells were allowed to grow in non-selective media, and were then plated onto ampicillin enriched agar. A single colony was harvested and grown in liquid media supplemented with 10 mM IPTG. The cells were then lysed with lysozyme (Sigma, St Louis, Mo.), the debris was removed by centrifugation. Dye binding assays were undertaken to determine the protein concentration of the supernatant. A non-transfected colony was processed to identify cellular proteins.

Western Immunoblots: Western immunoblots were probed with either rabbit anti-human Ig kappa antibody, APC goat anti-human heavy chain antibody, IgGs purified from the sera of AAA patients and control patients.

Figure 11:
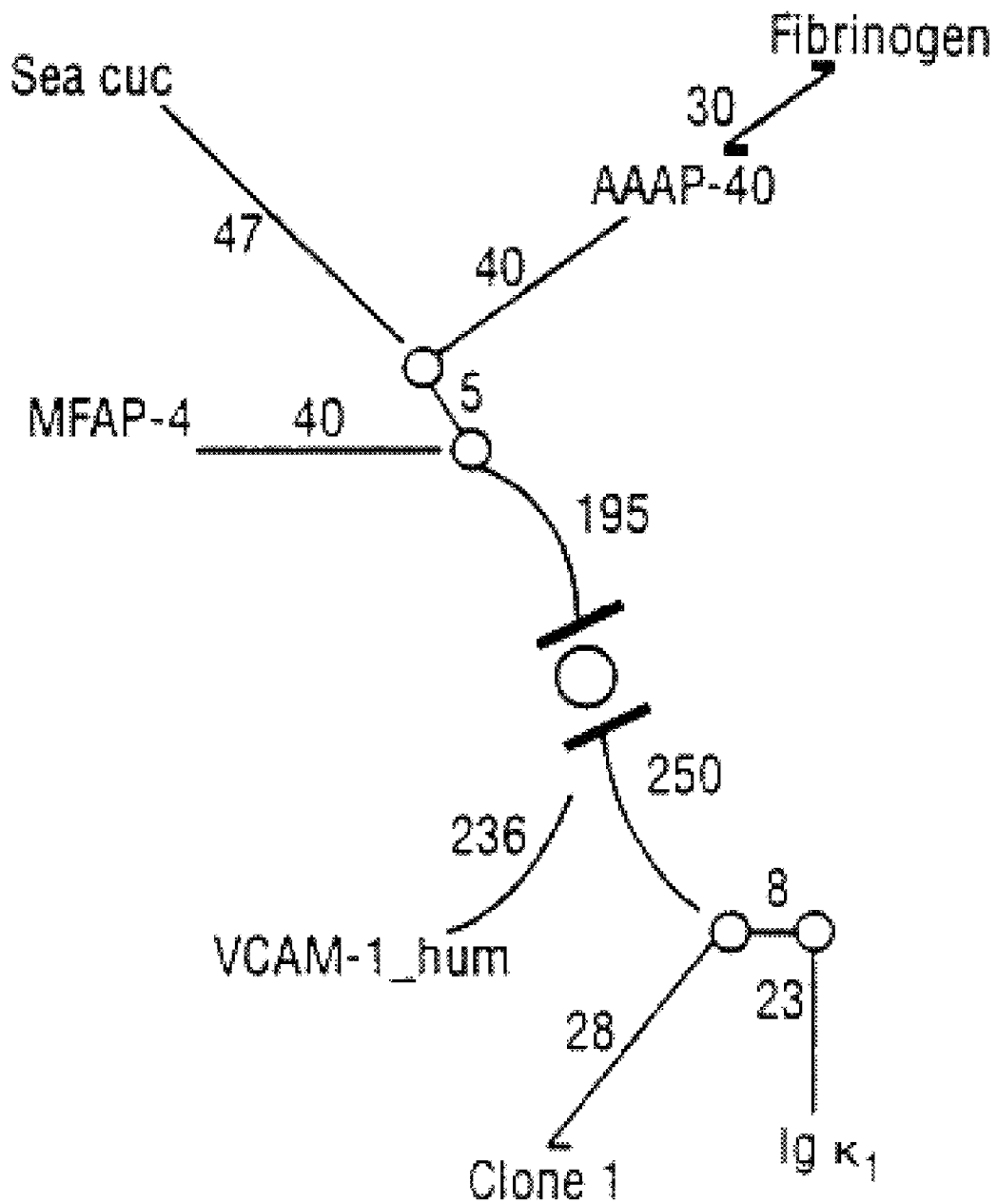

Computational biology and graphical displays: Protein sequences were downloaded from Retrieve [15] at the National Institutes of Health. Multiple alignments were performed with SIM™ at the Biologist's Control Panel of the Human Genome Project of the Baylor College of Medicine [16]. The probabilities of similarities between proteins was calculated by Blast-P™ and Motif™ [17,18]. Pairwise alignments were calculated at the Biologists Control Panel and similarity plots were displayed by LalnView [19]. Protein modeling were performed by SwissModel, [20] and the output files were displayed by Rasmol [21]. The evolutionary tree was calculated based on PAM™ distances calculated by AllAll™ [22]. FIG. 11 is not precisely drawn to scale. In the cartoon mode of Rasmol the beta strands are shown in yellow and the alpha coils are shown in red [19]. In "group" mode of Rasmol, color progresses from blue to dark green to light green to yellow to red as it reads from the N-terminus to the C terminus of the protein.

Results

Figure 6:
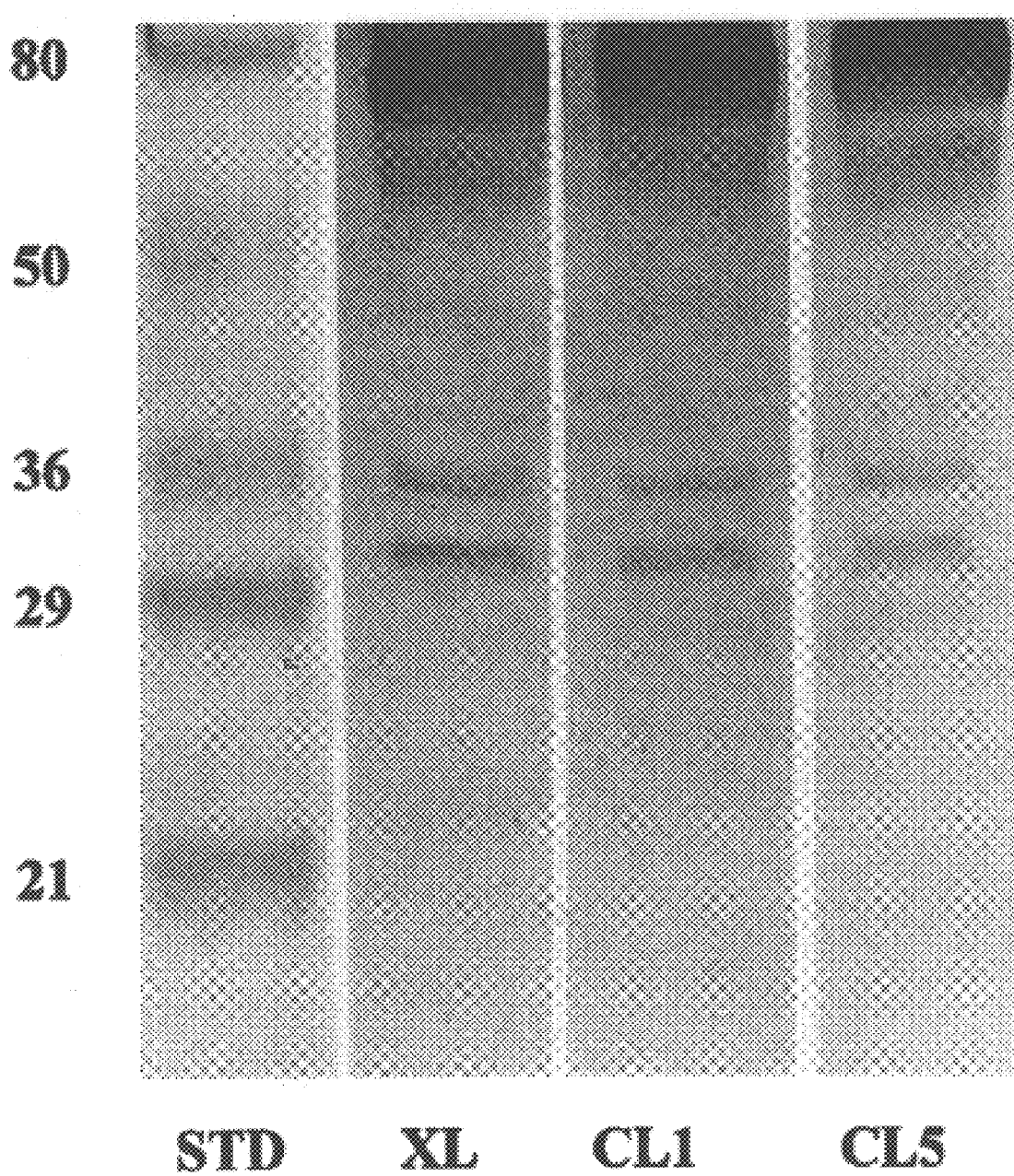
Figure 7:
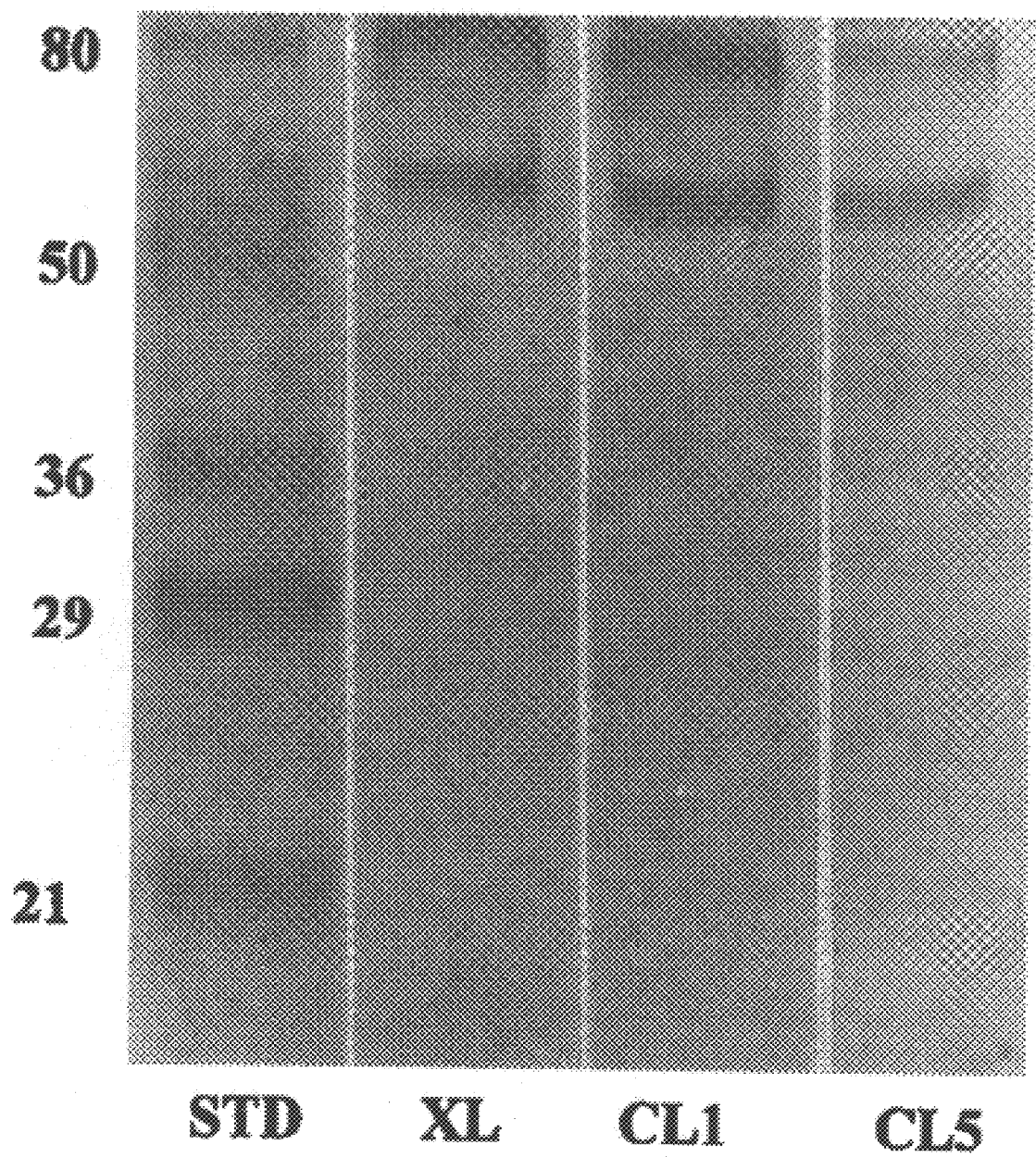
Figure 8:
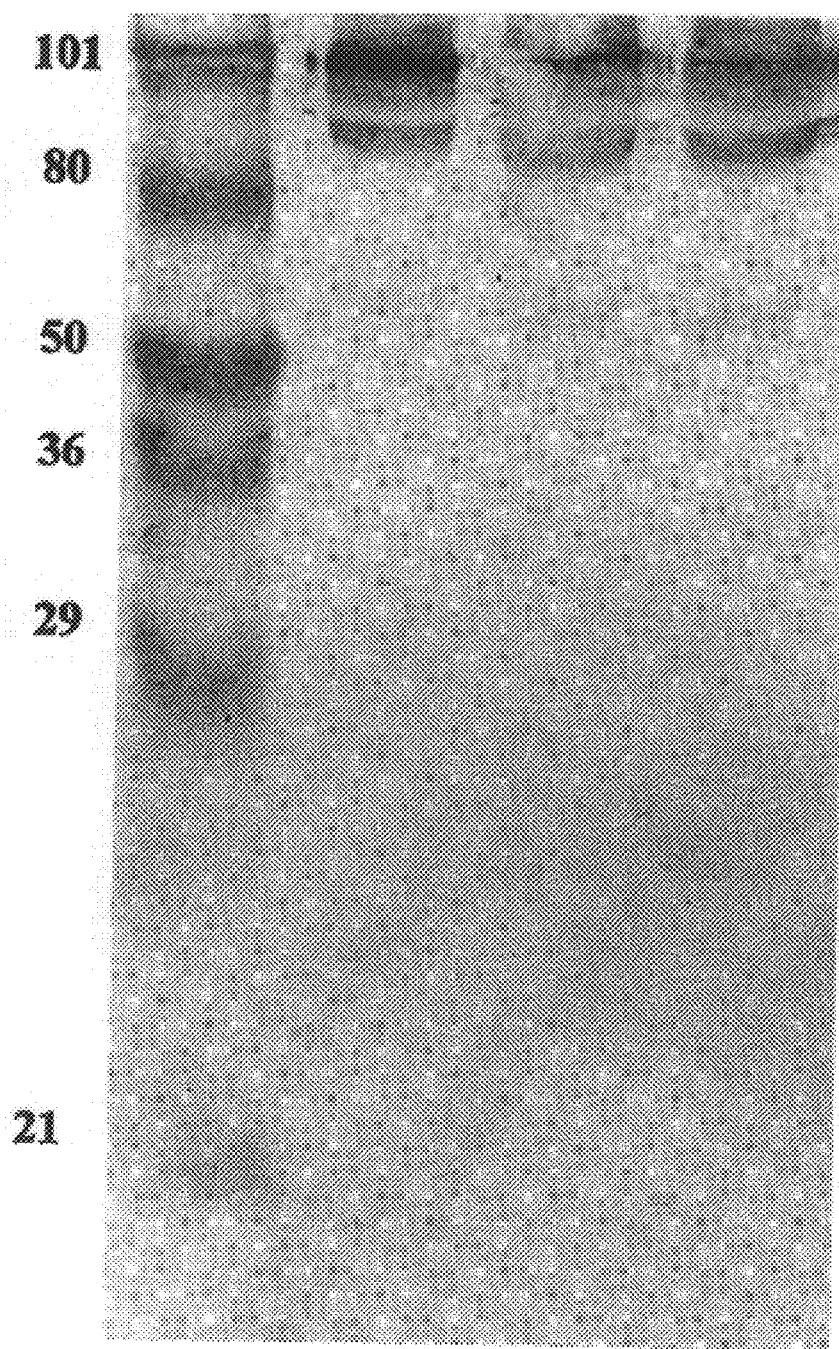
Figure 9:
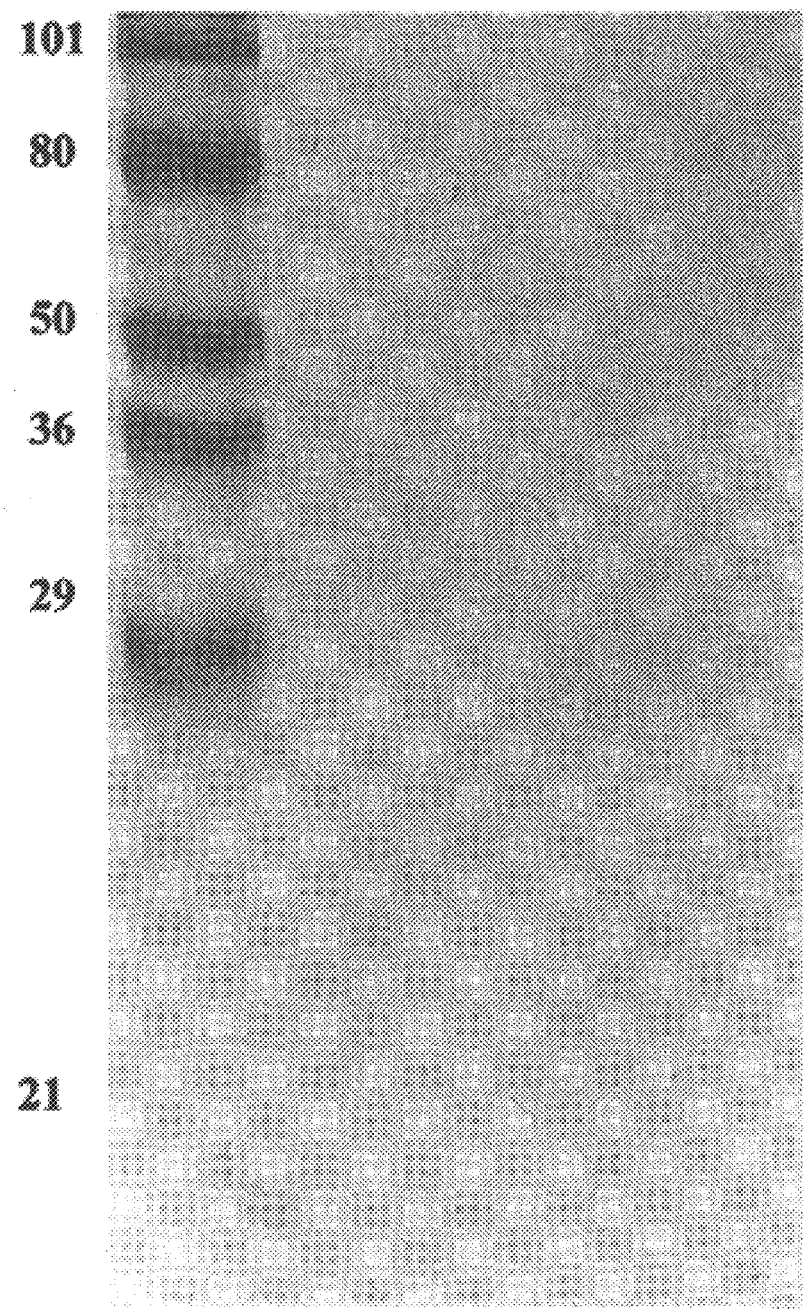

Recombinant proteins were expressed by the XL1-Blue MRF' cells transfected with the cDNA of Clone 1 and Clone 5. Western immunoblots showed that rAAAP-CL1 and rAAAP-CL5 were immunoreactive with serum IgGs from AAA patients at a MW of 28 kDa (FIG. 6). Western immunoblots probed with serum IgGs from normal volunteers showed no unique immunoreactivity (FIG. 7). rAAAP-CL1 and rAAAP-CL5 were immunoreactive on Western immunoblots probed with rabbit anti-human Ig kappa antibody (FIG. 8), not seen with APC goat anti-human heavy chain antibody (FIG. 9).

Figure 10A:
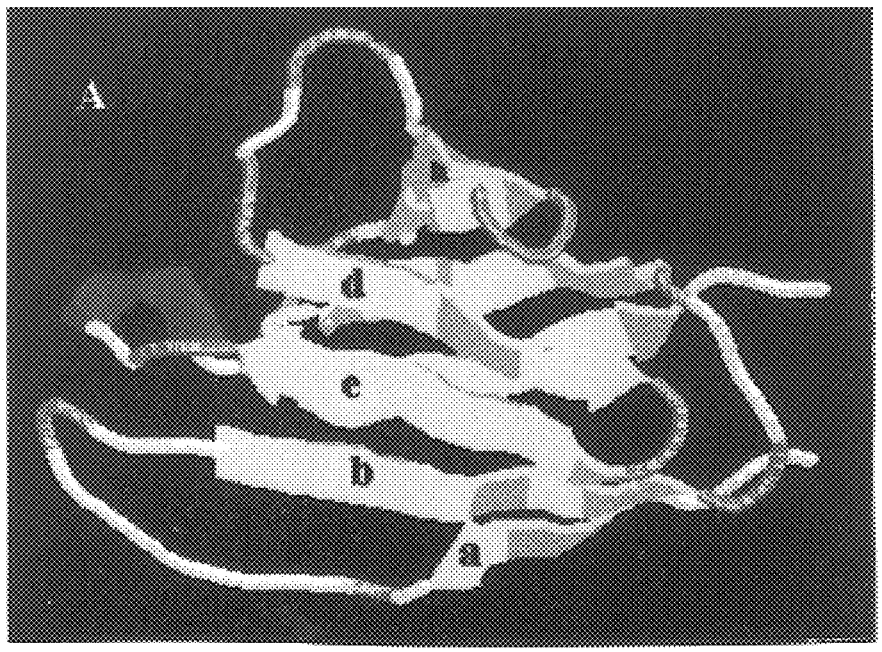
Figure 10B:
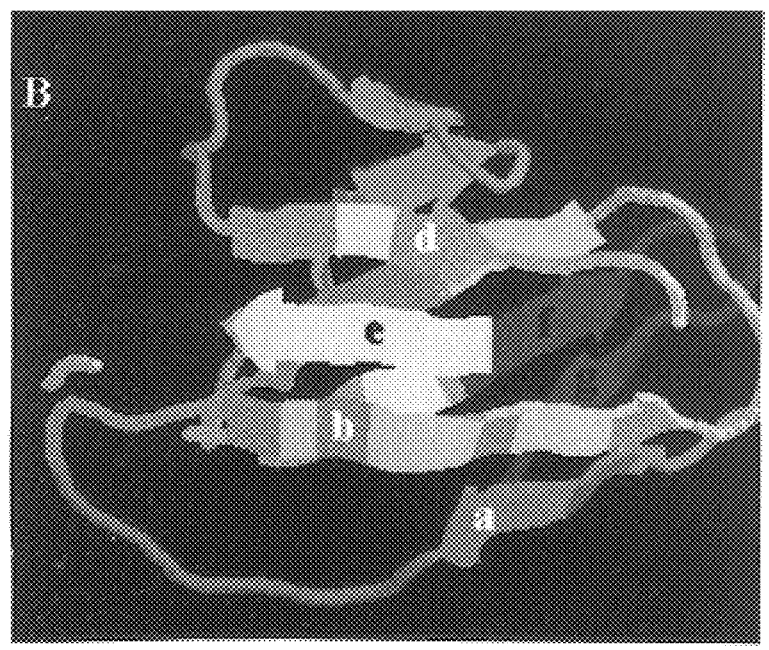
Figure 10C:
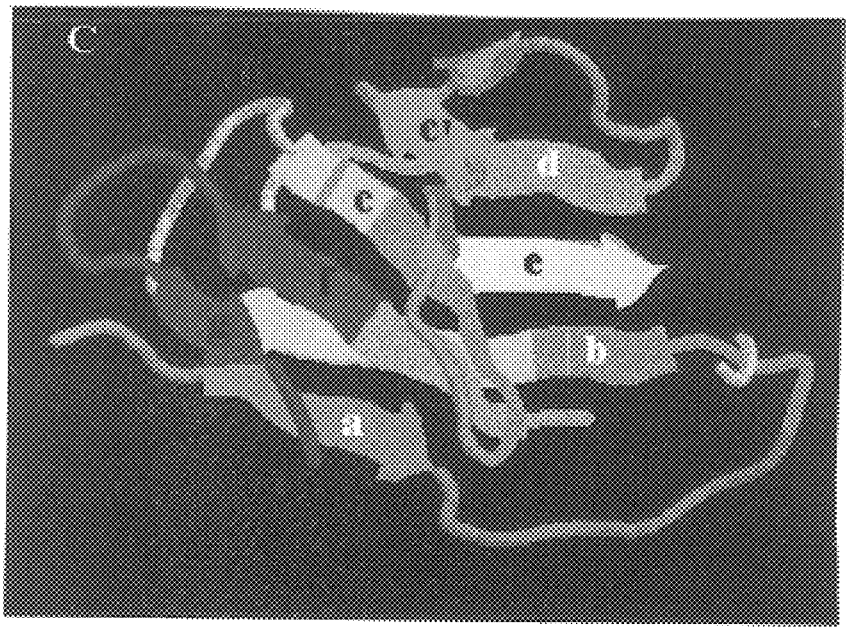

A search of the N-terminal 125 residues of rAAAP-CL1 with BlastP identified IgK precursor KV1J [23] as the closest match ($p=1.4 \times 10^{-50}$). FIG. 10A is a model of rAAAP-CL1 as calculated and displayed by RasMol, with beta-strands labeled according to the standard convention. [24]. FIG. 10B is the same molecule, rAAAP-CL1 with color coding blue to red, illustrating the progression from N-terminus to C-terminus. FIG. 10C is the backside of rAAAP-CL1 showing the bottom sheet of the beta-sandwich with strands c, c', f and g.

Figure 10D:
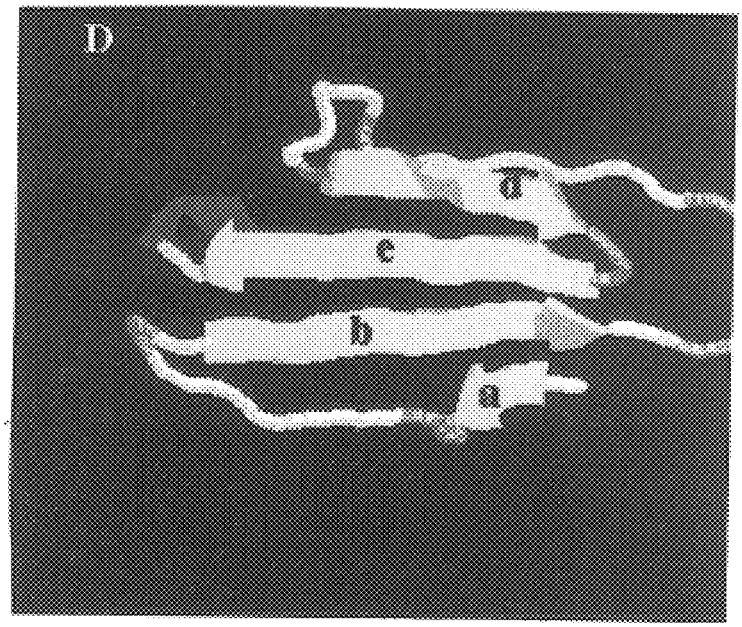

Among the first 100 matches by BlastP for the Ig-like sequence of rAAAP-CL1 (residues 20–124) was 1VCA [21] (immunoglobulin superfamily, integrin binding molecule of mouse, also known as VCAM1-mouse), with p=0.02. The homology occurred between rAAAP-CL1 and the first Ig-like domain of VCAM-1 mouse. Ninety-two of the other 100 matches were immunoglobulins. FIG. 10D is a cartoon of the tertiary structure of the first Ig-like domain of VCAM-1 mouse.

Figure 10E:
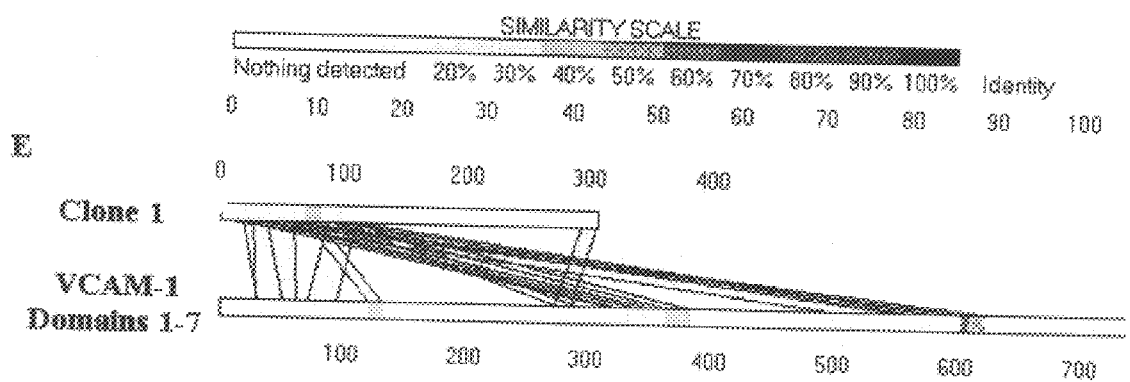
Figure 10F:
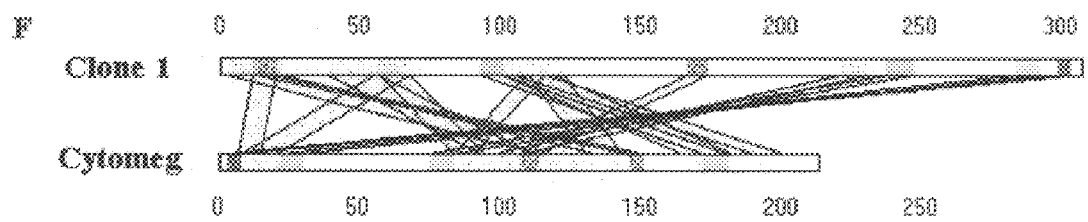

FIG. 10E is a pair-wise comparison displayed by Laln-View of the amino acid sequence similarities of rAAAP-CL1 and VCAM-mouse (domains 1–7). Since cytomegalovirus has been recently implicated as a potential molecular mimic in AAA disease, an additional alignment of rAAAP-CL1 with a cytomegalovirus protein, shows numerous similarities (FIG. 10F).

Discussion

AAA wall has been found to have an infiltrate of chronic inflammatory cells [1,25]. Immunohistochemical studies using AAA IgG have shown that binding co-localizes with adventitial elastin-associated fibrils. [1] Purification and sequencing studies have lead to the characterization of a putative autoantigen (AAAP-40) with sequence homologies to MAGP-36, vitronectin, fibrinogen and with several pathogens associated with aneurysmal disease (Treponema pallidum, Herpes simplex virus and cytomegalovirus).(2)

An effort to clone the cDNA for AAAP-40 from an expression library made with human aortic mRNA has resulted in the cloning of three related genes, which encode recombinant proteins that are also immunoreactive with AAA serum and tissue IgG. Two of the clones (Clone 1 and Clone 5) are similar to each other, and they also have even stronger similarities to the variable region of the immunoglobulin kappa (IgK's). [6]. Accordingly, they have been called "kappafibs."

The similarities of rAAAP-CL1 and VCAM-1 mouse are evident on comparing FIGS. 10A and 10D. There is virtual identity in the predicted tertiary structure of the front beta-sheet of rAAAP-CL1 and the first Ig-like domain of VCAM-1 mouse (although the first Ig-like domain of VCAM-1 lacks a backside beta-sheet). These similarities of spatial structure occur despite a low level of conservation of amino acid residues as shown in FIG. 10E, where the similarities of amino acid sequence between the first 124 residues of rAAAP-CL1 and VCAM-1-mouse are less than 30%, confirming the observation of Bork, Holm, and Sander that "three-dimensional structures are much more conserved in evolution than are sequences". [19].

Because the N-terminal portion of the CD loop (beginning with a glutamine residue) "appears to be vital in directly mediating integrin binding",[26] we were interested to note that a glutamine residue occupies a similar site in rAAAP-CL1, as well as in the BC, C—C, C'-C" and FG loops.

It has been reported that kappafibs have similarities to the fibrinogens and to the immunoglobulins kappa [6]. Similarity to the fibrinogens was not unexpected, since the previously described microfibrillar proteins (AAAP-40 [2], MAGP-36[ ][4] and MFAP-4[ ][2])[7] have fibrinogen-like motifs. The strategy for seeking a candidate common ancestor was to perform a multiple alignment of four members of the overall family. The program Motif provided a promising 40 residue sequence of similarity (Table V). A Blast-P search of the 40 residue sequence from MFAP-4 (beginning FKR . . . ) revealed a highly significant alignment with an ancient protein from the sea cucumber ($p=2 \times 10^{-11}$), which is called fibrinogen-related protein-A precursor [28](Table VI). A multiple alignment for all the proteins studied is shown in Table VII.

The similarities of the clones to the immunoglobulins occur in the variable domains of the immunoglobulins sheet, suggesting that these new proteins may be tissue-specific signals that inform cells as to their whereabouts, e.g. Matrix Cell Adhesion Molecules, or "MAT-Cams". A smooth muscle cell, for example, residing in the aorta instead of the ureter, needs some clues as to the appropriate ratio of Type III or Type I collagen to manufacture to suit the requirements of its specific location. This function is perhaps more primitive than soluble immunity, so it is conceivable that the immunoglobulins arose from the MAT-Cams in molecular evolution. Non-specific immunity first appeared in primitive metazoans like sponges; but soluble immunity did not appear until relatively recently in evolutionary history (cartilagenous sharks).[29] Considering that matrix proteins probably appeared with the first multicellular organisms, the notion that matrix adhesion molecules may have appeared before immunoglobulins is not implausible.

Xu and Doolittle suggested that the mammalian fibrinogens share a common ancestor with the fibrinogen-like peptide of the invertebrate Echinoderm, which appeared in similarity searches.[30] The homologies of the fibrinogen-related protein-A precursor of sea cucumber span almost 80% of the length of MFAP-4. To examine the hypothesis that MAT-Cams may have preceded soluble immunity, AllAll[31] were used to calculate the point-accepted mutation rates (PAM units) for several proteins. For fibrinopeptide related proteins, a PAM unit has been estimated to be about 1 million years.[32] The phylogenetic tree in FIG. 11 indicates that clone 1 is significantly closer to an immunoglobulin kappa than any other protein under consideration. FIG. 11 also suggests that there were two clusters of evolutionary activity. The first was around the time of the Cambrian radiation (producing the fibrinogens and the microfibril-associated glyco-proteins); and the second much more recently (spawning the CAM's first and then the immunoglobulins).

In conclusion, there appear to be several candidate autoantigens in AAA disease. The two described here have lengthy immunoglobulin domains and may serve as cell adhesion molecules. Finally, the novel hypothesis is raised that the MAT-Cams may be closer to their common ancestor than the soluble immunoglobulins.

TABLE V

Alignment of a similarity block from Clone 5, Ig kappa, MAGP-36, and MFAP-4 by the MOTIF program.****

```
Clone  5   57  WYQQKPGKAPKLLIHAASSLQTGVPSRFSGSGSGTXFTLT
Ig-kappa   57  WYQQKPGKAPKLLIYAASTLQSGVPSRFSGSGSGTDFTLT
MAGP-36    27  SGPRFCGSVSFFRGWNDYKLGFGRADGEYWLGLQNMHLLT
MFAP-4     82  FQKRFNGSVSFFRGWNDYKLGFGRADGEYWLGLQNMHLLT
```

TABLE VI gi/790817 (L38486) microfibril-associated glycoprotein 4 [Homosapiens]
Length = 256 Score = 125 (58.7 bits),
Expect = 2.7e-11, P = 2.7e-11
Identifies ≈ 19/40 (47%), Positives = 30/40 (75%)

```
SEA CUCUMBER    1  FQRRIDGTINFYRSWSYYQTGFGNLNTEFWLGNDNIHYLT  40
                   FQ+R +G+++F+R W+ Y+ GFG  + E+WLG   N+H LT
MFAP-4         83  FQKRFNGSVSFFRGWNDYKLGFGRADGEYWLGLQNMHLLT  122
```

TABLE VII

CLUSTALW Multiple Sequence Alignment Results

```
             1              15  16              30  31              45
1 IgK1       ---MKKTAIAIAVAL    AGFATVAQAAELTQS    PSSVS---ASVGDRV
2 clone_1    -MDMRVPAQLLGLLL    LWLPGARCDIQLTQS    PSLLS---ASVGDRV
3 Igk2       ---MVLQTQVFISLL    LWISGAYGDIVMTQS    PDSLA---VSLGERA
4 clone_5    ---MVLQTQVFISLL    LWISGANGDIVMTQS    PDSLG---VSLGERA
5 magp_36    ---------------    ---------------    --------SELQLPL
6 mfap_4     ---MKALLALPLLLL    LSTPPCAPQVSGIRG    DALER---FCLQQPL
7 sea_cuc    MFSFIMKAAILLILV    GCISFCISSEPLNES    EITFEREERSLADPA
8 aaap_40    ---------------    ---------------    ---------------
             46             60  61             75  76              90
1 IgK1       T-------ITC--RA    SQGISS---------    --------WLAWYQQ
2 clone_1    M-------ITC--RA    SQAISS---------    --------FLAWYQQ
3 IgK2       T-------INC--KS    SQSLLYS--------    ---SNNKNYLAWYQQ
4 clone_5    T-------INC--RS    SQRLFFG--------    ---SNSKNYLAWYQQ
5 magp_36    D-------EDD--IY    AQGYQA---------    --------DGVYLIP
6 mfap_4     D-------CDD--IY    AQGYQS---------    --------DGVYLIY
7 seq-cuc    GRQKRQSGLSCPKRI    SHSPEYPRDCYDILQ    SCSGQSPPSGQTTIQ
8 aaap_40    ---------------    --NENN---------    --------VVNEYSQ
             91            105  106            120  121            135
1 IgK1       KPGKAPKLLIYSASS    LQSG----VPSRFSG    SGSG-TDFSLTISSL
2 clone_1    KPGKAPKLLIHAASS    LQTG----VPSRFSG    SGSG-TXFTLTISXL
3 Igk2       KPGQPPKLLIYWAST    RESG----VPDRFSG    SGSG-TDFTLTISSL
4 clone_5    KPGQSPKLLIYWAST    RDSG----VLTDSLA    AGLGXISLSPSXXCR
5 magp_36    -SGP-----------    -----------RFCG    SVSFFRGWNDYKLGF
```

TABLE VII-continued

CLUSTALW Multiple Sequence Alignment Results

```
6 mfap_4    PSGPSVPVPVFCDMT  TEGGKWTVFQKRFNG  SVSFFRGWNDYKLGF
7 sea_cuc   PDGGN-LIKVYCDME  TDEGGWTVFQRRIDG  TINFYRSWSYYQTGF
8 aaap_40   ELEKK----------  FEDG-------VLDP  DYPX---WTVFQXYF
              136        150  151        165  166        180
1 IgK1      QPEDSATYYCQQANS  FPYTFG----QGTKV  EIKRTVAAPSVFIFP
2 clone_1   QSEXLQLYYCQHLKG  YPITFRPRDTXGXXX  NCXCTIXSSSSRHLX
3 IgK2      QAEDVAVYYCQQYYS  TPPMFG----QGTKV  EIKRT----------
4 clone_5   LKNLILXLSAIIIS   XXTFRP----WGTXL  XIQXKCWXAXIFXSF
5 nagp_36   GRADGEYWLGLQNMH  LLTLK--YELRVDLE  DFEXNTAFAKYADFS
6 mfap_4    GRADGEYWLGLQNMH  LLTLKQKYELRVDLE  DFENNTAYAKYADFS
7 sea_cuc   GNLNTEFWLGNDNIH  YLTSQG---DYELRV  ELNNTLGNHYYAKYN
8 aaap_40   PFVDLMVMANQPMGE  KYYDF------FQY   TXGMAKEYDGFQYTX
```

THIRD SERIES OF EXPERIMENTS

REFERENCES

1. Gregory, A. K., Yin N. X., Capella, J., Xia, S., Newman, K. M., and Tilson, M. D. Features of AutoImmunity in the Abdominal Aortic Aneurysm. *Arch of Surg.* 131:23–25, 1996.
2. Xia, S., Osvrath, K. J., Hirose, H., and Tilson, M. D. Partial Amino Acid Sequence of a Novel 40 kDA Human Aortic Protein with Vitronectin-like, Fibrinogen-like, and Calcium Binding Domains: Aortic Aneurysm-Associated Protein-40 [Human MAGP-3, Proposed]. *Biochem. Biophys. Res. Commun.* 219, 36–39, 1996.
3. Tilson, M. D. Similarities of an Autoantigen in Aneurysmal Disease of the Human Abdominal Aorta to a 36-kDa Microfibril-Associated Bovine Aortic Glycoprotein. *Biochem. Biophys. Res. Commun.* 213:40–43, 1995
4. GeneBank Accession Number SP¦P80520
5. Kobayashi, R., Mizutani, A., Hidaka H. Isolation and Characterization of a 36 kDA Microfibril Associated Glycoprotein by the Newly Synthesized Isoquinoline-sulfonamide Affinity Chromatography. *Biochem. Biophys. Res. Commun.* 198:1262–1266, 1994.
6. Kobayashi, R., Tashima, Y., Masuda, H., Shozawa, T., Numata Y., Miyauchi, K., and Hayakawa, T. Isolation and Characterization of a New 36-kDa Microfibril-Associated Glycoprotein from Procine Aorta *J. Biol. Chem.* 264:1737–44, 1989.
7. GeneBank Accession Number GI¦543129
8. GeneBank Accession Number SP¦P19477
9. Ozsvath, K. J., Xia, S., Hirose, H., Tilson, M. D. Two Hypothetical Proteins of Human Aortic Adventitia, with Ig Kappa, Collagenous, and Aromatic-Rich Motifs. *Biochem. Biophys. Res. Commun.* 225:500–504, 1996.
10. GeneBank Accession Number SP¦P80520
11. Oszvath, K. J., Hirose, H., Xia, S., and Tilson, M. D. Molecular Mimicry in Human Aortic Aneurysmal Diseases. New York Academy of Science Conference Abstract Book *The Abdominal Aortic Aneurysm-Genetic Pathophysiology, and Molecular Biology*: 28, 1996.
12. Tanaka, S., Komori, K., Okadome, K., Sugimachi, K., and Mori, R. Detection of Active Cytomegalovirus Infection in Inflammatory Aortic Aneurysms with RNA Polymerase Reaction. *J. Vasc. Surg.* 20:235–43, 1994.
13. DePalma R. G., In R. M. Greenhalgh J. A., Mannick, and J. T. Powell (Eds). *The Cause and Management of Aneurysm*, London: WB Suanders Company, 1990. Pp. 97–104.
14. IgKappa 1 is GeneBank Accession Number GI¦1514581; and Ig Kappa 2 is GeneBank Accession Number GI¦185921 (IgK chain v J1-region precursor).
15. "retrieve@ncbi.nlm.nih.gov
16. http://kiwi.imgen.bcm.tmc.edu:8088/bio/bio_home.html
17. Altshul S. F., Gish W., Miller W., Myers E. W., and Lipman, D. J., Basic Local Alignment Search Tool *J. Mol. Biol.* 215:403–10, 1990.
18. Henikoff, S., Henikoff, J. G., Alford, W. J., and Pietrokovski, S., Automated Construction and Graphical Presentation of Protein Blocks from Unaligned Sequences. Gene-COMBIS, *Gene.* 163:GC 17–26, 1995.
19. Duret L., LALNVIEW v2.2 Available at the Biologist's Control Panel of the Human Genoma Project of the Baylor College of Medicine http://iwi.imgen.cm.mc.edu.8088/bio/bio_home.html
20. Peitsch, M. C., Promod and Swiss-Model: Internet Based Tools for Automated Comparative Protein Modeling. *Biochem Soc Trans.* 24:274, 1996. Available at Swissmod@ggr.co.uk.
21. Sayle, R., RasWin Molecular Graphics, version 2.6. Freeware.
22. Korostensky C., (webmaster). AllAll.html. Available at http://cbrg.inf.ethz.ch
23. GeneBank Accession Number SW¦P01602
24. Bork, P., Holm, L., and Sander C., The ImmunoGlobulin Fold: Structural Classification, Sequence Patterns and Common Core. *J. Mol. Biol.* 242:309–320, 1994.
25. Brophy, C. M., Reilly J. M., Walker-Smith G. J., Tilson, M. D. The Role of Inflammation in Non-Specific Abdominal Aneurysm Disease. *Ann. Vasc. Surg.* 5:229–233, 1991.
26. Jones, E. Y., Harlos, K., Bottomley, M. J., Robinson, R. C., Driscoll, P. C., Edwards, R. M., Clements, J. Y., Dudgeon, I. J., Stuart., D. I., Crystal structure of an Integrin-Binding Fragment of Vascular Cell Adhesion Molecular-1 at 1.8 A Resolution *Nature* 373:539–44, 1995.
27. GeneBank Accession Number GI¦790817 (L 3486)
28. GeneBank Accession Number SP¦P19477
29. Horton, J., Ratcliffe, N. Evolution of Immunity. Immunology (4th Ed.), eds. Roitt I, Prostoff J., Male D. Mosby (Baltimore) 1996; pp1–15.22.
30. Xu,X., Doolittle, R. F. Presence of a Vertebrate Fibrinogen-Like Sequence in an Echinoderm. *Proc. Nat. Acad. Sci. (USA)* 1990; 87:2097–2101.
31. Korostensky, C. (webmaster). AllAll.html. Available at http://cbrg.inf.ethz.ch
32. Wilson, A. C., Carlson, S. S., White, T. J. Biochemical Evolution. *Ann. Rev. Biochem.* 1977; 46:573–639.

FOURTH SERIES OF EXPERIMENTS
EXPERIMENTAL DETAILS

Immunoglobulins (IgGs) purified from the aortic wall of patients with abdominal aortic aneurysms (AAAs) are immunoreactive with a human aortic protein that we have purified and sequenced in part.(1,2,3) It has homologies with the bovine Microfibril-Associated GlycoProtein 36 kDa (MAGP-36), which was discovered by Kobayashi et al.(4) and found to have a tissue distribution uniquely limited to the aorta.(5) The human protein is named "Aortic Aneurysm Antigenic Protein 40 kDa" (AAAP-40). A sequence in AAAP-40 matches an eleven residue sequence in human vitronectin,[4] and a similar motif occurs in MAGP-36 (Table VIII). AAAP-40 is immunoreactive with rabbit anti-human vitronectin antibody.(6)

Since vitronectin is synthesized in liver (not aortic adventitia), an expression library from adventitia was screened for recombinants that are immunoreactive with rabbit anti-human vitronectin; and the amino acid sequences of two positive clones that strongly resemble each other are reported.(7) This series of experiments reports the amino acid sequence of a third clone (originally the fourth clone in the series, hence "rAAAP-CL4"), because the gene product is also immunoreactive with IgG from patients with AAA.

Methods

Human subjects: Specimens of AAA tissue and peripheral blood were taken from patients at the time of infrarenal AAA repair. Normal abdominal aorta was harvested from organ donors. The protocols for human investigation have been approved by the Institutional Review Board. Surgical specimens were frozen immediately, ant then stored at −110° C. until use in biochemical studies. Serum was obtained from blood samples, and stored at −20° C. until further studies.

Purification of IgG: Human IgG was purified separately from aortic tissue and from serum as described previously. (1)

Construction of cDNA Libraries: mRNA from aortic adventitia of a AAA specimen was reverse transcribed for insertion into the phagemid, Uni Zap XR™ lambda vector system, by Stratagene™ (La Jolla, Calif.). This system accommodates DNA inserts up to 10 kb in length.

Expression of cDNA: The phagemid from Uni-Zap XR vector was transfected into a strain of $E.$ $coli$ (XL1-Blue MRF', Stratagene™). The transfected cells were plated on top agar, and then allowed to grow at 45° C. until small plaques were visible (approximately 4 hours). Nitrocellulose membranes, impregnated with 10 mm Isopropyl thio-beta-D-galactopyranoside (IPTG), were placed onto the agar, and were incubated for 4 hours at 37° C. The membranes were removed and blocked with 5% milk in TBS for 45 minutes. Incubation was continued with rabbit anti-human vitronectin antibody (Becton-Dickson, Bedford, Mass.) (1:10,000) for 3 hours at room temperature. After washing in TBS, the membranes were incubated with alkaline phosphatase conjugated (APC) goat anti-rabbit IgG (Sigma, St. Louis, Mo.) (1:5000) for 2 hours at room temperature. Following a series of washes in TBS, the membranes were developed by Vectastain NBT/BICP color reagent system (Vector, Burlingame, Calif.). The estimated frequency of the positive clones was 1:10,000 on primary screening and 1:1000 on secondary screening. The positive plaques were rescreened to obtain pure clones.

Purification add sequencing of DNA: Excision from positive clones was carried out using the Ex Assist/SOLR System (Stratagene™). The phages were collected from the agar plate using chloroform extraction, and then transfected to SOLR cells with amplified Ex Assist Helper Phage (Stratagene™), which prevents replication of the experimental phage. The transformed cells were allowed to grow overnight at 37° C. on ampicillin-supplemented medium which inhibits the growth of non-transfected cells. The cells were harvested, and then lysed by alkali buffer. DNA was purified by the phenol—chloroform extraction method and quantified by spectrophotometry. Agarose gel electrophoresis confirmed the presence of plasmid DNA. DNA sequencing was carried by the DNA Sequencing Laboratory at Columbia University, New York, N.Y.

Expression of the recombinant DNA: The screened and purified plasmid was mixed with XL1-Blue MRF' cells pre-treated with $CaCl_2$. The mixture was then heat shocked to allow transformation. The transformed cells were grown in non-selective media and plated onto ampicillin-containing agar to identify the plasmid-containing colonies. A single colony was grown in liquid media for 6 hours and continued to incubate for 4–6 hours with 10 mM IPTG supplementation. The cells were lysed with lysozyme (Sigma, St. Louis, Mo.), and cell debris was removed by centrifugation at 20,000 g for 1 hour. Protein concentration of the supernatant was determined by dye-binding assays. A non-transfected colony underwent similar processing to identify cellular proteins. Western immunoblots were probed with IgG purified from serum of AAA patients or normal volunteers.

Alignments. The work was done with an IBM compatible computer, Netscape Navigator™ 1.4, and a modem. Protein sequences were downloaded from Retrieve at the National Institute of Health (NIH)(8) and pasted into the Pairwise Alignment Program at the Biologist's Control Panel at the Human Genome Project of the Baylor College of Medicine. (9) The alignments were displayed with LalnView, which is also available at the Baylor College of Medicine Web site.(9) The screen was saved for each alignment, and then pasted into PaintBrush™ for cropping and printing. Multiple pairwise alignments were performed with MOTIF, which is also available at the Biologist's Control Panel.(9)

Results

Figure 12:
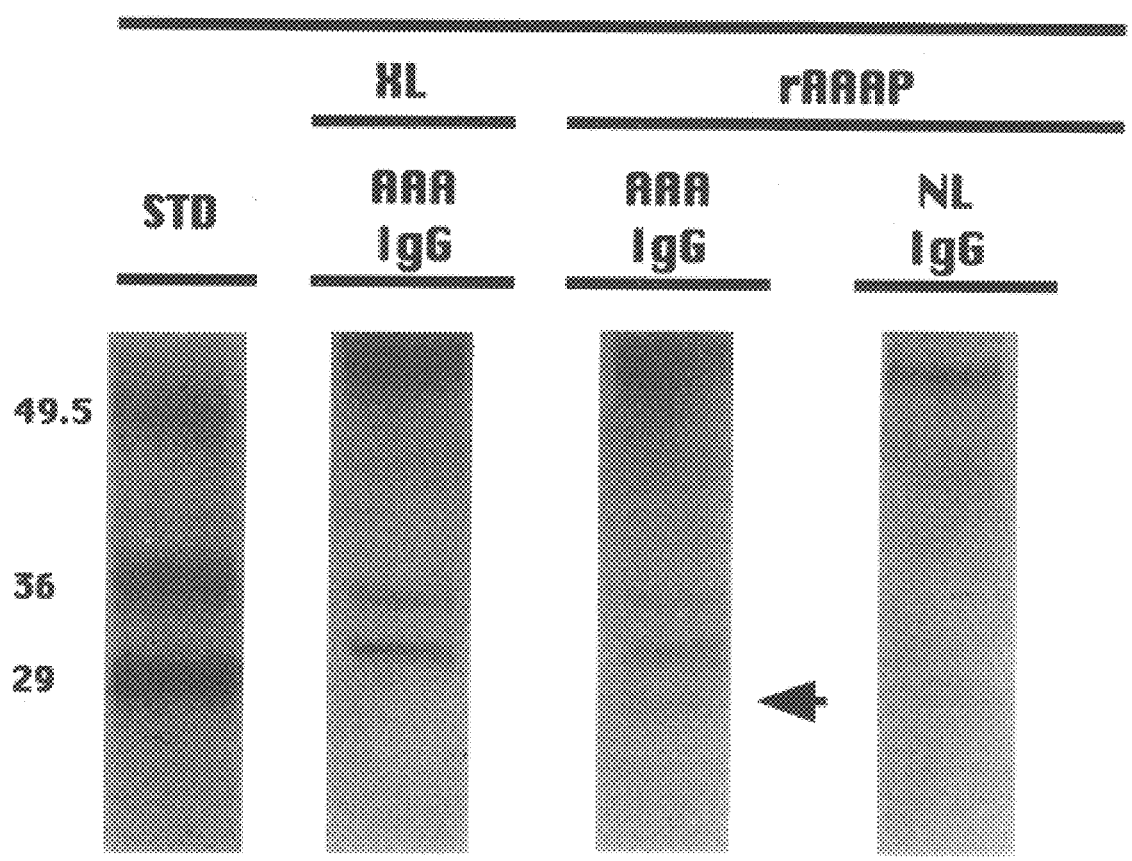

A recombinant protein was expressed by the XL1-Blue MRF' cells transfected with the cDNA of clone 4. Western immunoblots showed that rAAA-CL4 was immunoreactive with IgGs from AAA patients at a MW of 28 kDa (FIG. 12). (3 out of 4 sera) It did not react with IgGs from normal volunteers. (0 out of 3 sera)

The amino acid sequence of the protein encoded by clone 4 (rAAAP-CL4) is shown in Table IX, in alignment with several related proteins. rAAAP-CL4 does not encode AAAP-40. Since the known MAGP's (MAGP-36 and MFAP-4) strongly resemble each other, and they also resemble fibrinogen-beta,(4) a pair-wise alignment of rAAAP-CL4 was carried out against these three proteins to evaluate their degree of relationship (Table IX).

Figure 14:
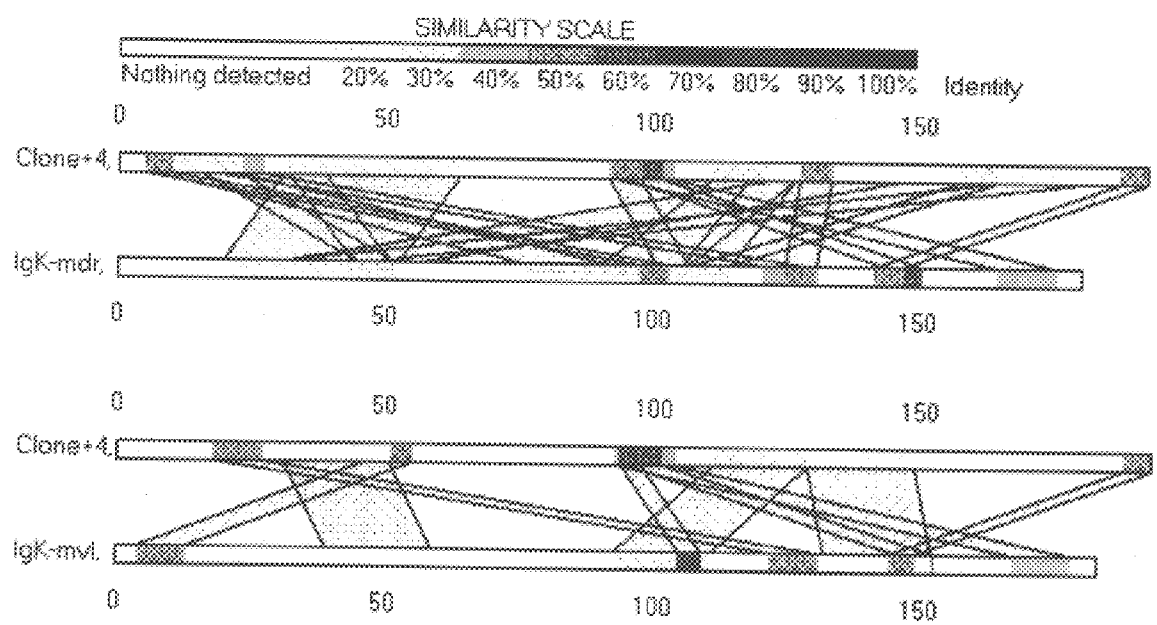

The proteins encoded by clones 1 (rAAAP-CL1) and 5 (rAAAP-CL5) have been reported, and these clones have lengthy sequences with high degrees of homology with immunoglobulins of the kappa family (IgK's).(7) They may be matrix cellular adhesion molecules ("MAT-CAMSs"). Accordingly, alignments were done with rAAAP-CL4 against two Ig kappa sequences that are related to clones 1 and 5 (FIG. 14).

Since the cytomegalovirus has recently been implicated as a potential molecular mimic in AAA disease,(10) an additional alignment of rAAAP-CL4 was done against a cytomegalovirus protein (and against an influenza protein as a control).

Discussion

An infiltrate of chronic inflammatory cells has been described in AAA wall. (11, 12, 13, 14) Tumor necrosis factor-alpha, interleukin (IL)-1 beta, IL-6, and IL-8 have also been shown to be elevated in AAA tissue when compared to control aortic tissue. (15, 16, 17) Increases in matrix-degrading enzymes have been found in AAA wall associated with infiltration of mononuclear cells. (18, 19, 20) These observations suggest that autoimmunity may play a role in the pathogenesis of AAA.

Previous work has led to the hypothesis that the self-antigens in AAA disease belong to a family of proteins with similarities to MAGP-36.(3, 7) It has also been suggested that some bacterial and viral pathogens (*T. pallidum*, herpes viruses, and cytomegalovirus) may be molecular mimics (like certain mycobacteria in rheumatoid arthritis).(10) Molecular mimics are pathogens with epitopes capable of initiating autoimmunity against self-proteins. Since herpes and cytomegalovirus are so ubiquitous, it remains to explain why a relatively small number of exposed persons eventually develop AAA. A working hypothesis is that the genetic susceptibility resides in the MHC Class II DR-B family of alleles.(21)

Figure 13:
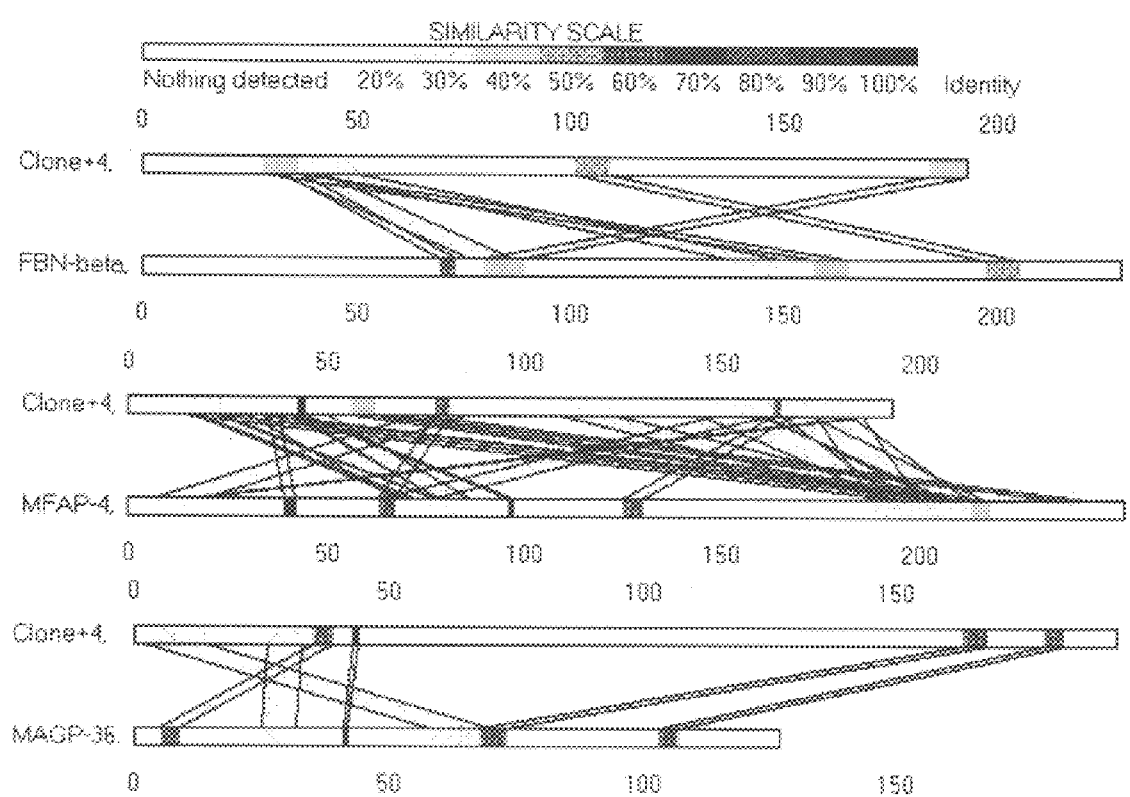

The present experiments give the deduced amino acid sequence of the fourth potential autoantigen. The experimental molecular weight of rAAAP-CL4 (28 kDa) is not inconsistent with the deduced sequence of 193 residues, since the information is incomplete in the region of the cDNA between the forward and reverse transcripts of the clone. The similarity of sequences from rAAAP-CL4 and the known microfibrillar proteins suggest that it is another a member of the the MAGP family (FIG. 13); but the relationship is not as close as that of AAAP-40 to other MAGP's. The similarity of rAAAP-CL4 to the Ig kappa sequences (FIG. 14) is compatible with the notion that it belongs to a super-family including Clones 1 and 5, which use immunoglobulin motifs in the extracellular matrix for interaction with members of the integrin family.(22)

Figure 15:
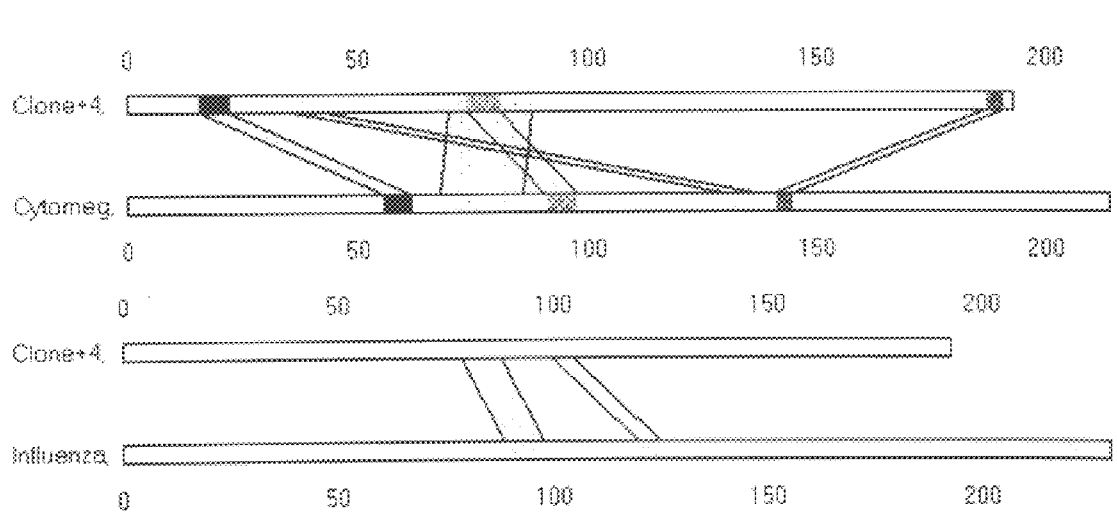

Finally, the resemblance of rAAAP-CL4 to a protein from cytomegalovirus is greater than that of rAAAP-CL4 to a protein from influenza (as shown in FIG. 15). This finding is consistent with the hypothesis that cytomegalovirus might be a molecular mimic.

TABLE VIII

Alignment of homologous sequences from AAAP-40, MAGP-36, MFAP-4, and vitronectin. $ = K or R; "." = non-conserved residue;

| | | | | | | | | | | | |
|---|---|---|---|---|---|---|---|---|---|---|---|
| $ | F | E | D | G | V | L | D | P | D | Y | P | AAAP-40 |
| R | F | E | D | G | V | L | D | P | D | Y | P | VN |
| | | | D | G | VYL | . | P | | | | | MFAP-4 |
| | | | D | G | VYL | . | P | | | | | MAGP-36 |

TABLE IX

The deduced amino acid sequence of rAAAP-CL4 in single amino acid letter code. "X" = ambiguous residue; spaces represent discontinuities in sequence; and "--> <--" = ambiguous region between forward and reverse reading frames of the nucleic acid sequence. Motifs from other proteins described in text are shown in alignment with rAAAP-CL4.

```
YGLRSLSALQ XHLEACLLTS GGGXRLQEGP ATCHLPCDQA KKWNXKSQTF ICMLLCPFCR    60
YELRSLS         C..TT  .GG        P  ..C L.CD    KW......F      C.F..  MFAP-4
YELK                   G...L...G           A KE.D                     AAAP-40
YEL                LLF. G  R.Q.G        H.P.... .QW            F.R    VN
    SLSA..   .H   C.L.S GG          P ATC  PC.Q. Q                    Cytomeg
XNXILKXFFF XLQFALSFPT PTTNPLFEXX XSPEPXDFQW KEKNHXGTFV SNLXFXLNIS     120
.N    K.FYY SLK ALS   T P..P                   FQ.R    FV  .N         MFAP-4
       RGFYY SLK     FP                        QW R K...G Y.  ..L Y...L AAAP-40
       RVYFF    QY.L..P. P    P...E..  .S..PD     EEKN            NIS  VN
           F .LR..LS.PT PT..V.YQ                                       Cytomeg
----------------------><-----------------------KFF CXEFGLKAXI     121-133
                                                         Y.LR         MFAP-4
                                                   KFF   YGLR         AAAP-40
                                                   KYY   Y.L          VN
                                                   Y  C.E...KA        VN
RSPXKAXXGM SDVIVKCPVI XFMNAKWGCK YFLNVCISNL FDXXWGFTLH PCACFPNCEE     END
            DV.D  PV. VF  A.W..R .F......NL           PCS            MFAP-4
            P..  ..MN...G.K YY                                        AAA-40
                         C. Y....C             WG TLH ....P..EE      VN
                    V.WG            ∩    F...W              C.P.C     Cytomeg
                                                  WGFT.H  ..AC..N     FIB-5
```

FOURTH SERIES OF EXPERIMENTS

REFERENCES

1. Gregory A K, Yin N X, Capella J, Xia S, Newman K M, Tilson M D. Feature of autoimmunity in the abdominal aortic aneurysm. Arch Surg 1996: 23–25.
2. Tilson M D. Similarities of an autoantigen in aneurysmal disease of the human abdominal aorta to a 36-kDa microfibril-associated bovine aortic glycoprotein. Biochem. Biophys. Res. Commun. 213:40–43, 1995.
3. Xia S, Ozvath K, Hirose H, Tilson M D. Partial amino acid sequence of a novel 40 kDa human aortic protein, with vitronectin-like, fibrinogen-like, and calcium binding domains: aortic aneurysm-associated protein-40 (AAAP-40) [Human MAGP-3, proposed]. Biochem Biophys Research Commun. 1996; 219: 36–39.
4. Kobayashi R, Mizutani A, Hidaka H. Isolation and characterization of a 36 kDa microfibril associated glycoprotein by the newly synthesized isoquinolinesulfonamide affinity chromatography. Biochem Biophys Res Commun. 1994; 198:1262–6.
5. Kobayashi R, Tashima Y, Masuda H, Shozawa T, Numata Y, Miyauchi K, Hayakawa T. Isolation and characterization of a new 36-kDa microfibril-associated glycoprotein from porcine aorta. J Biol Chem 1989; 264: 17437–44.
6. Hirose H, Ozsvath K J, Xia S, Cifello V, Tilson M D. Detection of aortic aneurysm-associated autoantigenic protein 40 kDa (AAA D-40) with antibodies to vitronectin and fibrinogen, both immunohistochemically and with western immunoblots. Surgical Forum 1996, 82:370–373.
7. Oszvath, K J, Xia S, Hirose H, Tilson, M D. Two hypothetical proteins of human aortic adventitia, with Ig kappa, collagenous, and aromatic-rich motifs. Biochem. Biophys. Res. Com. (1996) 225:500–504.
8. Retrieve can be accessed by e-mail at "retrieve@ncbi.nlm.nih.gov"
9. http://kiwi.imagen.bcmtmc.edu:8088/bio/bio_home.html.
10. Ozsvath, K., Hirose, H., Xia, S., Tilson, M. D. Molecular Mimcry in Human Aneurysmal Diseases. Annals of New York Academy of Sciences, in press.
11. Beck, E N. Plasma Cell Infiltrates in Atherosclerotic Abdominal Aortic Aneurysm. Am J Clin Path 1986; 85:21–24
12. Rizzo, R. J., McCarthy, W. J., Dixit, S. N., et al Typing of Collagen and Content of Matrix Protein in Human Abdominal Aortic Aneurysm. J Vasc Surg 1989; 10:365–373.
13. Koch, A. E., Haines, G. K., Rizzo, R. J. et al. Human Abdominal Aortic Aneurysms: Immunophenotypic Analysis Suggesting an Immune Mediated Response. Am J Pathol 1990; 137:1199–1219
14. Brophy, C. M. Reilly, J. M., Smith, G J W, Tilson, M. D. The Role of Inflammation in Nonspecific Abdominal Aortic Aneurysm Disease. Ann Vasc Surg 19091; 5:229
15. Newman, K. M. Jean-Claude, J., Li, H., Ramey, W. G., Tilson, M. D. Cytokines that Activate Proteolysis are Increased in Abdominal Aortic Aneurysms. Circulation 1994; 90:II224–II227
16. Szekanecz, Z., Shar M. R., Pearce, W. H. Koch, A. E. Human Atherosclerotic Abdominal Aortic Aneurysms Produce Interleukin (IL)-6 and Interferon-Gamma but not IL-2 and IL-4: The Possible Role IL-6 and Inteferon-Gamma in Vascular Inflammation. Agents & Agents 1994; 42:159–162.
17. Koch, A. E., Kunkel, S. L., Pearce, W. H. et al. Enhanced Production of the Chemotactic Cytokines Interleukin-8 and Monocyte Chemoattractant Protein-1 in Human Abdominal Aortic Aneurysms. Am J Path 1993; 142:1423–1431.
18. Newman, K. M., Malon, A. M., Shin, R. D., et al. Matrix Metalloproteinases in Abdominal Aortic Aneurysm: Characterization, Purification , and Their Possible Sources. Connective Tissue Res 1994; 30:265–276
19. Newman, K. M., Jean-Clause, J., Li, H., Scholes, J. V., Ogata, Y., Nagase, H., Tilson, M. D., Cellular Localization of Matrix Metalloproteinases in the Abdominal Aortic Aneurysm Wall J. Vasc Surg 1994; 20:814–820.
20. Thompson, R. W. Holmes D. R., Mertens, R. A., et al. Production and Localization of 92 Kildalton Gelatinase in Abdominal Aortic Aneurysm. An Elastolytic MetalloProteinase Expressed by Aneurysm-Infiltrating Macrophages. J. Clin Invest 1995; 96:318–326.
21. Tilson, M. D. The Genetic Susceptibility to AAA Disease Resides in Major Histocompatibility Locus DR-Beta-1. Annals of the New York Academy of Sciences, in press.
22. Frennette, P. S., Wagner, D. D. Molecular Medicine Adhesion Molecules Part I. N. Engl J Med 1996; 334:1526–1529.
23. Genebank Accession Number: sp|P80520
24. Genebank Accession Number: gi|543129
25 Zhao, Z., Lee, C., Jiralerspong, S., et al. The Gene for A Human Microfibril-Associated Glycoprotein is Commonly Deleted in Smith Magenis Syndrome Patients. Human Mol Genetics 1995; 4:589–597.
26. Genebank Accession Number: gp|L38486
27. Genebank Accession Number: gi|1255044
28 Genebank Accession Number: sp|P16748
29. Genebank Accession Number: gi|437972
30. Genebank Accession Number: sp|16982

5TH SERIES OF EXPERIMENTS

EXPERIMENTAL DETAILS

The partial amino acid sequence of an aortic adventitial elastin-associated fibrillar protein may be the target of an autoimmune response in patients with abdominal aortic aneurysms (AAA).(1, 2, 3) Its apparent molecular weight is approximately 40 kDa, so it has been named aneurysm-associated antigenic protein—40 kDa (AAAP-40). It has similarities to microfibril-associated glycoprotein-36 kDa (MAGP-36)(4), which was reported by Kobayashi et al. to have a tissue distribution limited to the aorta in pig(5); unlike other microfibrillar proteins which appear to distribute ubiquitously throughout the body with elastin.(6) Accordingly, if AAAP-40 is the human homolog of MAGP-36, it would explain how an autoimmune reaction against this protein might have consequences more or less limited to the aorta and its branches.

CLONES 1 AND 5 HAVE IMMUNOGLOBULIN DOMAINS

An expression library was made from mRNA of the human aortic adventitia and screened in an effort to clone the cDNA for AAAP-40. Two of the first five clones (#1 and #5) have novel features and strongly resemble each other in domain structure.(7) While both have some features that occur in the families of microfibril-associated glycoproteins and other matrix proteins (like collagen), their most remarkable property is that each begins with a lengthy amino acid sequence (~100 residues) that is highly homologous to members of the immunoglobulin kappa family. The probability that this high degree of similarity is due to chance alone (as calculated by BlastP)(8) is in the range of $1 \times 10^{-50}$.

These are novel proteins, as matrix molecules with immunoglobulin domains have not been previously described. By analogy to the membrane-bound cell adhesion molecules (CAMs), the name Matrix Cell Adhesion Molecules (MAT-CAMs) is proposed for these unique clones. Hereafter, Clone 5 will be referred to as MAT-CAM 2; since it is the second member of this new family to be discovered.

THREE-DIMENSIONAL MODELING OF MAT-CAM 2 (CLONE 5)

Figure 16:
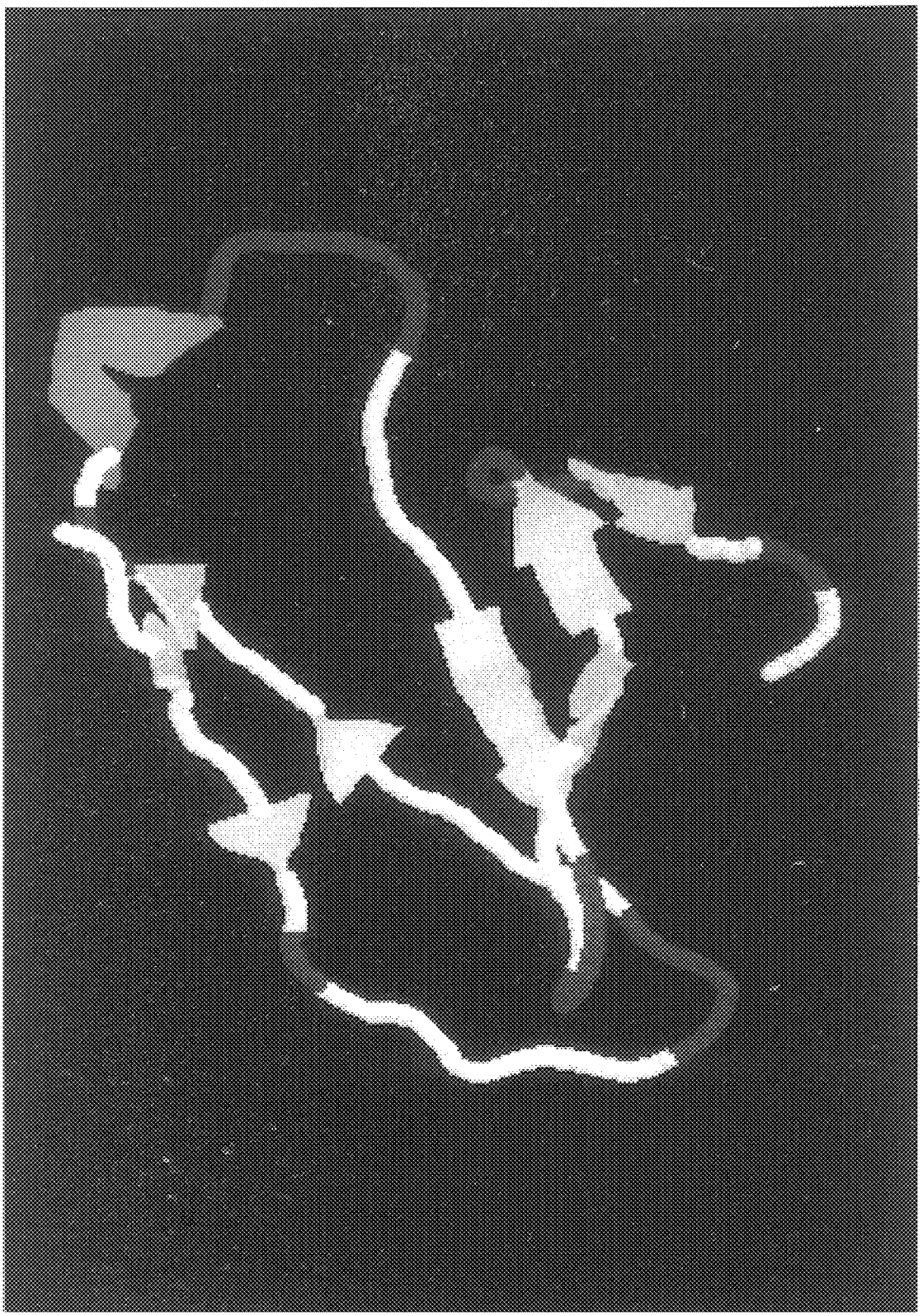

The three dimensional modeling of Clone 1 (MAT-CAM 1) is reported elsewhere. Interestingly, the N-terminal 124 residues form a sandwich of two antiparallel beta sheets, characteristic of the immunoglobulin superfamily. The structure of the N-terminal 124 residues of MAT-CAM 2 was modeled by SwissModel(9) on 11MIG.PDB, which was the most Esimilar immunoglobulin light chain for which a template was available (Blastp $p=1.3 \times 10^{-31}$) and displayed in three-dimensions by RasMol.(10) The antiparallel beta sheet sandwich of MAT-CAM 2 is illustrated in FIG. 16.

Figure 17:
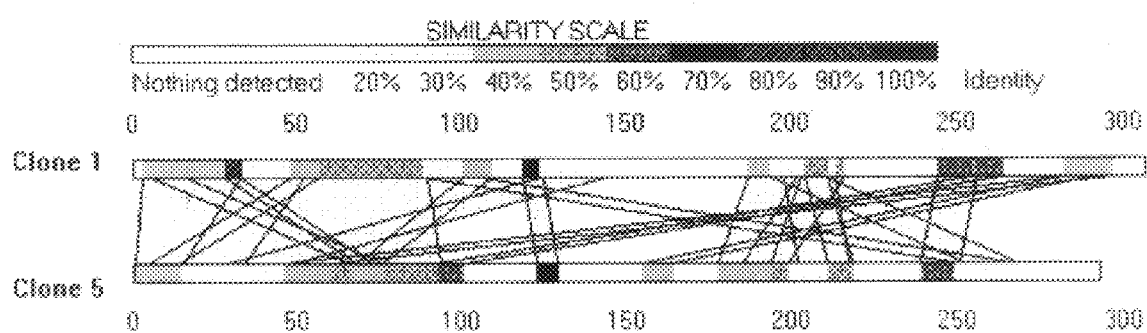

FIG. 17 shows a pair-wise comparison of the modeled sequence of MAT-CAMs 1 and 2 (as computed at the Biologist's Control Panel)(11) and displayed by LalnView. (12) There has obviously been substantial divergence in sequence, although the structure of the immunoglobulin sandwich is preserved. This result confirms again what has come to be seen as a common theme in molecular evolution; namely, that structure is much more highly conserved than sequence.

MOLECULAR EVOLUTION OF THE MAT-CAMS

Figure 18:
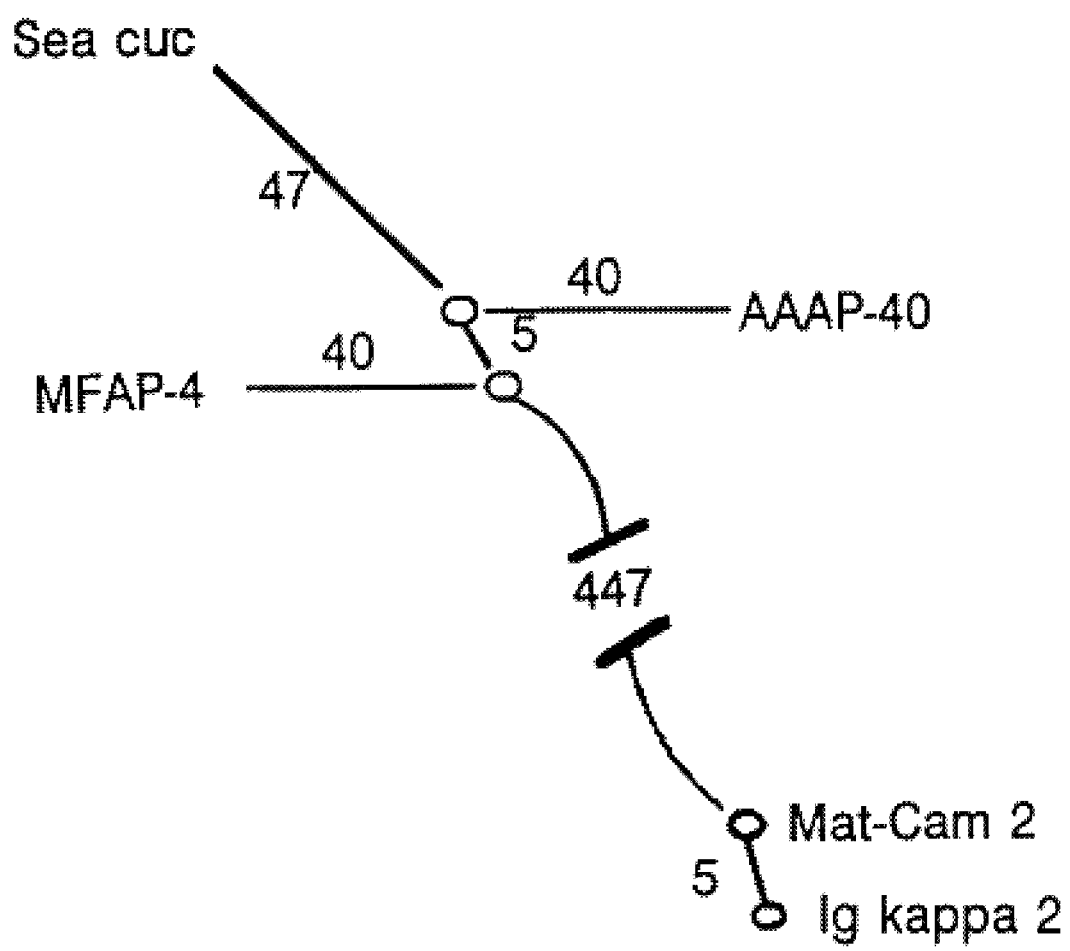

The PAM distances (point accepted mutations per 100 amino acids) have been calculated with AllAll(13) for the MAT-CAMs, the most similar immunoglobulins, the microfibril-associated glyco-proteins, and their presumed fibrinogen-like ancestor: fibrinogen-related protein-A precursor (SP¦P19477) of the invertebrate Echinoderm sea cucumber. For fibrinopeptide-B related proteins, a PAM unit has been estimated to be about 1 million years.(14) FIG. 18, which is drawn roughly to scale, illustrates some of these distances. One might surmise that there was a cluster of evolutionary activity among the matrix molecules around the time of the Cambrian radiation, followed much more recently by a cluster of activity around the time of appearance of soluble immunity in the cartilagenous sharks.

Figure 20:
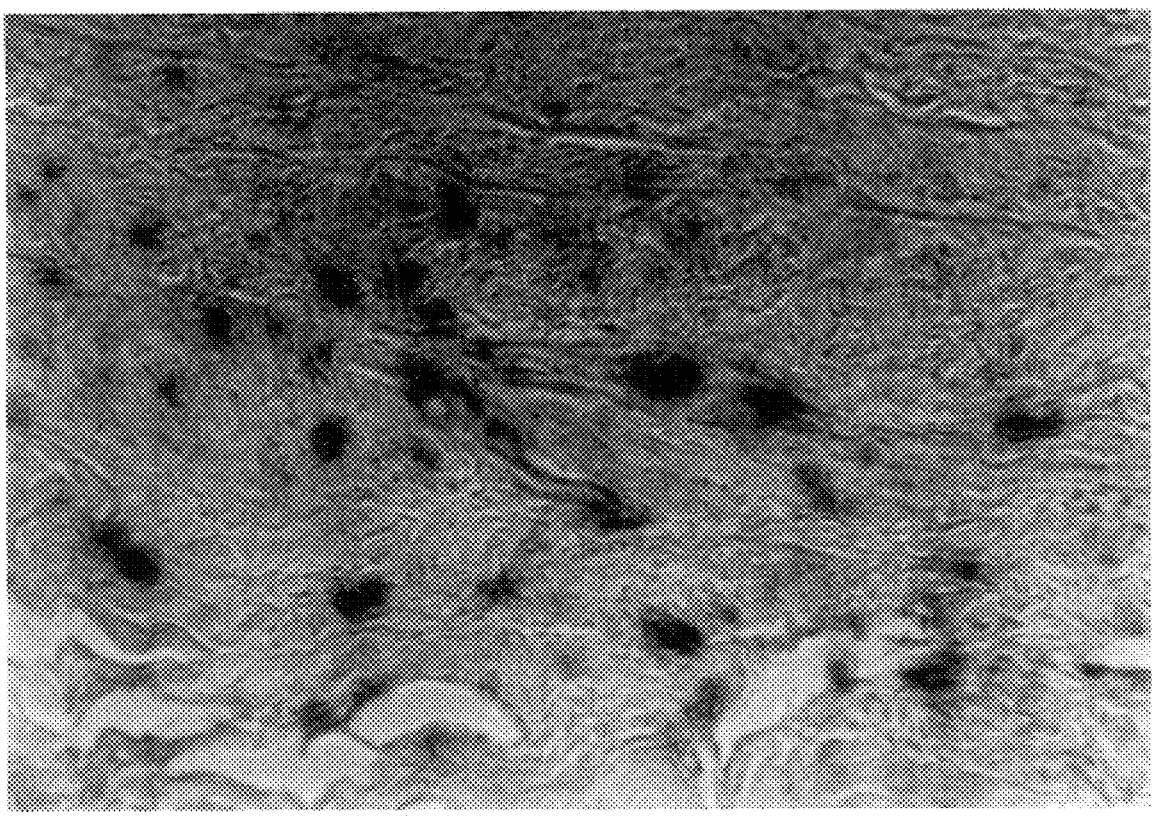

Two recent findings suggest that the proteins may he authentic gene products. First, FIG. 19 shows the result of an immunohistochemical experiment which compared the binding of antibody against Ig-kappa to the elastin-associated fibril of an aneurysmal aorta (as compared with the binding of an antibody against Ig-heavy chain). The binding of anti-Ig kappa to the matrix suggests that the putative MAT-CAMs are authentic connective tissue proteins. Second, FIG. 20 illustrates an in-situ hybridization of labeled clone 1 with a section of aortic wall. The observation that binding occurs to a mesenchymal cell instead of a lymphocyte buttresses the argument for authenticity.

Preliminary studies with a limited number of AAA patients and normals suggest that MAT-CAMs 1 and 2 may also be autoantigens like AAAP-40. However, there may be a whole family of aortic antigenic proteins related to the development of aneurysmal diseases.

FIFTH SERIES OF EXPERIMENTS

REFERENCES

1. Gregory A K, Yin N X, Capella J, Xia S, Newman K M, Tilson M D. Feature of autoimmunity in the abdominal aortic aneurysm. Arch Surg 1996: 23–25.
2. Tilson M D. Similarities of an autoantigen in aneurysmal disease of the human abdominal aorta to a 36-kDa microfibril-associated bovine aortic glycoprotein. Biochem Biophys Res Communications 213: 40–43, 1995.
3. Xia S, Ozvath K, Hirose H, Tilson M D. Partial amino acid sequence of a novel 40 kDa human aortic protein, with vitronectin-like, fibrinogen-like, and calcium binding domains: aortic aneurysm-associated protein-40 (AAAP-40) [Human MAGP-3, proposed]. Biochem Biophys Research Communications 1996; 219: 26–39.
4. Kobayashi R, Mizutani A, Hidaka H. Isolation and characterization of a 36 kDa microfibril associated glycoprotein by the newly synthesized isoquinolinesulfonamide affinity chromatography. Biochem Biophys Res Commune 1994; 198:1262–6.
5. Kobayashi R, Tashima Y, Masuda H, Shozawa T, Numata Y, Miyauchi K, Hayakawa T. Isolation and characterization of a new 36-kDa microfibril-associated qlycoprotein from porcine aorta. J Biol Chem 1989; 264: 17437–44.
6. Zhao Z, Lee C-C, Jiralerspong S, Juyal R C, Lu F, Baldini A, Greenberg F, Caskey C T, Patel P I. The gene for a human microfibril-associated glycoprotein is commonly deleted in Smith-Magenis syndrome patients. Human Mol Genetics 1995; 4: 589–597.
7. Ozsvath K J, Xia Shichao, Hirose H, Tilson M D. Two hypothetical proteins of human aortic adventitia, with Ig Kappa, collagenous, and aromatic-rich motifs. Biochem Biophys Research Communications (1996) 225: 500–504.
8. Altschul S F, Gish W, Miller W, Myers E W, Lipman D J. Basic local alignment search tool. J Mol Biol 1990; 215: 403–10.
9. Peitsch M C. Promod and swiss-model: internet based tools for automated comparative protein modeling. Biochem Soc Trans 1996; 24: 274. Available at Swissmod@ggr.co.uk.
10. Sayle R. RasWin Molecular Graphics, version 2.6. Freeware.
11. http://kiwi.imgen.bcm.tmc.edu:8088/bio/bio_home.html
12. Duret L. LALNVIEW v 2.2, available at the Biologist's Control Panel (reference above).
13. Korostensky C (webmaster). AllAll.html, available at http://cbrg.inf.ethz.ch.
14. Wilson A C, Carlson S S, White T J. Biochemical evolution. Ann Rev Biochem 1977; 46:573–639.

SIXTH SERIES OF EXPERIMENTS

EXPERIMENTAL DETAILS

Aortic aneurysms are a common disease of maturity, among the ten leading causes of death in men and women of ages 55–74.(1) Despite the mortality and suffering caused by this problem, research into the causes of the abdominal aortic aneurysm (AAA) has been neglected. According to a recent search of the computer resources at the National Institutes of Health (NIH) on the subject of funded grants, the NIH is spending something like 1.7 billion dollars a year on AIDS, compared to a few hundred thousand dollars on aneurysms; even though almost as many people die each year from aortic aneurysms as from AIDS (about 25,000 versus 34,000).(1) Autoimmunity has been implicated in the pathogenesis of the AAA. Immunoglobulin-G (IgG) purified from the wall of AAA specimens is immunoreactive with proteins of ~80 kDa and ~40 kDa extractable from the aortic matrix and with matrix elements that resemble elastin-associated microfibrils in immunohistochemical preparations.(2,3) This putative aiitoantigen has been purified partially sequenced.(4)

The notion that aneurysmal disease has features in common with autoimmune diseases like rheumatoid arthritis opens the way for many new research approaches to the issues of treatment and prevention. If specific antibodies are detectable in serum, as preliminary results suggest, it may be possible to detect susceptibility to the disease before significant aortic degeneration has occurred. If tolerance for the aortic autoantigen can be induced, it may be possible to down-modulate progression of aortic degeneration (as has been accomplished in rheumatoid arthritis (5)).

Clifton (6) reported an instance of familial clustering of AAA and 15 Tilson (7,8) postulated a general genetic basis for susceptibility. Numerous subsequent studies have added support to the genetic hypothesis.(9–21) The most recent statistical model for the mode of inheritance predicts a dominant gene.(22)

Three candidate genes have been proposed. 1) A mutated gene for the alpha chain of Type III Collagen (COL3A1) was found to cosegregate with aneurysmal disease in one family, (23) but further studies revealed only two additional positive families in another 50 evaluated.(24) 2) A deficiency allele for alpha-1 antitrypsin (MZ) was found in five (11%) of 47 patients,(25) so if this gene has etiological significance in some individuals, it accounts for a relatively small subset. 3) An identical nucleotide substitution in the cDNA for Tissue Inhibitor of Metalloproteinases (TIMP) was found in two of six patients;(26) but this finding turned out to be trivial, since the polymorphism occured in the third position of the codon. Accordingly, the gene and/or genes responsible for most cases of AAA remain to be discovered.

Evidence for Autoimmunity in the AAA

The walls of abdominal aortic aneurysms (AAA's) contain abundant cells of chronic inflammation, particularly in the adventitia.(27–29) Russell bodies have also been observed in the AAA tissues, which are a feature of autoimmune diseases like Hashimoto's thyroiditis.(28) Additional findings from since that time include 1) elevated levels of cytokines that activate proteolysis in AAA tissue;(30) 2) elevated content of plasmin (31) (the principal activator of the matrix metallo-proteinases); 3) increased amounts of proteins immunoreactive with antibodies against collagenase (MMP-1)(32), stromelysin (MMP-3), and gelatinase-B (MMP-9). (33) In our original study of 1991 we noted substantial increases in the IgG present in the walls of aortic aneurysmal tissue by comparison to atherosclerotic occlusive disease and control aortas (28). This observation led to further work to identify the putative autoantigen.

Purification of an Autoantigen

IgG from aneurysm wall by affinity to Protein-A was purified and used as a probe in immunohistochemical preparations of normal aorta to determine whether the autoantigen is an aortic matrix protein.(2) Taking a similar approach to the assignment of a molecular weight to the putative autoantigen, used the AAA IgG was used as a probe on Western immunoblots of soluble proteins extracted from the normal aorta.(2)

Amino acid sequencing of peptides from the 80 kDa immunoreactive protein (3) led to a postulation that the autoantigen of AAA disease is the human homolog of a bovine aortic protein discovered by Kobayashi, named microfibril-associated glycoprotein-36 (MAGP-36).(34) MAGP-36 occurs in nature as a dimer, so it was hypothesized that the 80 kDa protein is also a dimer. Further extractions under chaotropic reducing conditions were used to purify sufficient human protein with Mr ~40 kDa to 1) confirm that the 40 kDa species is also immunoreactive with AAA IgG; and 2) confirm that it is closely related to the MAGP family by direct amino acid sequencing.(4)

At first this 40 kDa protein was called "Aortic Aneurysm Antigenic Protein-40" (AAAP-40).(4) Since it appears to be the third member of the MAGP family to be discovered in man, the abbreviation MAGP-3 may be preferred in the future. Tables I and II (in the First Series of Experiments) display similarities of AAAP-40 with two other well-characterized microfibril-associated glycoproteins: MAGP-36(34) and MFAP-4.(35)

Fibrinogen-like domains are well-known in the MAGP's. The sequence of AAA-40 shown in Table I (in the First Series of Experiments) has regions of homology with sequences in the alpha and beta chains of fibrinogen. Another sequence that we have determined (data not shown) matches residues 283–292 in the gamma chain. Since the three fibrinogen chains are believed to have a single ancestral gene, it would appear likely that AAAP-40 is related to the common ancestor since it has motifs that are used in all three fibrinogen subunits.

Kobayashi et al noted that MAGP-36 has the property of calcium-binding,(34) although a candidate site for the calcium-binding domain has not been proposed. Kielty and Shuttleworth have observed that incubation of intact microfibrils with EDTA rapidly results in gross disruption of microfibrillar organization, which can be reversed by replacing calcium.(36) Since fibrillin has 43-EGF-like motifs with calcium binding consensus sequences, and calcium has been proposed to orchestrate the assembly of tropoelastin to the microfibril and hold it in register for crosslinking,(37) it was hypothesize that the calcium-binding domain of AAAP-40 may play a role in calcium-dependent microfibril assembly in the aorta. When GenBank was searched for homologies of AAAP-40 and MAGP-36, sequences were found in calcium-binding myeloid-related protein (>pir|A44111:# 144–154), the calcium-binding domain of human fibrinogen-beta, and bovine aggrecan (>pir|A39808:# 59–66) that have similarities to MFAP-4, MAGP-36, and AAAP-40. Bold type is used in Table II (in the First Series of Experiments) to highlight residues that appear to be conserved, with possible significance for the calcium-binding function.

Another matrix protein detected in human embryonic tissue (sulfated protein 30 kDa=SP-30) has been reported to be immunoreactive with monoclonal antibodies against human vitronectin.(38) A sequence of AAAP-40 that matches residues# 230–240 in human vitronectin is shown in Table II (in the First Series of Experiments). Tomasini-Johansson et al proposed that SP30 is the human homolog of MAGP-31, but since MAGP-31 does not have this twelve residue vitronectin-like domain, it is believed that SP-30 is more likely to be closely related to AAAP-40, or to another MAGP with a vitronectin-like domain that is ubiquitously expressed during embryogenesis.

Parallels with Rheumatoid Arthritis

The association of rheumatoid arthritis (RA) and Class II Major Histocompatibility Locus (MHC) DR4 was first reported by Stastny in 1978.(39) However, it became evident that DR4 was not always associated with RA in different racial/ethnic populations, and the reader is referred to a review article by Ollier and Thomson (40) which describes the state of the field leading to the formulation of the hypothesis of the shared epitope by Gregersen, Silver, and Winchester in 1987.(41) The hypothesis is that arthritogenic DR molecules share a highly conserved sequence of amino acids in their third hypervariable region (amino acid positions 70–74).

In the context of a rather homogeneous population seen by the arthritis group at the Mayo Clinic, evidence for the shared epitope seems compelling. Weynand and colleagues have reported that 98 of 102 (96%) patients express one of the major North American disease-linked polymorphisms (*04, *0101, or *1402).(42) Forty-seven patients carried a double dose of the relevant sequence stretch. Nodular disease was expressed in 100% of the patients typed as HLA-DRB1*04/04. Patients with a double dose of the shared sequence tend to have more severe manifestations of rheumatoid disease.

A Pilot Study to Test the Notion of an Association with MHC Class II DR

As a pilot study we 26 patients have been tissue typed with AAA's. Because of the demographics of the patient population of our hospital system, there were five Americans of color in the sample. Since AAA's are much less common in African Americans than in Caucasians, these ten haplotypes are particularly interesting. It has been a working hypothesis of Tilson that Americans of color might have a double dose of the susceptibility allele. The results of allele frequency analysis in these five patients compared with the expected frequencies are presented in Table X. The expected frequencies were derived from the tables published by the Eleventh International Histocompatibility Workshop held in Yokohama, Japan in November 1991.(43) Only three DR alleles were detected among the ten haplotypes of interest. The data in Table X suggest that patients with alleles for DR 2, 12 and 13 occurred significantly more often than expected by chance alone ($p=3\times10^{-4}$).

Inspection of the amino acid sequences of the most common alleles for these three DRB1 types revealed that the residues that they have in common are at positions 31 and 47 of the second hypervariable region; specifically, both residues are phenylalanines (phe).(44) The other alleles that have phe at positions 31 and 47 are DR 3 and DR 11. Revisiting the data on the 21 non-Black patients in the original series, 16 (75%) have an allele with phenylalanine at positions 31 and 47; and four of these have a double dose of one of the putative "aneurysmogenic" alleles.

If the requirement for a phe at position 47 is relaxed to permit a phe at position 371 one hundred percent (21 out of 21) non-Black patients have a putative aneurysmogenic allele; and 50% of the total patients (13/26) have a double dose. Thus, there is now a testable hypothesis to evaluate going forward to look at additional patients prospectively.

The notion that AAA is an autoimmune disease of maturity like rheumatoid arthritis offers many opportunities for new knowledge, including 1) a better understanding of etiological influences; 2) novel diagnostic approaches to the detection of susceptibility (DR) and disease activity (serum IgG level) before the aorta has commenced to dilate; and, 3) therapeutic interventions (induction of tolerance) that might change the natural history of the disease. In terms of etiology, several instances of molecular mimicry by common (and uncommon) pathogens have been found, (45) wherein the shared epitopes may provide informative explanations not only for features of AAA disease, but also for previously unexplained phenomena related to the clinical manifestations of certain infections.

TABLE X

Allele frequencies in five Americans of Color with AAA (AOC-AAA, ten haplotypes) with the expected frequencies for these alleles in North American Blacks (NAB) as reported by the International Workshop in 1991 (Table 12, 132 haplotypes).[43] The cumulative probability of this result is $p = 3 \times 10^{-4}$. Probabilities were calculated by Fisher's Exact Test for 2 x 2 Contingeny Tables.

| Allele | Frequency in AOC-AAA | Frequency in NAB | p |
|---|---|---|---|
| DRB1*02 | 40% | 12% | .037 |
| DRB1*12 | 30% | 5% | .023 |
| DRB1*13 | 30% | 15% | .370 |

SIXTH SERIES OF EXPERIMENTS

REFERENCES

1. Silverberg E, Lubera J A. Cancer statistics. CA—A Cancer Journal for Clinicians 1996; 46: 5–27.
2. Gregory A K, Yin N X, Capella J, Xia S, Newman K M, Tilson M D. Features of autoimmunity in the abdominal aortic aneurysm. Archives of Surgery, 1996; 131: 85–88.
3. Tilson M D. Similarities of an autoantigen in aneurysmal disease of the human abdominal aorta to a 36-kDa microfibril-associated bovine aortic glycoprotein. Biochem Biophys Res Communications 213: 40–43, 1995.
4. Xia S, Ozsvath K, Hirose H, Tilson M D. Partial amino acid sequence of a novel 40 kDa human aortic protein, with vitronectin-like, fibrinogen-like, and calcium binding domains: aortic aneurysm-associated protein-40 (AAAP-40) [Human MAGP-3, proposed]. Biochem Biophys Research Communications 1996; 219: 36–39.
5. Trentham D E, Dynesium-Trentham R A, Oran E J, et al. Effects of oral administration of type II collagen on rheumatoid arthritis. Science. 1993; 261: 1727–1730.
6. Clifton M. Familial abdominal aortic aneurysms. Br J Surg 1977; 64:765–766.
7. Tilson, M D, in discussion of Busuttil R W, Abou-Zamzam A M, Machleder H I. Collagenase activity of the human aorta: A comparison of patients with and without abdominal aortic aneurysms. Arch Surg 1980; 115: 1373–8.
8. Tilson M D, Dang C. Generalized arteriomegaly—a possible predisposition to the formation of abdominal aortic aneurysms. Arch Surg 1981; 16:1030.
9. Tilson M D, Seashore M R. Human genetics of abdominal aortic aneurysm. Surg Gynecol Obstet 1984; 15:129.
10. Tilson M D, Seashore M R. Fifty families with abdominal aortic aneurysms in two or more first-order relatives. Am J Surg 1984; 147: 551–553.
11. Tilson M D, and Seashore M R. Ninety-four families with clustering of abdominal aortic aneurysms (AAA). Circulation, Part II 1984; 70: II-141.
12. Norrgard O, Rais O, Angquist K A. Familial occurrence of abdominal aortic aneurysms. Surgery 1984;95:650–656.
13. Johansen K, Koepsell T. Familial tendency for abdominal aortic aneurysms. JAMA 1986; 256: 1934–1936.
14. Powell J T, Greenhalgh R M. Multifactorial inheritance of abdominal aortic aneurysm. Eur J Vasc Surg 1987; 1:29–31.
15. Cole C W, Barber G G, Bouchard A G, McPhail N V, Roberge C, Waddell W G, Wellington J L. Abdominal aortic aneurysm: Consequences of a positive family history. Can J Surg 1988;32:117–120.
16. Collin J, Walton J. Is abdominal aortic aneurysm a familial disease? Br Med J 1989; 299: 493.
17. Darling III R C, Brewster D C, Darling R C, et al. Are familial abdominal aortic aneurysms different? J Vasc Surg 1989; 10:39–43.
18. Loosemore T M, Child A H, Dormandy J A. Familial abdominal aortic aneurysms. J Roy Soc Med 1988; 81: 472–3.
19. Bengtsson H, Norrgard O, Angquist K A, Eckberg O, Obereg L, Bergqvist D. Ultrasonographic screening of the abdominal aorta among siblings of patients with abdominal aortic aneurysms. Br J Surg 1989; 76: 589–591.
20. Webster M W, St. Jean P L, Steed D L, et al. Abdominal aortic aneurysm: Results of a family study. J Vasc Surg 1991; 13:366–372.
21. Majumder P P, St. Jean P L, Ferrell R E, Webster M W, Steed D L. On the inheritance of abdominal aortic aneurysm. Am J Hum Genet 1991; 48: 164–170.
22. Verloes A, Sakalihasan N. Koulischer L, Limet R. Aneurysms of the abdominal aorta: familial and genetic aspects in three hundred pedigrees. J Vasc Surg 1995; 21: 646–55.
23. Kontusaari S, Tromp G, Kuivaniemi H, Romanic A, Prockop D J. A mutation in the gene for Type III procollagen (COL3A1) in a family with aortic aneurysms. J Clin Invest 1990; 86:1465–1473.
24. Tromp G, WU Y, Prockop D J, et al (24 authors). Sequencing of cDNA from 50 unrelated patients reveals that mutations in the triple-helical domain of Type III procollagen are an infrequent cause of aortic aneurysms. J Clin Invest. 1993; 91:2539–2545.
25. Cohen J R, Sarfati I, Ratner L, Tilson M D. Alpha-1 antitrypsin phenotypes in patients with abdominal aortic aneurysms. J Surg Res 1991; 49:319–321.
26. Tilson M D, Reilly J M, Brophy C M, Webster E L, Barnett T R. Expression and sequence of the gene for tissue inhibitor of metalloproteinases in patients with abdominal aortic aneurysms. J Vasc Surg 1993; 18: 266–70.
27. Koch A E, Haines G K, Rizzo R J, Radsevich J A, Pope R M, Robinson P G, Pearce W H. Human abdominal aortic aneurysms: Immunophenotypic analysis suggesting an immune mediated response. Am. J. Pathol 1990; 137: 1199–1219.
28. Brophy C M, Reilly J M, Walker-Smith G J, Tilson M D. The role of inflammation in non-specific abdominal aortic aneurysm disease. Annals of Vascular Surgery 1991; 5: 229–233.
29. Beckman E N. Plasma cell infiltrates in abdominal aortic aneurysms. Amer. J. Clin. Path. 1986; 85: 21–24.
30. Newman K M, Jean-Claude J, Li H, Ramey W G, Tilson M D. Cytokines that active proteolysis are increased in abdominal aortic aneurysms. Circ. 1994; 90: 224–227.
31. Jean-Claude J, Newman K M, Li H, Tilson M D. Possible key role for plasmin in the pathogenesis of abdominal aortic aneurysms. Surgery, 1994; 116:472–8.
32. Irizarry E, Newman K, Gandhi R, Nackman G, Wishner S, Tilson M D. Demonstration of interstitial collagenase in abdominal aortic aneurysms. J Surg Res 1993; 54: 571–574.
33. Newman K M, Ogata Y, Malon A M, Irizarry E, Gandhi R H, Nagase H, Tilson M D. Identification of matrix metalloproteinases 3 (stromelysin-1) and 9 (gelatinase B) in abdominal aortic aneurysm. Arteriosclerosis and Thrombosis, 1994; 14: 1315–1320.
34. Kobayashi R, Mizutani A, Hidaka H. Isolation and characterization of a 36-kDa microfibril-associated glycoprotein by the newly synthesized isoquinolinesulfonamide affinity chromatography. Biochem Biophys Res Communic 1994; 198: 1262–6.
35. Zhao Z, Lee C-C, Jiralerspong S, Juyal R C, Lu F, Baldini A, Greenberg F, Caskey C T, Patel P I. The gene for a human microfibril-associated glycoprotein is commonly deleted in Smith-Magenis syndrome patients. Human Mol Genetics 1995; 4: 589–597.
36. Kielty C M, Shuttleworth C A (1993). The role of calcium in the organization of the fibrillin microfibrils. FEBS 336: 323–326.
37. Mecham R P, Heuser J E (1991). in Cell Biology of Extracellular Matrix (Hay ED, ed) 2nd Ed, pp 79–109, Plenum Press, New York.
38. Tomasini-Johansson B R, Ruoslahti E, Pierschbacher M D (1993). A 30 kDa sulfated extracellular matrix protein immunologically crossreactive with vitronectin. Matrix 13: 203–214.
39. Stastny P. Association of the B-cell alloantigen DRw4 with rheumatoid arthritis. N Engl J Med 1978; 298: 869–871.
40. Ollier W, Thomson. Population genetics of rheumatoid arthritis. Rheum Dis Clinics of North Amer 1992; 18: 741–759.
41. Gregersen P K, Silver J, Winchester R J. The shared epitope hypothesis: an approach to understanding the molecular genetics of susceptibility to rheumatoid arthritis. Arthritis Rheum 1987; 30: 1205–13.
42. Weynand C M, Hicok K C, Conn D L, Goronzy J J. The influence of HLA-DRB1 genes on disease severity in rheumatoid arthritis. Ann Int Med 1992; 117: 801–6.
43. Tsuji K, Aizawa M, Sasazuki T. HLA 1991: Proceedings of the Eleventh International Histocompatibility Workshop and Conference held in Yokohama, Japan, Nov. 6–13, 1991. Oxford Univ Press, Oxford, 1992; 1: Table 12: W15.1.
44. Lechler R I, Simpson E, Bach F H. Major and Minor Histocompatibility Antigens: An Introduction. in Transplantation Immunology, eds. FH Bach, H. Auchincloss Jr. Wiley-Liss, New York, 1995, pp 1–34.
45. Ozsvath K J, Hirose H, Xia S, Tilson M D. Molecular mimicry in human aortic aneurysmal diseases (abstract). Annals of the NY Acad Sciences, in press.
46. GenBank accession number >pir|A44111: residues 144–154.
47. GenBank accession number >pir|A39808: residues 59–66.

SEVENTH SERIES OF EXPERIMENTS

EXPERIMENTAL DETAILS

Autoimmunity has been implicated in the pathogenesis of the abdominal aortic aneurysm (AAA).(1–3) Studies to identify one of the putative autoantigens have revealed amino acid sequences homologous to the bovine aortic microfibril-associated glyprotein-36 kDa (MAGP-36).(4, 5) We have partially sequenced this putative autoantigen,(6) and computerized searches have revealed homologies with proteins of two microorganisms associated with aneurysmal conditions: Treponema pallidum (T pall) and herpes simplex. The concept of molecular mimicry suggests that aneurysms in these infectious conditions might be on the basis of shared epitopes. In other words, an immune response against the pathogen might also attack an essential structural protein of the aortic matrix. The present experiments were carried out to test the hypothesis that the aortic protein shares epitopes with these pathogens.

Methods

Immunohistochemistry was performed using rabbit anti-T pall and rabbit antiherpes antibodies (ViroStat, Portland, Me.) versus sections of normal and aneurysmal aorta.

Purified proteins of T pall (T pure, Lee Laboratories, Grayson, Ga.) were separated by SDS-PAGE electrophoresis (12.5%), and immunoblots were prepared with the above rabbit antibodies and also with purified IgGs obtained from AAA wall and control serum. The filters were blocked with 5% dry milk in PBS prior to incubating with first antibody. After a series of washes, the filters were incubated with a second antibody; alkaline phosphatase-conjugated antibody (goat anti-human IgG, Sigma, St. Louis, Mo., for the filters incubated with human IgG, 1:1000, and goat anti-rabbit IgG for the filter incubated with anti-T pall, 1:2500).

The filters were developed using Vectastain NBT-BICP (Vector Laboratories, Burlingame, Calif.).

Results

Figure 21:
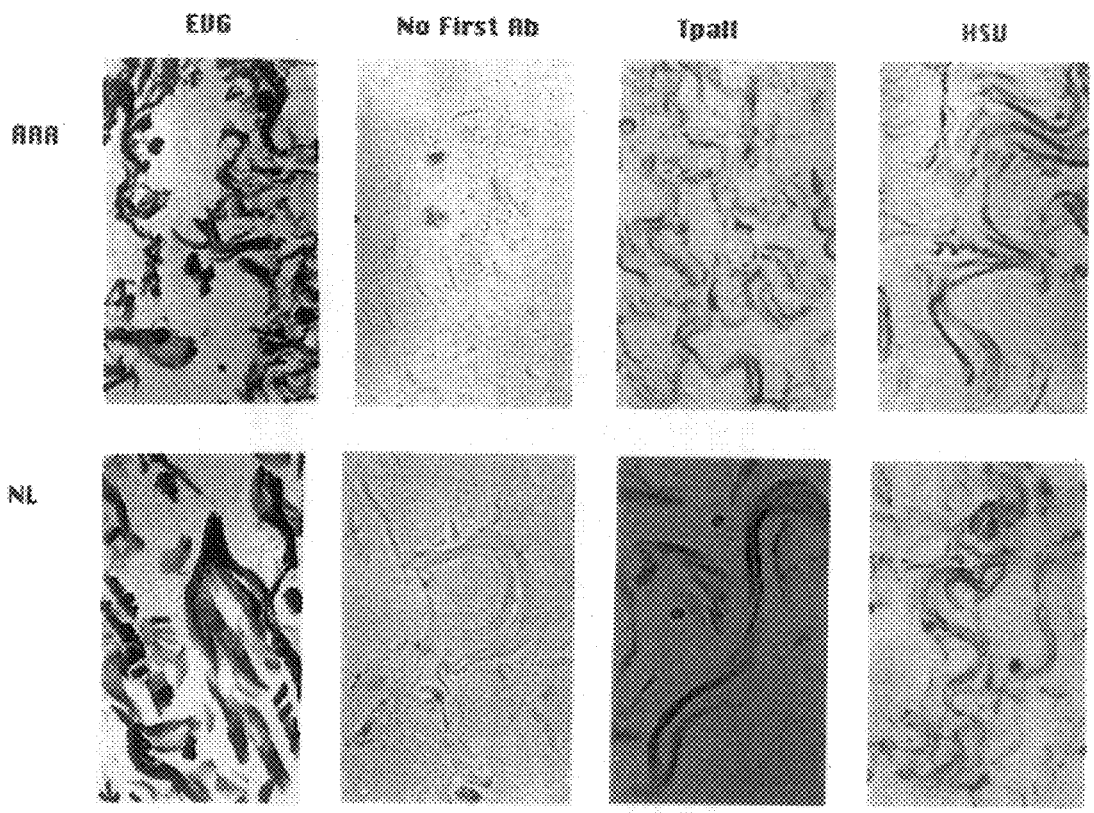
Figure 22:
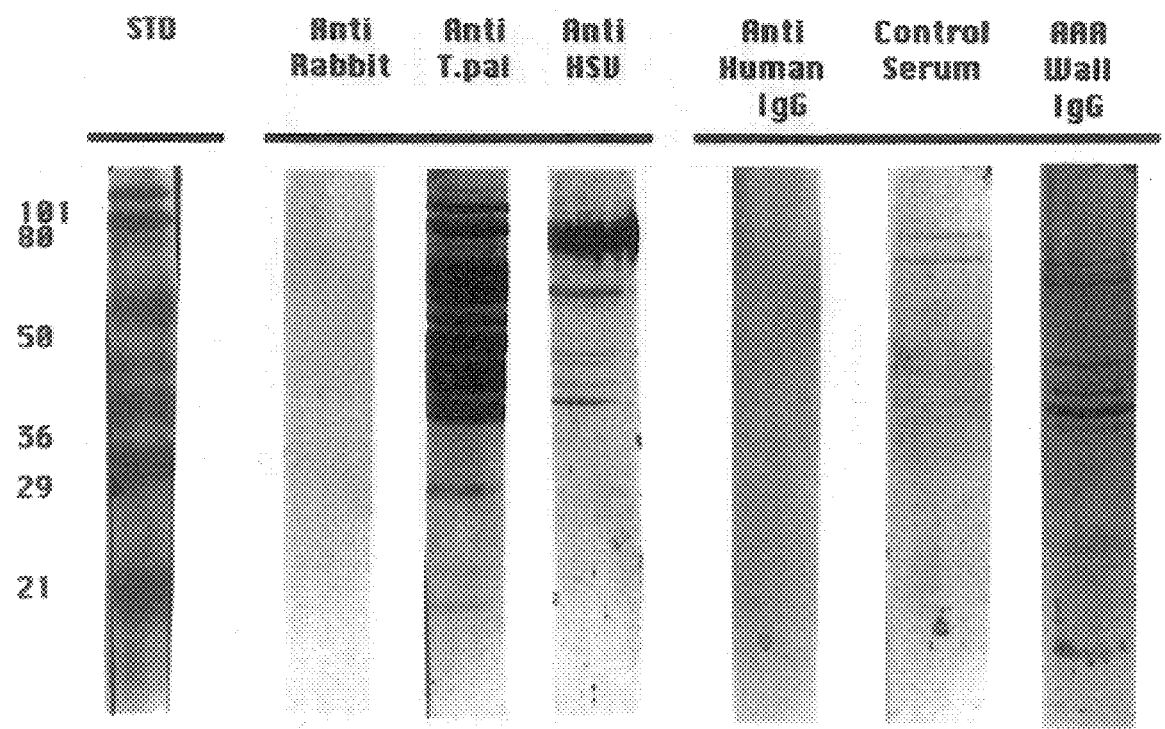

Rabbit antibodies against T pall and herpes bound to the adventitial elastin-associated microfibril (FIG. 21). Immunoreactive proteins in T pall were also identified phi with both rabbit antibodies, and also with IgG purified from AAA wall (FIG. 22).

Discussion

The notion of molecular mimicry is that epitopes of microbial pathogens may so closely resemble some of the host's normal proteins that infection with the organism may trigger an autoimmune disease.(7) Herpes simplex virus has recently been implicated as possibly having some role in the abdominal aortic aneurysm.(8) Considering the present hypothesis that herpes may exert its influence on the pathogenesis of the aortic aneurysm by molecular mimicry, the observations of DePalma about an outbreak of ruptured aneurysms in a colony of Capuchin monkeys are quite extraordinary.(9) Several years prior to the manifestations of aneurysmal disease in the monkeys, they had been experimentally infected at the National Institutes of Health with herpes virus.

Similarly, the relationship between the development of luetic aneurysms in patients infected with *T pall* has never been adequately explained. The usual explanation that aortic smooth muscle cells die of malnutrition because the spirochetes proliferate in the vasa vasorum seems far-fetched.(9) It is hypothesized that an epitope is shared by the spirochete and the elastin-associated aortic microfibril, which triggers the destruction of aortic matrix.

In summary, it is hypothesized that herpes and syphilis are associated with auto-immune destruction of structural load-bearing elements of the aorta because of epitopes shared with the aortic elastin-associated microfibril. Recent assignment of the gene responsible for Marfan syndrome to fibrillin, [10] which is a component of the microfibril, underscores the importance of microfibrillar integrity in preventing aneurysmal dilation.

The present finding have diagnostic and therapeutic implications. From the diagnostic perspective, it may be possible to develop a serum test for immune titer against the autoantigen, which might identify individuals susceptible to aneurysm formation prior to aortic enlargement. From the therapeutic perspective, it may be possible in the future to induce tolerance to the autoantigen in the AAA-susceptible individual, possibly slowing or preventing progression of the disease.

These findings suggest that the basis for the association of lues and herpes with aneurysmal diseases may be due to molecular mimicry of these pathogens with epitopes of the normal human aortic elastin-associated microfibril.

REFERENCES FOR SEVENTH SERIES OF EXPERIMENTS

1. Koch, A. E., G. K. Haines, R. J. Rizzo, J. A. Radsevich, R. M. Pope, P. G. Robinson & W. H. Pearch. 1990. Human abdominal aortic aneurysms: Immunophenotypic analysis suggesting an immune mediated response. Am. J. Pathol. 137:1199–1219.
2. Brophy, C. M., J. M. Reilly, G. J. Walker-Smith & M. D. Tilson. 1991. The role of inflammation in non-specific abdominal aortic aneurysm disease. Ann. Vasc. Surg. 5:229–233.
3. Gregory, A. K., N. X. Yin, J. Capella, S. Xia, K. M. Newman & M. D. Tilson. 1996. Features of autoimmunity in the abdominal aortic aneurysm. Arch. Surg. 131:85–88.
4. Tilson, M. D. 1995. Similarities of an autoantigen in aneurysmal disease of the human abdominal aorta to a 36-dDa microfibril-associated bovine aortic glycoprotein. Bio-chem. Biophys. Res. Commun. 213:40–43.
5. Kobayashi, R., A. Mizutani & H. Hidaka. 1994. Isolation and characterization of a 36-kDa microfibril-associated glycoprotein by the newly synthesized isoquinoline-sulfonamide affinity chromatography. Biochem. Biophys. Res. Commun. 198:1262–1266.
6. Xia, S., K. Ozsvath, H. Hirose & M. D. Tilson. 1996. Partial amino acid sequence of a novel 40 kDa human aortic protein, with vitronectin-like, fibrinogen-like, and calcium binding domains: Aortic aneurysm associated protein -40 (AAAP-40) [Human MAG-3, proposed]. Biochem. Biophys. Res. Commun. 219:36–39.
7. Fujinami, R. S. & M. B. Oldston. 1989. Molecular mimicry as a mechanism for virus-induced autoimmunity. Immunol. Res. 8:3–15.
8. Tanaka, S., K. Komori, K. Oradome, K. Sugimachi & R. Mori. 1994. Detection of active cytomegalovirus infection in inflammatory aortic aneurysms with RNA polymerase chain reaction. J. Vasc. Surg. 20:235–243.
9. DePalma, R. G. 1990. In The Cause and Management of Aneurysma. R. M. Greenhalgh, J. A. Mannick & J. T. Powell, Eds.: 97–104. W. B. Saunders Company. London.
10. Dietz, H. C., G. R. Cutting, R. E. Pyeritz, et al. 1991. Marfan syndrome caused by a recurrent de novo missense mutation in the fibrillin gene. Nature 352:337–339.

---

---

What is claimed is:

1. An isolated microfibrillar protein of approximately 40 kDa which is purified from human aortic tissue and binds immunoreactively with immunoglobulin purified from human abdominal aortic aneurysm (AAA) tissue.

2. The isolated microfibrillar protein according to claim 1, which is capable of forming a disulfide-bonded dimer of approximately 80 kDa.

3. The isolated microfibrillar protein according to claim 1, wherein purification of said protein from said human aortic tissue comprises extraction of said protein under reducing conditions.

4. The isolated microfibrillar protein according to claim 1, having the amino acid sequence set forth in SEQ ID NO:1.

5. A recombinantly produced human aortic microfibrillar protein which binds immunoreactively with both immunoglobulin purified from human AAA tissue and human kappa immunoglobulin and having a molecular weight of approximately 24 kDa–28 kDa.

6. A recombinantly produced human aortic microfibrillar protein of approximately 40 kDa which binds immunoreactively with immunoglobulin purified from human AAA tissue.

7. A kit for detecting the presence of immunoglobulin wherein said immunoglobulin binds immunoreactively with a microfibrillar protein purified from human aortic tissue in a sample, and wherein said human aortic microfibrillar protein is selected from the proteins of any of claims 1, 4, and 6, which comprises:

(a) a solid support having a plurality of covalently linked probes which may be the same or different, each probe of which comprises said human aortic protein; and (b) a means for determining the presence of said immunoglobulin.

8. The kit of claim 7, wherein said means for determining the presence of said immunoglobulin is a detectable label.

9. The kit of claim 8, wherein said detectable label is radioactive isotope, enzyme, dye, biotin, a fluorescent label or a chemiluminescent label.

* * * * *